US010759838B2

(12) United States Patent
Lenardo et al.

(10) Patent No.: US 10,759,838 B2
(45) Date of Patent: Sep. 1, 2020

(54) MYELIN OLIGODENDROCYTE GLYCOPROTEIN, MYELIN BASIC PROTEIN, AND PROTEOLIPID PROTEIN COMPOSITIONS AND METHODS OF USE

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Michael J. Lenardo, Bethesda, MD (US); Jian Li, Rockville, MD (US); Lixin Zheng, Rockville, MD (US); Jae W. Lee, Philadelphia, PA (US); Wei Lu, Rockville, MD (US)

(73) Assignee: The United States of America, as represented by the Secretary, Department of Health & Human Services, Rockville, MD (US)

( * ) Notice: Subject to any disclaimer, the term of this patent is extended or adjusted under 35 U.S.C. 154(b) by 0 days.

(21) Appl. No.: 15/556,738

(22) PCT Filed: Mar. 9, 2016

(86) PCT No.: PCT/US2016/021571
§ 371 (c)(1),
(2) Date: Sep. 8, 2017

(87) PCT Pub. No.: WO2016/145086
PCT Pub. Date: Sep. 15, 2016

(65) Prior Publication Data
US 2018/0105566 A1   Apr. 19, 2018

Related U.S. Application Data

(60) Provisional application No. 62/219,851, filed on Sep. 17, 2015, provisional application No. 62/130,285, filed on Mar. 9, 2015.

(51) Int. Cl.
C07K 14/47 (2006.01)
A61K 38/17 (2006.01)
A61P 25/28 (2006.01)
A61K 38/13 (2006.01)

(52) U.S. Cl.
CPC .......... C07K 14/4713 (2013.01); A61K 38/13 (2013.01); A61K 38/1709 (2013.01); A61P 25/28 (2018.01); C07K 2319/21 (2013.01); C07K 2319/50 (2013.01)

(58) Field of Classification Search
None
See application file for complete search history.

(56) References Cited

U.S. PATENT DOCUMENTS

| 8,088,389 B1* | 1/2012 | Ben-Nun | C07K 14/4713 |
|---|---|---|---|
| | | | 424/185.1 |
| 2004/0092716 A1* | 5/2004 | Ingraham | C07K 14/70567 |
| | | | 530/350 |

FOREIGN PATENT DOCUMENTS

WO   WO 1996-034622   11/1996

OTHER PUBLICATIONS

T Hart, et al., Modelling of multiple sclerosis: lessons learned in a non-human primate, Oct. 2004, Lancet Neurol vol. 3:588-597.*
Wekerle et al., Animal models of multiple sclerosis, 2006, Drug Discovery Today: Disease Models 3(4):359-367.*
Ransohoff, R. M., Animal models of multiple sclerosis: the good, the bad and the bottom line, Aug. 2012, Nature Neuroscience15(8):1074-1077.*
Behan et al., The sad plight of multiple sclerosis research (low on fact, high on fiction): critical data to support it being a neurocristopathy, 2010, Inflammopharmacology 18:265-290.*
Chen et al., Fusion Protein Linkers: Property, Design and Functionality, (Oct. 15, 2013), Adv Drug Deliv Rev. 2013 65(10):1357-1369. doi:10.1016/j.addr.2012.09.039.*
Baker et al., Critical appraisal of animal models of multiple sclerosis, (Jun. 2011), Multiple Sclerosis Journal 17(6):647-657.*
Varrin-Doyer, Michel, et al., "MOG transmembrane and cytoplasmic domains contain highly stimulatory T-cell epitopes in MS", Neurology: Neuroimmunology & Neuroinflammation, 2014; 1:e20; doi: 10.1212/NXI.000000000020.
Shetty, Aparna, et al., "Immunodominant T-Cell epitopes of MOG reside in its transmembrance and cytoplasmic domains in EAE", Neurology: Neuroimmunology & Neuroinflammation, 2014; 1:e22; doi: 10.1212/NXI.000000000022.
Wekerle et al., Ann. Neurol., 36: S47-S53 (1994).
Bischof et al., Proc. Natl. Acad. Sci. USA, 98: 12168 (2001).
Goverman et al., Lab Anim. Sci., 46: 482-92 (1996).
Office Action from the European Patent Office for European Patent No. EP16711090.6, dated Feb. 5, 2019, 5 pages.

* cited by examiner

Primary Examiner — John D Ulm
(74) Attorney, Agent, or Firm — Locke Lord LLP; Nicholas J. DiCeglie, Jr.

(57) ABSTRACT

Disclosed is a protein comprising no more than three human autoantigenic proteins, wherein a first human autoantigenic protein comprises a truncated myelin oligodendrocyte glycoprotein (MOG) amino acid sequence, a second human autoantigenic protein comprises a myelin basic protein (MBP) amino acid sequence, and a third human autoantigenic protein comprises a truncated proteolipid protein (PLP) amino acid sequence. Also disclosed are related nucleic acids, pharmaceutical compositions, methods of treating a demyelinating disease, and methods of producing the proteins.

6 Claims, 32 Drawing Sheets
Specification includes a Sequence Listing.

Red: MMPt treated for 20 hours
Blue: Normal saline treated for 20 hours

Red: MMPt treated for 20 hours
Blue: Normal saline treated for 20 hours

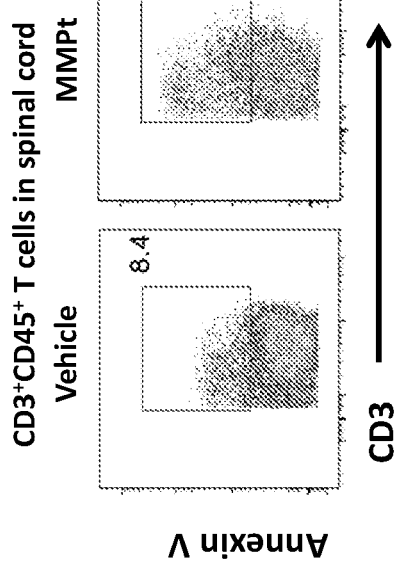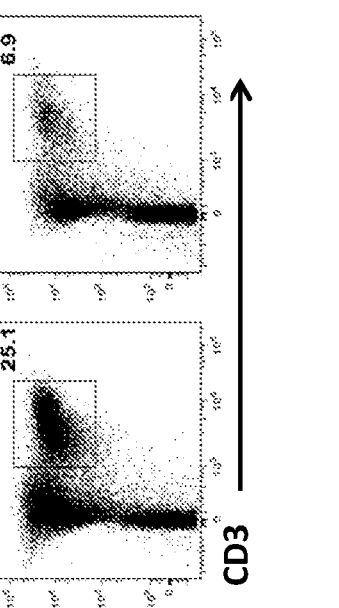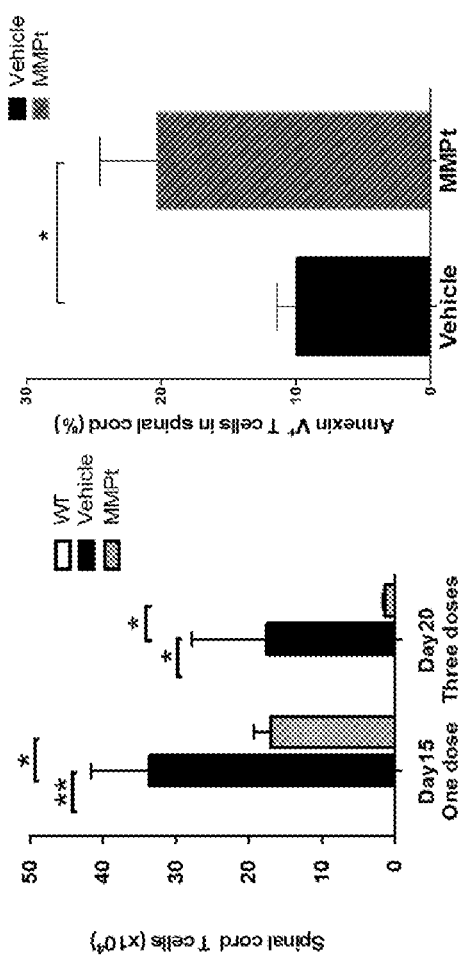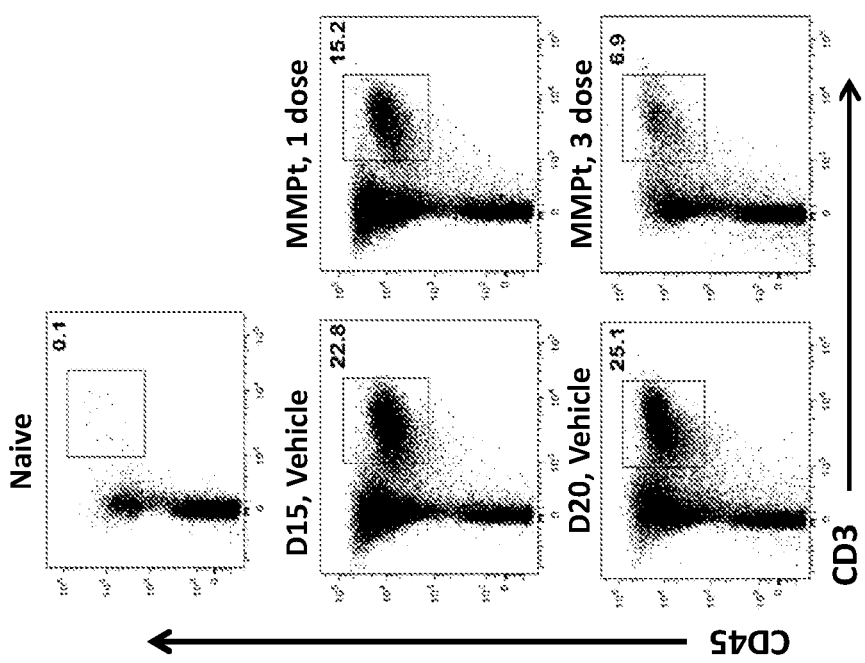
FIG. 20A
FIG. 20B
FIG. 20C
FIG. 20D

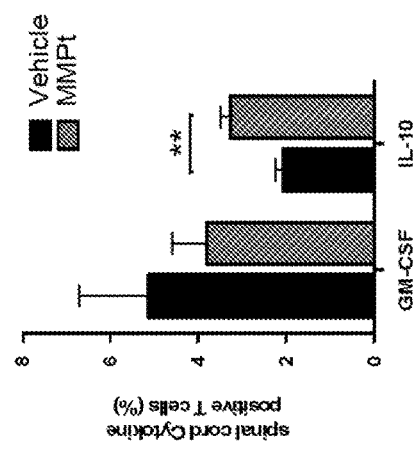
FIG. 25B
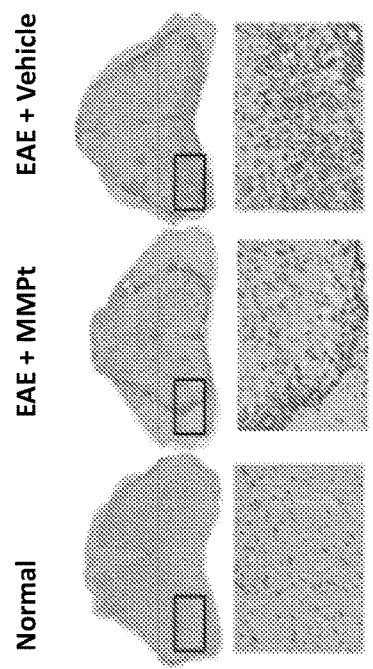
FIG 25D
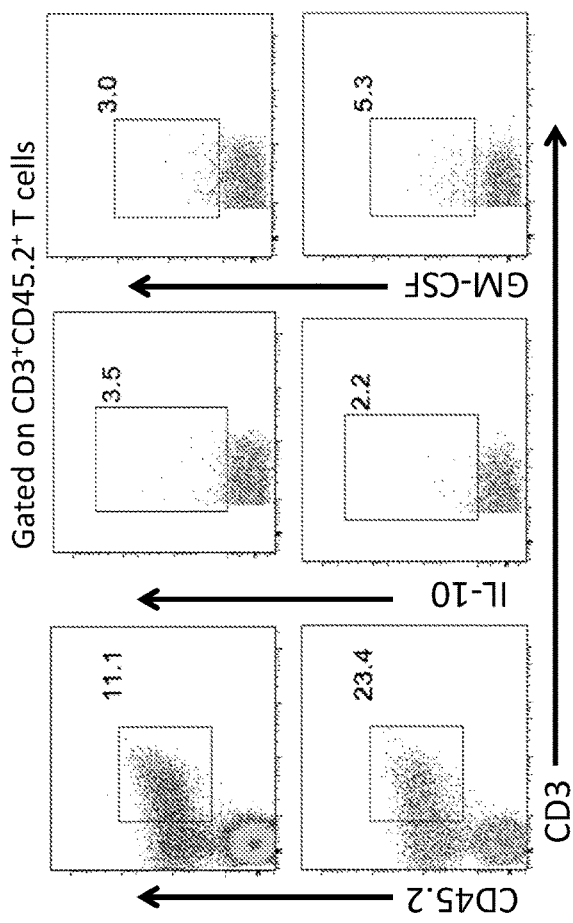
FIG. 25A
FIG. 25C
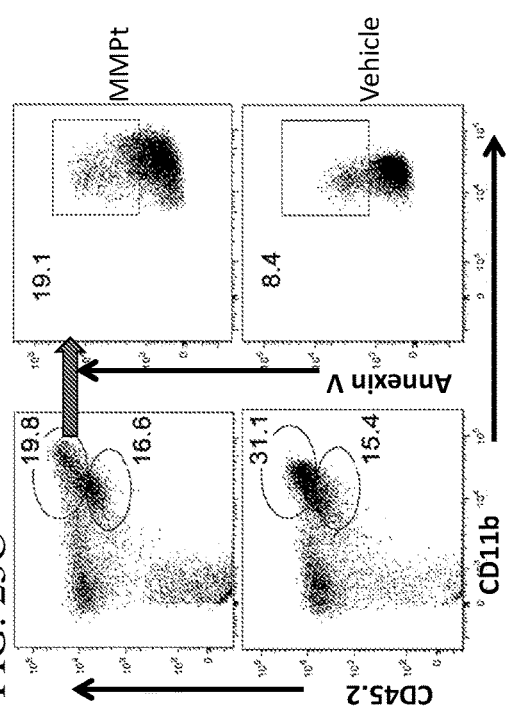

FIG. 29A

MOGΔ — GGGSGGG (SEQ ID NO: 5) — MBP — LGGLEDP (SEQ ID NO: 21) — PLPΔ — ENLYFQG (SEQ ID NO: 7) — 8xHis

FIG. 29B

SDS-PAGE

SEQUENCE LISTING

```
<160> NUMBER OF SEQ ID NOS: 32

<210> SEQ ID NO 1
<211> LENGTH: 122
<212> TYPE: PRT
<213> ORGANISM: Artificial Sequence
<220> FEATURE:
<223> OTHER INFORMATION: Synthetic

<400> SEQUENCE: 1

Met Gln Phe Arg Val Ile Gly Pro Arg His Pro Ile Arg Ala Leu Val
1               5                  10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala Pro Glu
    50                  55                  60

Tyr Arg Gly Arg Thr Glu Leu Leu Lys Asp Ala Ile Gly Glu Gly Lys
65                  70                  75                  80

Val Thr Leu Arg Ile Arg Asn Val Arg Phe Ser Asp Glu Gly Gly Phe
                85                  90                  95

Thr Cys Phe Phe Arg Asp His Ser Tyr Gln Glu Glu Ala Ala Met Glu
            100                 105                 110

Leu Lys Val Glu Asp Pro Phe Tyr Trp Val
        115                 120

<210> SEQ ID NO 2
<211> LENGTH: 198
<212> TYPE: PRT
<213> ORGANISM: Artificial Sequence
<220> FEATURE:
<223> OTHER INFORMATION: Synthetic

<400> SEQUENCE: 2

Asp Met Ala Ser His Lys Arg Pro Ser Gln Arg His Gly Ser Lys Tyr
1               5                  10                  15

Leu Ala Thr Ala Ser Thr Met Asp His Ala Arg His Gly Phe Leu Pro
            20                  25                  30

Arg His Arg Asp Thr Gly Ile Leu Asp Ser Ile Gly Arg Phe Phe Gly
        35                  40                  45

Gly Asp Arg Gly Ala Pro Lys Arg Gly Ser Gly Lys Val Pro Trp Leu
    50                  55                  60

Lys Pro Gly Arg Ser Pro Leu Pro Ser His Ala Arg Ser Gln Pro Gly
65                  70                  75                  80

Leu Cys Asn Met Tyr Lys Asp Ser His His Pro Ala Arg Thr Ala His
                85                  90                  95

Tyr Gly Ser Leu Pro Gln Lys Ser His Gly Arg Thr Gln Asp Glu Asn
            100                 105                 110

Pro Val Val His Phe Phe Lys Asn Ile Val Thr Pro Arg Thr Pro Pro
        115                 120                 125

Pro Ser Gln Gly Lys Gly Arg Gly Leu Ser Leu Ser Arg Phe Ser Trp
    130                 135                 140

Gly Ala Glu Gly Gln Arg Pro Gly Phe Gly Tyr Gly Gly Arg Ala Ser
```

```
                145                 150                 155                 160
Asp Tyr Lys Ser Ala His Lys Gly Phe Lys Gly Val Asp Ala Gln Gly
                        165                 170                 175

Thr Leu Ser Lys Ile Phe Lys Leu Gly Gly Arg Asp Ser Arg Ser Gly
                        180                 185                 190

Ser Pro Met Ala Arg Arg
                195

<210> SEQ ID NO 3
<211> LENGTH: 169
<212> TYPE: PRT
<213> ORGANISM: Artificial Sequence
<220> FEATURE:
<223> OTHER INFORMATION: Synthetic

<400> SEQUENCE: 3

Gly His Glu Ala Leu Thr Gly Thr Glu Lys Leu Ile Glu Thr Tyr Phe
1               5                   10                  15

Ser Lys Asn Tyr Gln Asp Tyr Glu Tyr Leu Ile Asn Val Ile His Ala
                20                  25                  30

Phe Gln Tyr Ala Glu Gly Phe Tyr Thr Thr Gly Ala Val Arg Gln Ile
                35                  40                  45

Phe Gly Asp Tyr Lys Thr Thr Ile Cys Gly Lys Gly Leu Ser Ala Thr
            50                  55                  60

Val Thr Gly Gly Gln Lys Gly Arg Gly Ser Arg Gly Gln His Gln Ala
65                  70                  75                  80

His Ser Leu Glu Arg Val Cys His Cys Leu Gly Lys Trp Leu Gly His
                85                  90                  95

Pro Asp Lys Phe Val Gly Ile Phe Asn Thr Trp Thr Thr Cys Gln Ser
                100                 105                 110

Ile Ala Phe Pro Ser Lys Thr Ser Ala Ser Ile Gly Ser Leu Cys Ala
            115                 120                 125

Asp Ala Arg Met Tyr Gly Val Leu Pro Trp Asn Ala Phe Pro Gly Lys
        130                 135                 140

Val Cys Gly Ser Asn Leu Leu Ser Ile Cys Lys Thr Ala Glu Phe Gln
145                 150                 155                 160

Met Thr Phe His Ala Ala Ala Leu Glu
                165

<210> SEQ ID NO 4
<211> LENGTH: 374
<212> TYPE: PRT
<213> ORGANISM: Artificial Sequence
<220> FEATURE:
<223> OTHER INFORMATION: Synthetic

<400> SEQUENCE: 4

Asp Met Ala Ser His Lys Arg Pro Ser Gln Arg His Gly Ser Lys Tyr
1               5                   10                  15

Leu Ala Thr Ala Ser Thr Met Asp His Ala Arg His Gly Phe Leu Pro
                20                  25                  30

Arg His Arg Asp Thr Gly Ile Leu Asp Ser Ile Gly Arg Phe Phe Gly
                35                  40                  45

Gly Asp Arg Gly Ala Pro Lys Arg Gly Ser Gly Lys Val Pro Trp Leu
            50                  55                  60

Lys Pro Gly Arg Ser Pro Leu Pro Ser His Ala Arg Ser Gln Pro Gly
65                  70                  75                  80
```

Leu Cys Asn Met Tyr Lys Asp Ser His His Pro Ala Arg Thr Ala His
            85                  90                  95

Tyr Gly Ser Leu Pro Gln Lys Ser His Gly Arg Thr Gln Asp Glu Asn
        100                 105                 110

Pro Val Val His Phe Phe Lys Asn Ile Val Thr Pro Arg Thr Pro Pro
        115                 120                 125

Pro Ser Gln Gly Lys Gly Arg Gly Leu Ser Leu Ser Arg Phe Ser Trp
    130                 135                 140

Gly Ala Glu Gly Gln Arg Pro Gly Phe Gly Tyr Gly Gly Arg Ala Ser
145                 150                 155                 160

Asp Tyr Lys Ser Ala His Lys Gly Phe Lys Gly Val Asp Ala Gln Gly
            165                 170                 175

Thr Leu Ser Lys Ile Phe Lys Leu Gly Gly Arg Asp Ser Arg Ser Gly
        180                 185                 190

Ser Pro Met Ala Arg Arg Leu Gly Gly Leu Glu Asp Pro Gly His Glu
    195                 200                 205

Ala Leu Thr Gly Thr Glu Lys Leu Ile Glu Thr Tyr Phe Ser Lys Asn
    210                 215                 220

Tyr Gln Asp Tyr Glu Tyr Leu Ile Asn Val Ile His Ala Phe Gln Tyr
225                 230                 235                 240

Ala Glu Gly Phe Tyr Thr Thr Gly Ala Val Arg Gln Ile Phe Gly Asp
            245                 250                 255

Tyr Lys Thr Thr Ile Cys Gly Lys Gly Leu Ser Ala Thr Val Thr Gly
        260                 265                 270

Gly Gln Lys Gly Arg Gly Ser Arg Gly Gln His Gln Ala His Ser Leu
    275                 280                 285

Glu Arg Val Cys His Cys Leu Gly Lys Trp Leu Gly His Pro Asp Lys
290                 295                 300

Phe Val Gly Ile Phe Asn Thr Trp Thr Thr Cys Gln Ser Ile Ala Phe
305                 310                 315                 320

Pro Ser Lys Thr Ser Ala Ser Ile Gly Ser Leu Cys Ala Asp Ala Arg
            325                 330                 335

Met Tyr Gly Val Leu Pro Trp Asn Ala Phe Pro Gly Lys Val Cys Gly
        340                 345                 350

Ser Asn Leu Leu Ser Ile Cys Lys Thr Ala Glu Phe Gln Met Thr Phe
    355                 360                 365

His Ala Ala Ala Leu Glu
    370

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gly Gly Gly Ser Gly Gly Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE

```
<222> LOCATION: (2)..(2)
<223> OTHER INFORMATION: Xaa at position 2 is any naturally occurring
      amino acid residue
<220> FEATURE:
<221> NAME/KEY: MISC_FEATURE
<222> LOCATION: (5)..(5)
<223> OTHER INFORMATION: Xaa at position 5 is any naturally occurring
      amino acid residue
<220> FEATURE:
<221> NAME/KEY: MISC_FEATURE
<222> LOCATION: (7)..(7)
<223> OTHER INFORMATION: Xaa at position 7 is any naturally occurring
      amino acid residue

<400> SEQUENCE: 6

Glu Xaa Leu Tyr Xaa Gln Xaa
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Glu Asn Leu Tyr Phe Gln Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

His His His His His His His His
1               5

<210> SEQ ID NO 9
<211> LENGTH: 503
<212> TYPE: PRT
<213> ORGANISM: Artificial Sequence
<220> FEATURE:
<223> OTHER INFORMATION: Synthetic

<400> SEQUENCE: 9

Met Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala Pro Glu
    50                  55                  60

Tyr Arg Gly Arg Thr Glu Leu Leu Lys Asp Ala Ile Gly Glu Gly Lys
65                  70                  75                  80

Val Thr Leu Arg Ile Arg Asn Val Arg Phe Ser Asp Glu Gly Gly Phe
                85                  90                  95

Thr Cys Phe Phe Arg Asp His Ser Tyr Gln Glu Glu Ala Ala Met Glu
            100                 105                 110

Leu Lys Val Glu Asp Pro Phe Tyr Trp Val Gly Gly Gly Ser Gly Gly
        115                 120                 125
```

Gly Asp Met Ala Ser His Lys Arg Pro Ser Gln Arg His Gly Ser Lys
130                 135                 140

Tyr Leu Ala Thr Ala Ser Thr Met Asp His Ala Arg His Gly Phe Leu
145                 150                 155                 160

Pro Arg His Arg Asp Thr Gly Ile Leu Asp Ser Ile Gly Arg Phe Phe
                165                 170                 175

Gly Gly Asp Arg Gly Ala Pro Lys Arg Gly Ser Gly Lys Val Pro Trp
                180                 185                 190

Leu Lys Pro Gly Arg Ser Pro Leu Pro Ser His Ala Arg Ser Gln Pro
            195                 200                 205

Gly Leu Cys Asn Met Tyr Lys Asp Ser His His Pro Ala Arg Thr Ala
210                 215                 220

His Tyr Gly Ser Leu Pro Gln Lys Ser His Gly Arg Thr Gln Asp Glu
225                 230                 235                 240

Asn Pro Val Val His Phe Lys Asn Ile Val Thr Pro Arg Thr Pro
                245                 250                 255

Pro Pro Ser Gln Gly Lys Gly Arg Gly Leu Ser Leu Ser Arg Phe Ser
            260                 265                 270

Trp Gly Ala Glu Gly Gln Arg Pro Gly Phe Gly Tyr Gly Gly Arg Ala
            275                 280                 285

Ser Asp Tyr Lys Ser Ala His Lys Gly Phe Lys Gly Val Asp Ala Gln
290                 295                 300

Gly Thr Leu Ser Lys Ile Phe Lys Leu Gly Gly Arg Asp Ser Arg Ser
305                 310                 315                 320

Gly Ser Pro Met Ala Arg Arg Leu Gly Gly Leu Glu Asp Pro Gly His
                325                 330                 335

Glu Ala Leu Thr Gly Thr Glu Lys Leu Ile Glu Thr Tyr Phe Ser Lys
                340                 345                 350

Asn Tyr Gln Asp Tyr Glu Tyr Leu Ile Asn Val Ile His Ala Phe Gln
            355                 360                 365

Tyr Ala Glu Gly Phe Tyr Thr Thr Gly Ala Val Arg Gln Ile Phe Gly
        370                 375                 380

Asp Tyr Lys Thr Thr Ile Cys Gly Lys Gly Leu Ser Ala Thr Val Thr
385                 390                 395                 400

Gly Gly Gln Lys Gly Arg Gly Ser Arg Gly Gln His Gln Ala His Ser
                405                 410                 415

Leu Glu Arg Val Cys His Cys Leu Gly Lys Trp Leu Gly His Pro Asp
            420                 425                 430

Lys Phe Val Gly Ile Phe Asn Thr Trp Thr Thr Cys Gln Ser Ile Ala
        435                 440                 445

Phe Pro Ser Lys Thr Ser Ala Ser Ile Gly Ser Leu Cys Ala Asp Ala
450                 455                 460

Arg Met Tyr Gly Val Leu Pro Trp Asn Ala Phe Pro Gly Lys Val Cys
465                 470                 475                 480

Gly Ser Asn Leu Leu Ser Ile Cys Lys Thr Ala Glu Phe Gln Met Thr
                485                 490                 495

Phe His Ala Ala Ala Leu Glu
            500

<210> SEQ ID NO 10
<211> LENGTH: 518
<212> TYPE: PRT
<213> ORGANISM: Artificial Sequence
<220> FEATURE:
<223> OTHER INFORMATION: Synthetic

<400> SEQUENCE: 10

```
Met Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala Pro Glu
    50                  55                  60

Tyr Arg Gly Arg Thr Glu Leu Leu Lys Asp Ala Ile Gly Glu Gly Lys
65                  70                  75                  80

Val Thr Leu Arg Ile Arg Asn Val Arg Phe Ser Asp Glu Gly Gly Phe
                85                  90                  95

Thr Cys Phe Phe Arg Asp His Ser Tyr Gln Glu Ala Ala Met Glu
            100                 105                 110

Leu Lys Val Glu Asp Pro Phe Tyr Trp Val Gly Gly Ser Gly Gly
            115                 120                 125

Gly Asp Met Ala Ser His Lys Arg Pro Ser Gln Arg His Gly Ser Lys
    130                 135                 140

Tyr Leu Ala Thr Ala Ser Thr Met Asp His Ala Arg His Gly Phe Leu
145                 150                 155                 160

Pro Arg His Arg Asp Thr Gly Ile Leu Asp Ser Ile Gly Arg Phe Phe
                165                 170                 175

Gly Gly Asp Arg Gly Ala Pro Lys Arg Gly Ser Gly Lys Val Pro Trp
            180                 185                 190

Leu Lys Pro Gly Arg Ser Pro Leu Pro Ser His Ala Arg Ser Gln Pro
            195                 200                 205

Gly Leu Cys Asn Met Tyr Lys Asp Ser His His Pro Ala Arg Thr Ala
    210                 215                 220

His Tyr Gly Ser Leu Pro Gln Lys Ser His Gly Arg Thr Gln Asp Glu
225                 230                 235                 240

Asn Pro Val Val His Phe Phe Lys Asn Ile Val Thr Pro Arg Thr Pro
                245                 250                 255

Pro Pro Ser Gln Gly Lys Gly Arg Gly Leu Ser Leu Ser Arg Phe Ser
            260                 265                 270

Trp Gly Ala Glu Gly Gln Arg Pro Gly Phe Gly Tyr Gly Gly Arg Ala
            275                 280                 285

Ser Asp Tyr Lys Ser Ala His Lys Gly Phe Lys Gly Val Asp Ala Gln
    290                 295                 300

Gly Thr Leu Ser Lys Ile Phe Lys Leu Gly Gly Arg Asp Ser Arg Ser
305                 310                 315                 320

Gly Ser Pro Met Ala Arg Arg Leu Gly Leu Glu Asp Pro Gly His
            325                 330                 335

Glu Ala Leu Thr Gly Thr Glu Lys Leu Ile Glu Thr Tyr Phe Ser Lys
            340                 345                 350

Asn Tyr Gln Asp Tyr Glu Tyr Leu Ile Asn Val Ile His Ala Phe Gln
    355                 360                 365

Tyr Ala Glu Gly Phe Tyr Thr Thr Gly Ala Val Arg Gln Ile Phe Gly
    370                 375                 380

Asp Tyr Lys Thr Thr Ile Cys Gly Lys Gly Leu Ser Ala Thr Val Thr
385                 390                 395                 400

Gly Gly Gln Lys Gly Arg Gly Ser Arg Gly Gln His Gln Ala His Ser
```

```
                    405                 410                 415
Leu Glu Arg Val Cys His Cys Leu Gly Lys Trp Leu Gly His Pro Asp
            420                 425                 430

Lys Phe Val Gly Ile Phe Asn Thr Trp Thr Thr Cys Gln Ser Ile Ala
        435                 440                 445

Phe Pro Ser Lys Thr Ser Ala Ser Ile Gly Ser Leu Cys Ala Asp Ala
    450                 455                 460

Arg Met Tyr Gly Val Leu Pro Trp Asn Ala Phe Pro Gly Lys Val Cys
465                 470                 475                 480

Gly Ser Asn Leu Leu Ser Ile Cys Lys Thr Ala Glu Phe Gln Met Thr
                485                 490                 495

Phe His Ala Ala Ala Leu Glu Glu Asn Leu Tyr Phe Gln Gly His His
            500                 505                 510

His His His His His His
        515

<210> SEQ ID NO 11
<211> LENGTH: 366
<212> TYPE: DNA
<213> ORGANISM: Artificial Sequence
<220> FEATURE:
<223> OTHER INFORMATION: Synthetic

<400> SEQUENCE: 11
atgcagtttc gcgtgattgg cccgcgccat ccgattcgcg cgctggtggg cgatgaagtg      60
gaactgccgt gccgcattag cccgggcaaa aacgcgaccg gcatggaagt gggctggtat     120
cgcccgccgt ttagccgcgt ggtgcatctg tatcgcaacg gcaaagatca ggatggcgat     180
caggcgccgg aatatcgcgg ccgcaccgaa ctgctgaaag atgcgattgg cgaaggcaaa     240
gtgaccctgc gcattcgcaa cgtgcgcttt agcgatgaag gcggctttac ctgcttttt      300 cgcgatcata gctatcagga gaagcggcg atggaactga agtggaaga tccgttttat      360 tgggtg                                                               366

<210> SEQ ID NO 12
<211> LENGTH: 594
<212> TYPE: DNA
<213> ORGANISM: Artificial Sequence
<220> FEATURE:
<223> OTHER INFORMATION: Synthetic

<400> SEQUENCE: 12
gatatggcga gccataaacg cccgagccag cgccatggca gcaaatatct ggcgaccgcg      60
agcaccatgg atcatgcgcg ccatggctt ctgccgcgcc atcgcgatac cggcattctg     120
gatagcattg gccgcttttt tggcggcgat cgcggcgcgc cgaaacgcgg cagcggcaaa     180
gtgccgtggc tgaaaccggg ccgcagcccg ctgccgagcc atgcgcgcag ccagccgggc     240
ctgtgcaaca tgtataaaga tagccatcat ccggcgcgca ccgcgcatta tggcagcctg     300
ccgcagaaaa gccatggccg cacccaggat gaaaacccgg tggtgcattt ttttaaaaac     360
attgtgaccc cgcgcacccc gccgccgagc cagggcaaag ccgcggcct gagcctgagc      420 cgctttagct ggggcgcgga aggccagcgc ccgggctttg gctatggcgg ccgcgcgagc     480
gattataaaa gcgcgcataa aggctttaaa ggcgtggatg cgcagggcac cctgagcaaa     540 attttaaac tgggcggccg cgatagccgc agcggcagcc gatggcgcg ccgc            594

<210> SEQ ID NO 13
```

<211> LENGTH: 507
<212> TYPE: DNA
<213> ORGANISM: Artificial Sequence
<220> FEATURE:
<223> OTHER INFORMATION: Synthetic

<400> SEQUENCE: 13

| | | | | | |
|---|---|---|---|---|---|
| ggccatgaag | cgctgaccgg | caccgaaaaa | ctgattgaaa | cctatttag | caaaaactat | 60 |
| caggattatg | aatatctgat | taacgtgatt | catgcgtttc | agtatgcgga | aggctttat | 120 |
| accaccggcg | cggtgcgcca | gattttggc | gattataaaa | ccaccatttg | cggcaaaggc | 180 |
| ctgagcgcga | ccgtgaccgg | cggccagaaa | ggccgcggca | ccgcggcca | gcatcaggcg | 240 |
| catagcctgg | aacgcgtgtg | ccattgcctg | ggcaaatggc | tgggccatcc | ggataaattt | 300 |
| gtgggcattt | ttaacacctg | gaccacctgc | cagagcattg | cgtttccgag | caaaaccagc | 360 |
| gcgagcattg | gcagcctgtg | cgcggatgcg | cgcatgtatg | cgtgctgcc | gtggaacgcg | 420 |
| tttccgggca | agtgtgcgg | cagcaacctg | ctgagcattt | gcaaaaccgc | ggaatttcag | 480 |
| atgacctttc | atgcggcggc | gctggaa | | | 507 |

<210> SEQ ID NO 14
<211> LENGTH: 1122
<212> TYPE: DNA
<213> ORGANISM: Artificial Sequence
<220> FEATURE:
<223> OTHER INFORMATION: Synthetic

<400> SEQUENCE: 14

| | | | | | |
|---|---|---|---|---|---|
| gatatggcga | gccataaacg | cccgagccag | cgccatggca | gcaaatatct | ggcgaccgcg | 60 |
| agcaccatgg | atcatgcgcg | ccatggctt | ctgccgcgcc | atcgcgatac | cggcattctg | 120 |
| gatagcattg | gccgcttttt | tggcggcgat | cgcggcgcgc | cgaaacgcgg | cagcggcaaa | 180 |
| gtgccgtggc | tgaaaccggg | ccgcagcccg | ctgccgagcc | atgcgcgcag | ccagccgggc | 240 |
| ctgtgcaaca | tgtataaaga | tagccatcat | ccggcgcgca | ccgcgcatta | tggcagcctg | 300 |
| ccgcagaaaa | gccatggccg | cacccaggat | gaaaacccgg | tggtgcattt | ttttaaaaac | 360 |
| attgtgaccc | cgcgcacccc | gccgccgagc | cagggcaaag | gccgcggcct | gagcctgagc | 420 |
| cgctttagct | ggggcgcgga | aggccagcgc | ccgggctttg | gctatggcgg | ccgcgcgagc | 480 |
| gattataaaa | gcgcgcataa | aggctttaaa | ggcgtggatg | cgcagggcac | cctgagcaaa | 540 |
| attttaaac | tgggcggccg | cgatagccgc | agcggcagcc | cgatggcgcg | ccgcctgggc | 600 |
| ggcctggaag | atccgggcca | tgaagcgctg | accggcaccg | aaaaactgat | tgaaacctat | 660 |
| tttagcaaaa | actatcagga | ttatgaatat | ctgattaacg | tgattcatgc | gtttcagtat | 720 |
| gcggaaggct | tttataccac | cggcgcggtg | cgccagattt | ttggcgatta | taaaaccacc | 780 |
| atttgcggca | aaggcctgag | cgcgaccgtg | accggcggcc | agaaaggccg | cggcagccgc | 840 |
| ggccagcatc | aggcgcatag | cctggaacgc | gtgtgccatt | gcctgggcaa | atggctgggc | 900 |
| catccggata | aatttgtggg | catttttaac | acctggacca | cctgccagag | cattgcgttt | 960 |
| ccgagcaaaa | ccagcgcgag | cattggcagc | ctgtgcgcgg | atgcgcgcat | gtatggcgtg | 1020 |
| ctgccgtgga | acgcgtttcc | gggcaaagtg | tgcggcagca | acctgctgag | catttgcaaa | 1080 |
| accgcggaat | tcagatgac | ctttcatgcg | gcggcgctgg | aa | 1122 |

<210> SEQ ID NO 15
<211> LENGTH: 21
<212> TYPE: DNA
<213> ORGANISM: Artificial Sequence -continued

```
<220> FEATURE:
<223> OTHER INFORMATION: Synthetic

<400> SEQUENCE: 15
ggtggtggtt ccggtggtgg t                                        21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
gaaaacttgt acttccaggg c                                        21

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
caccaccacc accaccacca ccac                                     24

<210> SEQ ID NO 18
<211> LENGTH: 1554
<212> TYPE: DNA
<213> ORGANISM: Artificial Sequence
<220> FEATURE:
<223> OTHER INFORMATION: Synthetic

<400> SEQUENCE: 18
atgcagtttc gcgtgattgg cccgcgccat ccgattcgcg cgctggtggg cgatgaagtg      60
gaactgccgt gccgcattag cccgggcaaa aacgcgaccg gcatggaagt gggctggtat     120
cgcccgccgt ttagccgcgt ggtgcatctg tatcgcaacg gcaaagatca ggatggcgat     180
caggcgccgg aatatcgcgg ccgcaccgaa ctgctgaaag atgcgattgg cgaaggcaaa     240
gtgaccctgc gcattcgcaa cgtgcgcttt agcgatgaag gcggctttac ctgcttttt     300 cgcgatcata gctatcagga agaagcggcg atggaactga agtggaaga tccgttttat     360 tgggtgggtg gtggttccgg tggtggtgat atggcgagcc ataaacgccc gagccagcgc    420
catggcagca aatatctggc gaccgcgagc accatggatc atgcgcgcca tggctttctg    480
ccgcgccatc gcgataccgg cattctggat agcattggcc gcttttttgg cggcgatcgc    540
ggcgcgccga aacgcggcag cggcaaagtg ccgtggctga accgggccg cagcccgctg     600 ccgagccatg cgcgcagcca gccgggcctg tgcaacatgt ataaagatag ccatcatccg    660
gcgcgcaccg cgcattatgg cagcctgccg cagaaaagcc atggccgcac caggatgaa     720 aacccggtgg tgcattttt taaaaacatt gtgaccccgc gcaccccgcc gccgagccag    780
ggcaaaggcc gcggcctgag cctgagccgc tttagctggg gcgcggaagg ccagcgcccg    840
ggctttggct atggcggccg cgcgagcgat tataaaagcg cgcataaagg ctttaaaggc    900
gtggatgcgc agggcaccct gagcaaaatt tttaaactgg cggccgcga tagccgcagc    960 ggcagcccga tggcgcgccg cctgggcggc ctggaagatc cgggccatga agcgctgacc   1020
ggcaccgaaa aactgattga aacctatttt agcaaaaact atcaggatta tgaatatctg   1080
attaacgtga ttcatgcgtt tcagtatgcg gaaggctttt ataccaccgg cgcggtgcgc   1140
```

```
cagattttg gcgattataa aaccaccatt tgcggcaaag gcctgagcgc gaccgtgacc    1200
ggcggccaga aaggccgcgg cagccgcggc cagcatcagg cgcatagcct ggaacgcgtg    1260
tgccattgcc tgggcaaatg gctgggccat ccggataaat ttgtgggcat ttttaacacc    1320
tggaccacct gccagagcat tgcgtttccg agcaaaacca gcgcgagcat ggcagcctg     1380 tgcgcggatg cgcgcatgta tggcgtgctg ccgtggaacg cgtttccggg caaagtgtgc    1440
ggcagcaacc tgctgagcat ttgcaaaacc gcggaatttc agatgacctt tcatgcggcg    1500
gcgctggaag aaaacttgta cttccagggc caccaccacc accaccacca ccac          1554
```

<210> SEQ ID NO 19
<211> LENGTH: 509
<212> TYPE: PRT
<213> ORGANISM: Artificial Sequence
<220> FEATURE:
<223> OTHER INFORMATION: Synthetic

<400> SEQUENCE: 19

```
Met Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala Pro Glu
    50                  55                  60

Tyr Arg Gly Arg Thr Glu Leu Leu Lys Asp Ala Ile Gly Glu Gly Lys
65                  70                  75                  80

Val Thr Leu Arg Ile Arg Asn Val Arg Phe Ser Asp Glu Gly Gly Phe
                85                  90                  95

Thr Cys Phe Phe Arg Asp His Ser Tyr Gln Glu Ala Ala Met Glu
            100                 105                 110

Leu Lys Val Glu Asp Pro Phe Tyr Trp Val Gly Gly Ser Gly Gly
            115                 120                 125

Gly Asp Met Ala Ser His Lys Arg Pro Ser Gln Arg His Gly Ser Lys
    130                 135                 140

Tyr Leu Ala Thr Ala Ser Thr Met Asp His Ala Arg His Gly Phe Leu
145                 150                 155                 160

Pro Arg His Arg Asp Thr Gly Ile Leu Asp Ser Ile Gly Arg Phe Phe
                165                 170                 175

Gly Gly Asp Arg Gly Ala Pro Lys Arg Gly Ser Gly Lys Val Pro Trp
            180                 185                 190

Leu Lys Pro Gly Arg Ser Pro Leu Pro Ser His Ala Arg Ser Gln Pro
        195                 200                 205

Gly Leu Cys Asn Met Tyr Lys Asp Ser His His Pro Ala Arg Thr Ala
    210                 215                 220

His Tyr Gly Ser Leu Pro Gln Lys Ser His Gly Arg Thr Gln Asp Glu
225                 230                 235                 240

Asn Pro Val Val His Phe Phe Lys Asn Ile Val Thr Pro Arg Thr Pro
                245                 250                 255

Pro Pro Ser Gln Gly Lys Gly Arg Gly Leu Ser Leu Ser Arg Phe Ser
            260                 265                 270

Trp Gly Ala Glu Gly Gln Arg Pro Gly Phe Tyr Gly Gly Arg Ala
        275                 280                 285

Ser Asp Tyr Lys Ser Ala His Lys Gly Phe Lys Gly Val Asp Ala Gln
```

```
                290                 295                 300
Gly Thr Leu Ser Lys Ile Phe Lys Leu Gly Gly Arg Asp Ser Arg Ser
305                 310                 315                 320

Gly Ser Pro Met Ala Arg Arg Leu Gly Gly Leu Glu Asp Pro Gly His
                325                 330                 335

Glu Ala Leu Thr Gly Thr Glu Lys Leu Ile Glu Thr Tyr Phe Ser Lys
                340                 345                 350

Asn Tyr Gln Asp Tyr Glu Tyr Leu Ile Asn Val Ile His Ala Phe Gln
                355                 360                 365

Tyr Ala Glu Gly Phe Tyr Thr Thr Gly Ala Val Arg Gln Ile Phe Gly
                370                 375                 380

Asp Tyr Lys Thr Thr Ile Cys Gly Lys Gly Leu Ser Ala Thr Val Thr
385                 390                 395                 400

Gly Gly Gln Lys Gly Arg Gly Ser Arg Gly Gln His Gln Ala His Ser
                405                 410                 415

Leu Glu Arg Val Cys His Cys Leu Gly Lys Trp Leu Gly His Pro Asp
                420                 425                 430

Lys Phe Val Gly Ile Phe Asn Thr Trp Thr Thr Cys Gln Ser Ile Ala
                435                 440                 445

Phe Pro Ser Lys Thr Ser Ala Ser Ile Gly Ser Leu Cys Ala Asp Ala
                450                 455                 460

Arg Met Tyr Gly Val Leu Pro Trp Asn Ala Phe Pro Gly Lys Val Cys
465                 470                 475                 480

Gly Ser Asn Leu Leu Ser Ile Cys Lys Thr Ala Glu Phe Gln Met Thr
                485                 490                 495

Phe His Ala Ala Ala Leu Glu Glu Asn Leu Tyr Phe Gln
                500                 505

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Glu Asn Leu Tyr Phe Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21

Leu Gly Gly Leu Glu Asp Pro
1               5

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ctgggcggcc tggaagatcc g                                           21
```

<210> SEQ ID NO 23
<211> LENGTH: 1920
<212> TYPE: DNA
<213> ORGANISM: Artificial Sequence
<220> FEATURE:
<223> OTHER INFORMATION: Synthetic

<400> SEQUENCE: 23

| | | | | | |
|---|---|---|---|---|---|
| gtcatcccct | cagtctgtag | cccttttgtg | tgagtgcctg | gcaagggtga | cgtggggctg | 60 |
| tttctgcggg | cacagctgca | gcaattaccg | gagtggaggc | agggcccagg | cagcactgcc | 120 |
| ctccaagatc | ttcccttggg | cttttcagca | gtaaggggac | atgcacccca | agggcctcca | 180 |
| cttggcctga | ccttgctgcg | ggggctctct | gtccccagga | acagtagaga | tggcaagctt | 240 |
| atcaagaccc | tctctgccca | gctgcctctg | ctccttcctc | ctcctcctcc | tcctccaagt | 300 |
| gtcttccagc | tatgcagggc | agttcagagt | gataggacca | agacacccta | tccgggctct | 360 |
| ggtcggggat | gaagtggaat | tgccatgtcg | catatctcct | gggaagaacg | ctacaggcat | 420 |
| ggaggtgggg | tggtaccgcc | ccccttctc | tagggtggtt | catctctaca | gaaatggcaa | 480 |
| ggaccaagat | ggagaccagg | cacctgaata | tcggggccgg | acagagctgc | tgaaagatgc | 540 |
| tattggtgag | ggaaaggtga | ctctcaggat | ccggaatgta | aggttctcag | atgaaggagg | 600 |
| tttcacctgc | ttcttccgag | atcattctta | ccaagaggag | gcagcaatgg | aattgaaagt | 660 |
| agaagatcct | ttctactggg | tgagccctgg | agtgctggtc | ctcctcgcgg | tgctgcctgt | 720 |
| gctcctcctg | cagatcactg | ttggcctcat | cttcctctgc | ctgcagtaca | gactgagagg | 780 |
| aaaacttcga | gcagagatag | agaatctcca | ccggactttt | gatccccact | ttctgagggt | 840 |
| gcccctgctgg | aagataaccc | tgtttgtaat | tgtgccggtt | cttggaccct | tggttgcctt | 900 |
| gatcatctgc | tacaactggc | tacatcgaag | actagcaggg | caattccttg | aagagctact | 960 |
| cttccacctg | gaagccctct | ctggctaagg | acaggcaggt | gccctctct | ccatcagagg | 1020 |
| acacctgtac | tggagagcaa | cacaggatgg | tctctgccat | gaactggagg | ccaggaatct | 1080 |
| cctcactgaa | aattacagta | tggtaacttt | gcaaatggtg | gttgtttctt | ccaagactcc | 1140 |
| agccctgatt | gcgcaaaact | gaaaggcatg | tgaagggaag | gaagaggaag | agtgcaaaac | 1200 |
| attgaagaga | gagctgagtg | agctgaagag | tgaggatatg | agtagcccca | acccaaacct | 1260 |
| ggagatgggg | agaaacctac | agaatactag | ccagagctcc | tccttgtctt | ggcagcctac | 1320 |
| tagggacctg | gggaagcaaa | acgaaagct | gggcaacatg | cctgctttag | aatgttttcc | 1380 |
| ttctacttac | acatcttcca | caggtctcag | aatctttcct | tcctctcatc | cttttctcct | 1440 |
| atcttcatat | ctatcagagt | atccactgtt | tattcaacaa | ctactacttg | atggtcagac | 1500 |
| acaaacaaac | aagctaggtg | ctaattaata | aagatacgag | ttttggccgg | gtgcggtggc | 1560 |
| tcacgcctgt | aatcccagca | ctttgggagg | ccgaggcggg | cgaatcacga | ggtcaggagt | 1620 |
| tcaagaccag | cctggccaac | atggtgaaac | cccatctcta | ctaaaaatac | aaacaattaa | 1680 |
| ctgagcatag | tggtgggcac | ctataatacc | agctactccg | gaggctgagg | caggagaatc | 1740 |
| gcttgaaccc | aggaggcaga | ggttgcagtg | agctgagatc | gtgccactgc | actctagccg | 1800 |
| gagtgacaga | gtaagactct | gtctcaaaaa | taaataaata | aataaataaa | taataaata | 1860 |
| aataaataaa | taaaaaataa | taatacaagt | tttcataagc | acacttctaa | aaaaaaaaaa | 1920 |

<210> SEQ ID NO 24
<211> LENGTH: 252
<212> TYPE: PRT
<213> ORGANISM: Homo sapiens

<400> SEQUENCE: 24

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Val Leu Val Leu Leu Ala
145                 150                 155                 160

Val Leu Pro Val Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
                180                 185                 190

Leu His Arg Thr Phe Asp Pro His Phe Leu Arg Val Pro Cys Trp Lys
            195                 200                 205

Ile Thr Leu Phe Val Ile Val Pro Val Leu Gly Pro Leu Val Ala Leu
        210                 215                 220

Ile Ile Cys Tyr Asn Trp Leu His Arg Arg Leu Ala Gly Gln Phe Leu
225                 230                 235                 240

Glu Glu Leu Leu Phe His Leu Glu Ala Leu Ser Gly
                245                 250

<210> SEQ ID NO 25
<211> LENGTH: 122
<212> TYPE: PRT
<213> ORGANISM: Homo sapiens

<400> SEQUENCE: 25

Met Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro His Phe Ser Arg Val Val
        35                  40                  45

His Leu Tyr Arg Asn Gly Lys Asp Gln Asp Gly Asp Gln Ala Pro Glu
    50                  55                  60

Tyr Arg Gly Arg Thr Glu Leu Leu Lys Asp Ala Ile Gly Glu Gly Lys
65                  70                  75                  80

Val Thr Leu Arg Ile Arg Asn Val Arg Phe Ser Asp Glu Gly Gly Phe
                85                  90                  95

Thr Cys Phe Phe Arg Asp His Ser Tyr Gln Glu Glu Ala Ala Met Glu
            100                 105                 110

Leu Lys Val Glu Asp Pro Phe Tyr Trp Val
        115                 120

<210> SEQ ID NO 26
<211> LENGTH: 2794
<212> TYPE: DNA
<213> ORGANISM: Artificial Sequence
<220> FEATURE:
<223> OTHER INFORMATION: Synthetic

<400> SEQUENCE: 26

| | | | | | |
|---|---|---|---|---|---|
| tgggtgcgcg | cccgtccctc | ggagccgccg | ccgtcagtca | ccgccgccgc | gcgccagaga | 60 |
| gaagcagcct | ccggccccgg | cggcccctgt | ctcccgaccc | cggaaggcga | agcaggctgc | 120 |
| ccggggaccc | cgcgcgtggg | cgcttgaagc | cgagaccagc | ctgccgggc | ctgggcaggc | 180 |
| ggagcagggc | cttggacccc | gcggcgcccc | tcggcctcgg | agcaacgagc | gcagcgccgc | 240 |
| ctctgaagag | ccaatccatt | caggatggga | aaccacgcag | gcaaacgaga | attaaatgcc | 300 |
| gagaaggcca | gtacgaatag | tgaaactaac | agaggagaat | ctgaaaaaaa | gagaaacctg | 360 |
| ggtgaacttt | cacggacaac | ctcagaggac | aacgaagtgt | tcggagaggc | agatgcgaac | 420 |
| cagaacaatg | gaacctcctc | tcaggacaca | gcggtgactg | actccaagcg | cacagcggac | 480 |
| ccgaagaatg | cctggcagga | tgcccaccca | gctgacccag | ggagccgccc | ccacttgatc | 540 |
| cgcctctttt | cccgagatgc | cccggggagg | gaggacaaca | ccttcaaaga | caggccctct | 600 |
| gagtccgacg | agctccagac | catccaagaa | gacagtgcag | ccacctccga | gagcctggat | 660 |
| gtgatggcgt | cacagaagag | accctcccag | aggcacggat | ccaagtacct | ggccacagca | 720 |
| agtaccatgg | accatgccag | gcatggcttc | ctcccaaggc | acagagacac | gggcatcctt | 780 |
| gactccatcg | ggcgcttctt | tggcggtgac | aggggtgcgc | ccaagcgggg | ctctggcaag | 840 |
| gactcacacc | acccggcaag | aactgctcac | tacggctccc | tgccccagaa | gtcacacggc | 900 |
| cggacccaag | atgaaaaccc | cgtagtccac | ttcttcaaga | acattgtgac | gcctcgcaca | 960 |
| ccaccccgt | cgcagggaaa | ggggagagga | ctgtccctga | gcagatttag | ctgggggggcc | 1020 |
| gaaggccaga | gaccaggatt | tggctacgga | ggcagagcgt | ccgactataa | atcggctcac | 1080 |
| aagggattca | agggagtcga | tgcccagggc | acgctttcca | aaattttaa | gctgggagga | 1140 |
| agagatagtc | gctctggatc | acccatggct | agacgctgaa | aacccacctg | gttccggaat | 1200 |
| cctgtcctca | gcttcttaat | ataactgcct | taaaacttta | atcccacttg | ccctgttac | 1260 |
| ctaattagag | cagatgaccc | ctcccctaat | gcctgcggag | ttgtgcacgt | agtagggtca | 1320 |
| ggccacggca | gcctaccggc | aatttccggc | caacagttaa | atgagaacat | gaaaacagaa | 1380 |
| aacggttaaa | actgtcccctt | tctgtgtgaa | gatcacgttc | cttccccgc | aatgtgcccc | 1440 |
| cagacgcacg | tgggtcttca | gggggccagg | tgcacagacg | tccctccacg | ttcaccccctc | 1500 |
| caccccttgga | ctttcttttc | gccgtggctg | cggcacccctt | gcgcttttgc | tggtcactgc | 1560 |
| catggaggca | cacagctgca | gagacagaga | ggacgtgggc | ggcagagagg | actgttgaca | 1620 |
| tccaagcttc | ctttgttttt | ttttcctgtc | cttctctcac | ctcctaaagt | agacttcatt | 1680 |
| tttcctaaca | ggattagaca | gtcaaggagt | ggcttactac | atgtgggagc | ttttggtatg | 1740 |
| tgacatgcgg | gctgggcagc | tgttagagtc | caacgtgggg | cagcacagag | aggggggccac | 1800 |
| ctccccagge | cgtggctgcc | cacacacccc | aattagctga | attcgcgtgt | ggcagaggga | 1860 |
| ggaaaaggag | gcaaacgtgg | gctgggcaat | ggcctcacat | aggaaacagg | gtcttcctgg | 1920 |
| agatttggtg | atggagatgt | caagcaggtg | gcctctggac | gtcaccgttg | ccctgcatgg | 1980 |

```
tggcccaga gcagcctcta tgaacaacct cgtttccaaa ccacagccca cagccggaga    2040
gtccaggaag acttgcgcac tcagagcaga agggtaggag tcctctagac agcctcgcag    2100
ccgcgccagt cgcccataga cactggctgt gaccgggcgt gctggcagcg cagtgcaca    2160 gtggccagca ctaaccctcc ctgagaagat aaccggctca ttcacttcct cccagaagac    2220
gcgtggtagc gagtaggcac aggcgtgcac ctgctcccga attactcacc gagacacacg    2280
ggctgagcag acggccccgt ggatgggagac aaagagctct tctgaccata tccttcttaa    2340
cacccgctgg catctccttt cgcgcctccc tccctaacct actgacccac cttttgattt    2400
tagcgcacct gtgattgata ggccttccaa agagtcccac gctggcatca ccctccccga    2460
ggacggagat gaggagtagt cagcgtgatg ccaaaacgcg tcttcttaat ccaattctaa    2520
ttctgaatgt ttcgtgtggg cttaatacca tgtctattaa tatatagcct cgatgatgag    2580
agagttacaa agaacaaaac tccagacaca aacctccaaa tttttcagca gaagcactct    2640
gcgtcgctga gctgaggtcg gctctgcgat ccatacgtgg ccgcacccac acagcacgtg    2700
ctgtgacgat ggctgaacgg aaagtgtaca ctgttcctga atattgaaat aaaacaataa    2760
acttttaatg gtaaaaaaaa aaaaaaaaaa aaaa                                2794

<210> SEQ ID NO 27
<211> LENGTH: 304
<212> TYPE: PRT
<213> ORGANISM: Homo sapiens

<400> SEQUENCE: 27

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
        195                 200                 205

Lys Ser His Gly Arg Thr Gln Asp Glu Asn Pro Val Val His Phe Phe
    210                 215                 220
```

```
Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
            245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro Met Ala Arg Arg
            290                 295                 300

<210> SEQ ID NO 28
<211> LENGTH: 198
<212> TYPE: PRT
<213> ORGANISM: Homo sapiens

<400> SEQUENCE: 28

Asp Met Ala Ser His Lys Arg Pro Ser Gln Arg His Gly Ser Lys Tyr
1               5                   10                  15

Leu Ala Thr Ala Ser Thr Met Asp His Ala Arg His Gly Phe Leu Pro
            20                  25                  30

Arg His Arg Asp Thr Gly Ile Leu Asp Ser Ile Gly Arg Phe Phe Gly
            35                  40                  45

Ser Asp Arg Gly Ala Pro Lys Arg Gly Ser Gly Lys Val Pro Trp Leu
50                  55                  60

Lys Pro Gly Arg Ser Pro Leu Pro Ser His Ala Arg Ser Gln Pro Gly
65                  70                  75                  80

Leu Cys Asn Met Tyr Lys Asp Ser His His Pro Ala Arg Thr Ala His
                85                  90                  95

Tyr Gly Ser Leu Pro Gln Lys Ser His Gly Arg Thr Gln Asp Glu Asn
            100                 105                 110

Pro Val Val His Phe Phe Lys Asn Ile Val Thr Pro Arg Thr Pro Pro
            115                 120                 125

Pro Ser Gln Gly Lys Gly Arg Gly Leu Ser Leu Ser Arg Phe Ser Trp
130                 135                 140

Gly Ala Glu Gly Gln Arg Pro Gly Phe Gly Tyr Gly Gly Arg Ala Ser
145                 150                 155                 160

Asp Tyr Lys Ser Ala His Lys Gly Phe Lys Gly Val Asp Ala Gln Gly
                165                 170                 175

Thr Leu Ser Lys Ile Phe Lys Leu Gly Gly Arg Asp Ser Arg Ser Gly
            180                 185                 190

Ser Pro Met Ala Arg Arg
        195

<210> SEQ ID NO 29
<211> LENGTH: 3038
<212> TYPE: DNA
<213> ORGANISM: Artificial Sequence
<220> FEATURE:
<223> OTHER INFORMATION: Synthetic

<400> SEQUENCE: 29
tcaatcagaa agcccttttc attgcaggag aagaggacaa agatactcag agagaaaaag      60
taaaagaccg aagaaggagg ctggagagac caggatcctt ccagctgaac aaagtcagcc     120
acaaagcaga ctagccagcc ggctacaatt ggagtcagag tcccaaagac atgggcttgt     180
tagagtgctg tgcaagatgt ctggtagggg ccccctttgc ttccctggtg ccactggat      240
```

```
tgtgtttctt tggggtggca ctgttctgtg gctgtggaca tgaagccctc actggcacag      300
aaaagctaat tgagacctat ttctccaaaa actaccaaga ctatgagtat ctcatcaatg      360
tgatccatgc cttccagtat gtcatctatg gaactgcctc tttcttcttc ctttatgggg      420
ccctcctgct ggctgagggc ttctacacca ccggcgcagt caggcagatc tttggcgact      480
acaagaccac catctgcggc aagggcctga gcgcaacggt aacaggggc cagaagggga       540 ggggttccag aggccaacat caagctcatt ctttggagcg gtgtgtcat tgtttgggaa       600 aatggctagg acatcccgac aagtttgtgg gcatcaccta tgccctgacc gttgtgtggc      660
tcctggtgtt tgcctgctct gctgtgcctg tgtacattta cttcaacacc tggaccacct      720
gccagtctat tgccttcccc agcaagacct ctgccagtat aggcagtctc tgtgctgatg      780
ccagaatgta tggtgttctc ccatggaatg ctttccctgg caaggtttgt ggctccaacc      840
ttctgtccat ctgcaaaaca gctgagttcc aaatgacctt ccacctgttt attgctgcat      900
ttgtgggggc tgcagctaca ctggtttccc tgctcacctt catgattgct gccacttaca      960
actttgccgt ccttaaactc atgggccgag gcaccaagtt ctgatccccc gtagaaatcc     1020 cccttttctct aatagcgagg ctctaaccac acagcctaca atgctgcgtc tcccatctta    1080
actctttgcc tttgccacca actggccctc ttcttacttg atgagtgtaa caagaaagga     1140
gagtcttgca gtgattaagg tctctctttg gactctcccc tcttatgtac ctcttttagt     1200
cattttgctt catagctggt tcctgctaga aatgggaaat gcctaagaag atgacttccc     1260
aactgcaagt cacaaaggaa tggaggctct aattgaattt tcaagcatct cctgaggatc     1320
agaaagtaat ttcttctcaa agggtacttc cactgatgga aacaaagtgg aaggaaagat     1380
gctcaggtac agagaaggaa tgtctttggt cctcttgcca tctataggg ccaaatatat      1440 tctctttggt gtacaaaatg gaattcattc tggtctctct attaccactg aagatagaag     1500
aaaaaagaat gtcagaaaaa caataagagc gtttgcccaa atctgcctat tgcagctggg     1560 agaaggggt caaagcaagg atctttcacc cacagaaaga gagcactgac cccgatggcg      1620
atggactact gaagccctaa ctcagccaac cttacttaca gcataaggga gcgtagaatc     1680
tgtgtagacg aagggggcat ctggccttac acctcgttag ggaagagaaa cagggtgttg     1740
tcagcatctt ctcactccct tctccttgat aacagctacc atgacaaccc tgtggtttcc     1800
aaggagctga gaatagaagg aaactagctt acatgagaac agactggcct gaggagcagc     1860
agttgctggt ggctaatggt gtaacctgag atggccctct ggtagacaca ggatagataa     1920
ctctttggat agcatgtctt ttttctgtt aattagttgt gtactctggc ctctgtcata      1980
tcttcacaat ggtgctcatt tcatgggggt attatccatt cagtcatcgt aggtgatttg     2040
aaggtcttga tttgttttag aatgatgcac atttcatgta ttccagtttg tttattactt     2100
atttggggtt gcatcagaaa tgtctggaga ataattcttt gattatgact gttttttaaa     2160
ctaggaaaat tggacattaa gcatcacaaa tgatattaaa aattggctag ttgaatctat     2220
tgggattttc tacaagtatt ctgcctttgc agaaacagat ttggtgaatt tgaatctcaa     2280
tttgagtaat ctgatcgttc tttctagcta atggaaaatg attttactta gcaatgttat     2340
cttggtgtgt taagagttag gtttaacata aggttattt tctcctgata tagatcacat      2400
aacagaatgc accagtcatc agctattcag ttggtaagct tccaggaaaa aggacaggca     2460
gaaagagttt gagacctgaa tagctcccag atttcagtct tttcctgttt ttgttaactt     2520
tgggttaaaa aaaaaaaag tctgattggt tttaattgaa ggaaagattt gtactacagt      2580
```

-continued

```
tcttttgttg taaagagttg tgttgttctt ttcccccaaa gtggtttcag caatatttaa    2640
ggagatgtaa gagctttaca aaaagacact tgatacttgt tttcaaacca gtatacaaga    2700
taagcttcca ggctgcatag aaggaggaga gggaaaatgt tttgtaagaa accaatcaag    2760
ataaaggaca gtgaagtaat ccgtaccttg tgttttgttt tgatttaata acataacaaa    2820
taaccaaccc ttccctgaaa acctcacatg catacataca catatataca cacacaaaga    2880
gagttaatca actgaaagtg tttccttcat ttctgatata gaattgcaat tttaacacac    2940
ataaaggata aacttttaga aacttatctt acaaagtgta ttttataaaa ttaaagaaaa    3000
taaaattaag aatgttctca atcaaaaaaa aaaaaaaa                            3038
```

<210> SEQ ID NO 30
<211> LENGTH: 277
<212> TYPE: PRT
<213> ORGANISM: Homo sapiens

<400> SEQUENCE: 30

```
Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val
    50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
    210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275
```

```
<210> SEQ ID NO 31
<211> LENGTH: 21
<212> TYPE: PRT
<213> ORGANISM: Artificial Sequence
<220> FEATURE:
<223> OTHER INFORMATION: Synthetic

<400> SEQUENCE: 31

Met Glu Val Gly Trp Tyr Arg Ser Pro Phe Ser Arg Val Val His Leu
1               5                   10                  15

Tyr Arg Asn Gly Lys
            20

<210> SEQ ID NO 32
<211> LENGTH: 8
<212> TYPE: PRT
<213> ORGANISM: Artificial Sequence
<220> FEATURE:
<223> OTHER INFORMATION: synthetic

<400> SEQUENCE: 32

Ser Ile Ile Asn Phe Glu Lys Leu
1               5
```

MYELIN OLIGODENDROCYTE GLYCOPROTEIN, MYELIN BASIC PROTEIN, AND PROTEOLIPID PROTEIN COMPOSITIONS AND METHODS OF USE

CROSS-REFERENCE TO RELATED APPLICATIONS

This patent application is 35 U.S.C. § 371 U.S. national entry of International Patent Application No. PCT/US2016/021571 (WO 2016/145086 A1), filed Mar. 9, 2016, which claims the benefit of U.S. Provisional Patent Application No. 62/130,285, filed Mar. 9, 2015, and U.S. Provisional Patent Application No. 62/219,851, filed Sep. 17, 2015, which are incorporated herein by reference in their entirety.

GOVERNMENT FUNDING

Research supporting this application was carried out by the United States of America as represented by the Secretary, Department of Health and Human Services.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 50,781 Byte ASCII (Text) file named "723520_ST25," dated Mar. 8, 2016.

BACKGROUND OF THE INVENTION

Demyelinating diseases may involve damage to the myelin sheath of neurons. For example, multiple sclerosis (MS) is considered to be an autoimmune demyelinating disease of the central nervous system (CNS) affecting approximately 2.5 million people in the world with varying degrees of disability. MS can cause problems with muscle control and strength, vision, balance, sensation, and mental functions, and ultimately leaves many individuals wheelchair bound. The lifespan of an MS patient may be about 5 to about 10 years lower than that of healthy individuals. Despite advancements in the treatment of demyelinating diseases, there exists a need for improved treatments for demyelinating diseases.

BRIEF SUMMARY OF THE INVENTION

An embodiment of the invention provides a protein comprising no more than three human autoantigenic proteins, wherein a first human autoantigenic protein comprises a truncated myelin oligodendrocyte glycoprotein (MOG) amino acid sequence, a second human autoantigenic protein comprises a myelin basic protein (MBP) amino acid sequence, and a third human autoantigenic protein comprises a truncated proteolipid protein (PLP) amino acid sequence.

Another embodiment of the invention provides a protein comprising all of (a) a MOG amino acid sequence at least about 90% identical to SEQ ID NO: 1 or 25; (b) a MBP amino acid sequence at least about 90% identical to SEQ ID NO: 2 or 28; and (c) a PLP amino acid sequence at least about 90% identical to SEQ ID NO: 3.

Still another embodiment of the invention provides a composition comprising a mixture of (a) a MOG protein comprising an amino acid sequence at least about 90% identical to SEQ ID NO: 1 or 25; (b) a MBP protein comprising an amino acid sequence at least about 90% identical to SEQ ID NO: 2 or 28; and (c) a PLP protein comprising an amino acid sequence at least about 90% identical to SEQ ID NO: 3.

Another embodiment of the invention provides a method of treating or preventing MS in a mammal, the method comprising administering to the mammal the inventive protein, the inventive nucleic acid, or the inventive composition in an amount effective to treat or prevent MS in the mammal.

Additional embodiments of the invention provide related nucleic acids, pharmaceutical compositions, and methods of producing the inventive proteins.

BRIEF DESCRIPTION OF THE SEVERAL VIEWS OF THE DRAWING(S)

Figure 3:
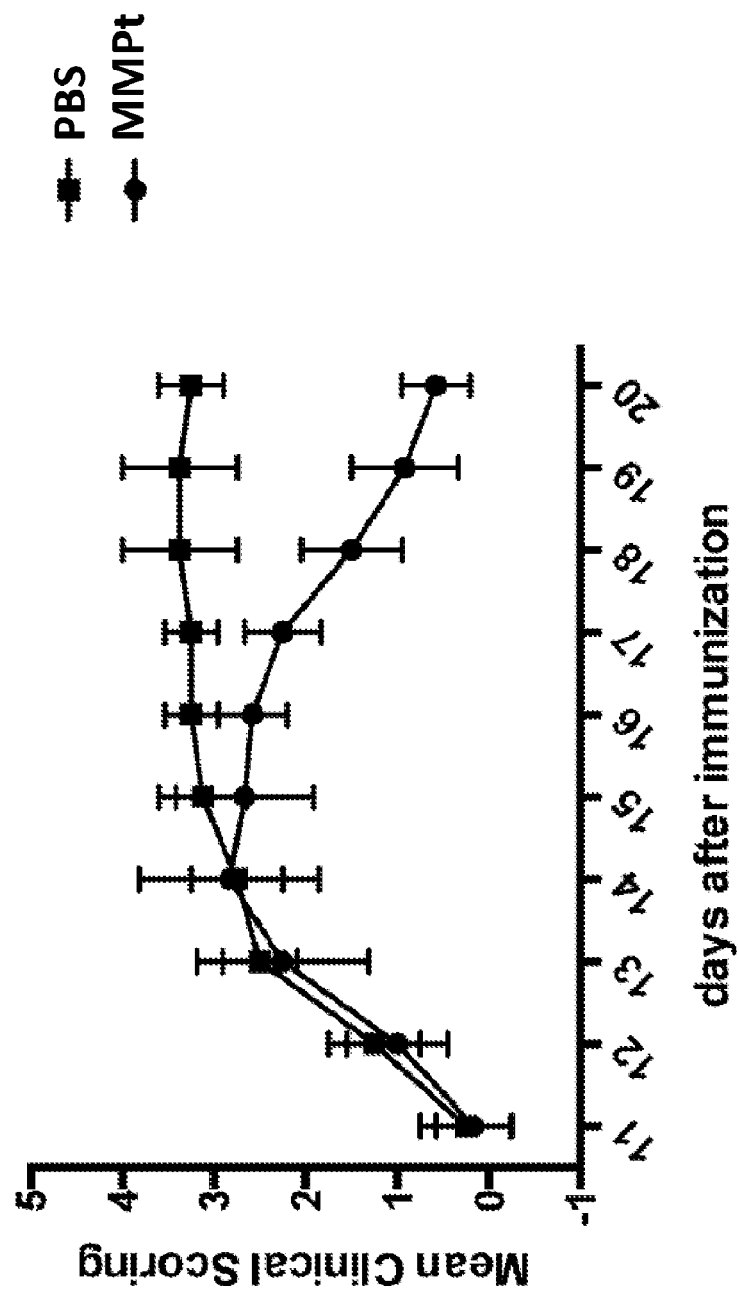

FIG. 3 is a graph showing the mean clinical scoring of mice with MOG-induced EAE that were treated with PBS (squares) or MMPt (SEQ ID NO: 19) (circles) at various days after immunization. One representative of three independent experiments is shown. PBS group (n=4), MMPt treatment (n=6).

Figure 4A:
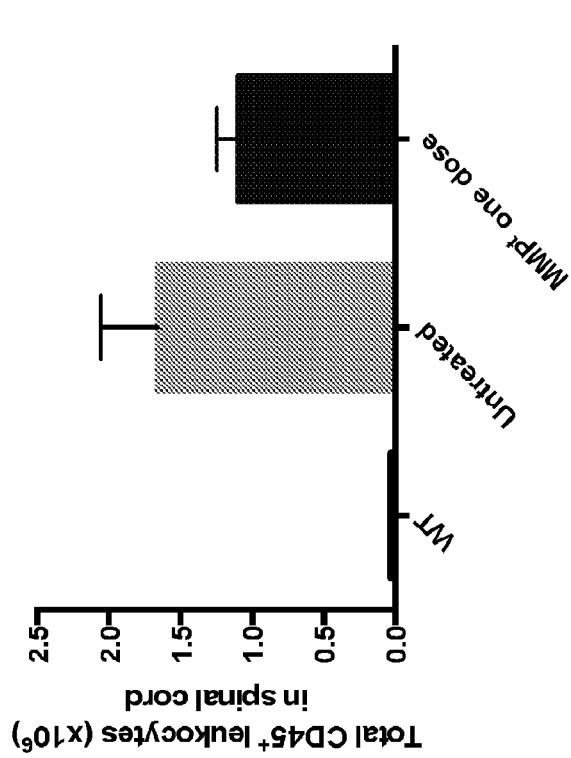

FIG. 4A is a graph showing the total number of $CD45^+$ leukocytes ($\times 10^6$) in the spinal cord of wild-type unimmunized mice, untreated mice with EAE, and EAE mice treated with one dose of MMPt.

Figure 4B:
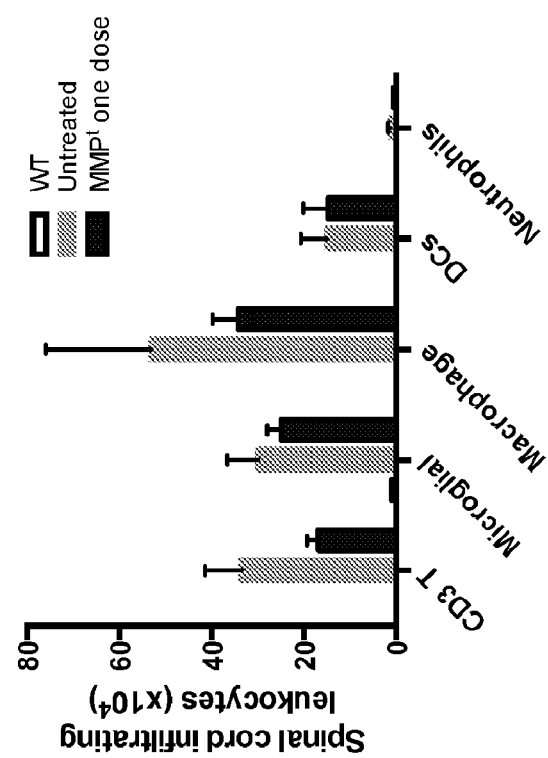

FIG. 4B is a graph showing the total number of CD3+ T cells, microglial cells, macrophages, dendritic cells (DCs), and neutrophils ($\times 10^4$) in the spinal cord of wild-type unimmunized mice (unshaded bars), untreated mice with EAE (grey bars), and EAE mice treated with one dose of MMPt (black bars).

Figure 5A:
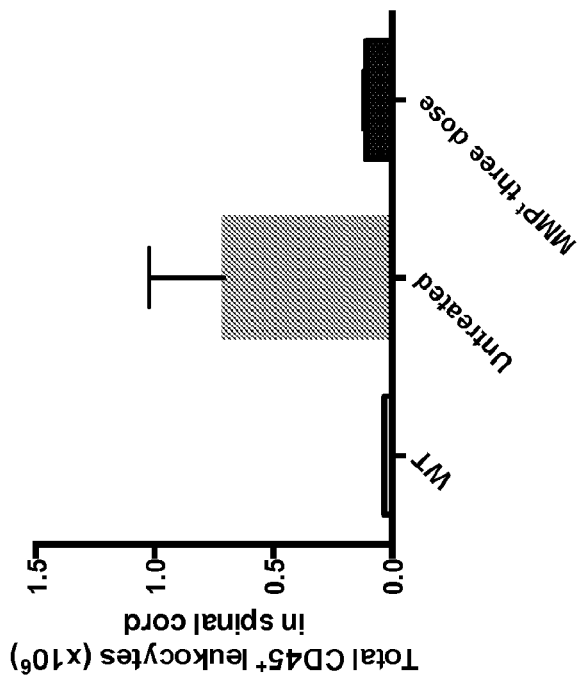

FIG. 5A is a graph showing the total number of $CD45^+$ leukocytes ($\times 10^6$) in the spinal cord of wild-type unimmunized mice, untreated EAE mice, and EAE mice treated with three doses of MMPt.

Figure 5B:
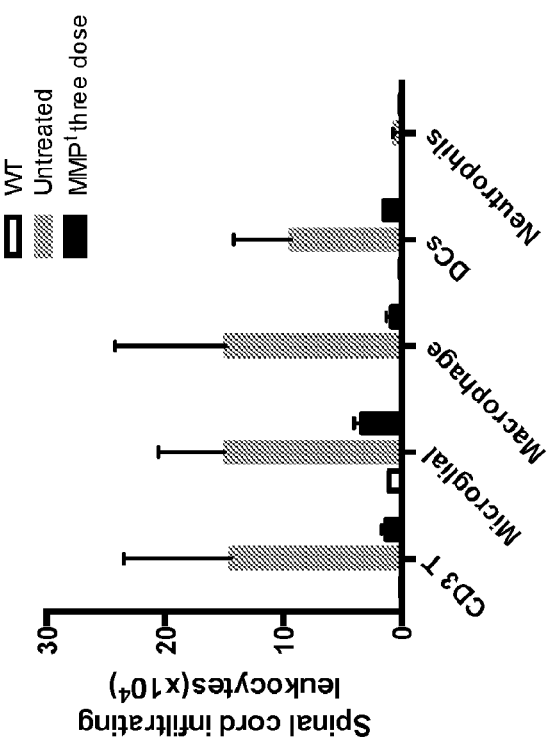

FIG. 5B is a graph showing the total number of CD3+ T cells, microglial cells, macrophages, DCs, and neutrophils ($\times 10^4$) in the spinal cord of wild-type unimmunized mice (unshaded bars), untreated EAE mice (grey bars), and EAE mice treated with three doses of MMPt (black bars).

Figure 6:
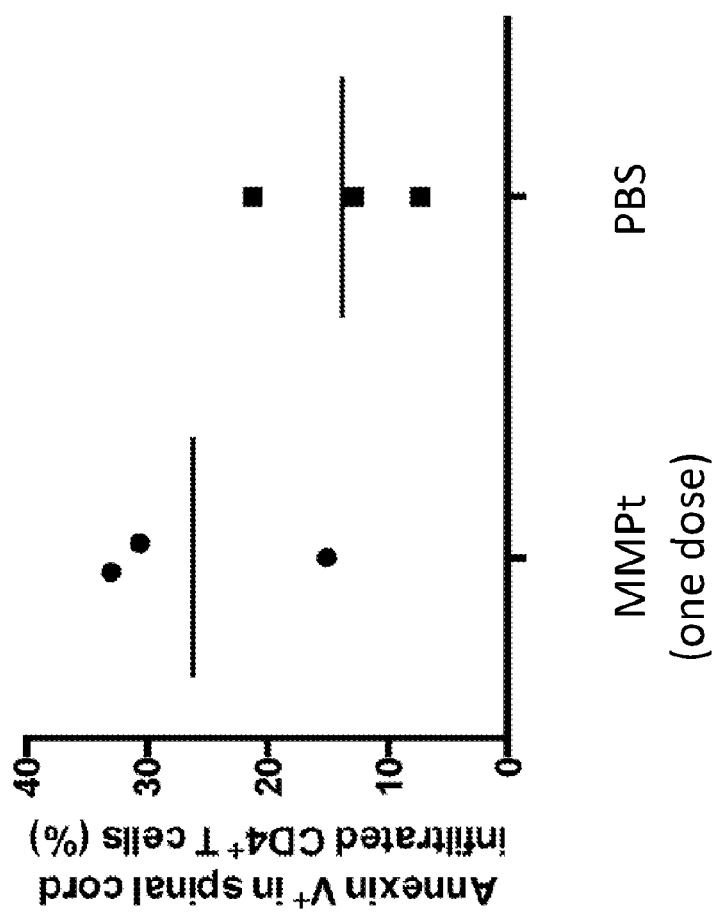

FIG. 6 is a graph showing the percentage of apoptotic CD4+ T cells in the spinal cord 20 hours after PBS (squares) or MMPt (circles) injection, as measured by annexin V staining.

Figure 7A:
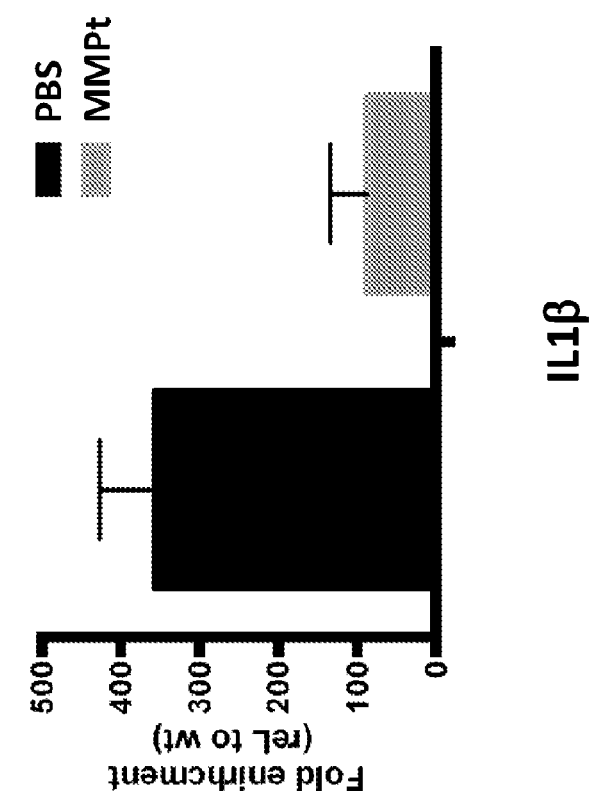
Figure 7B:
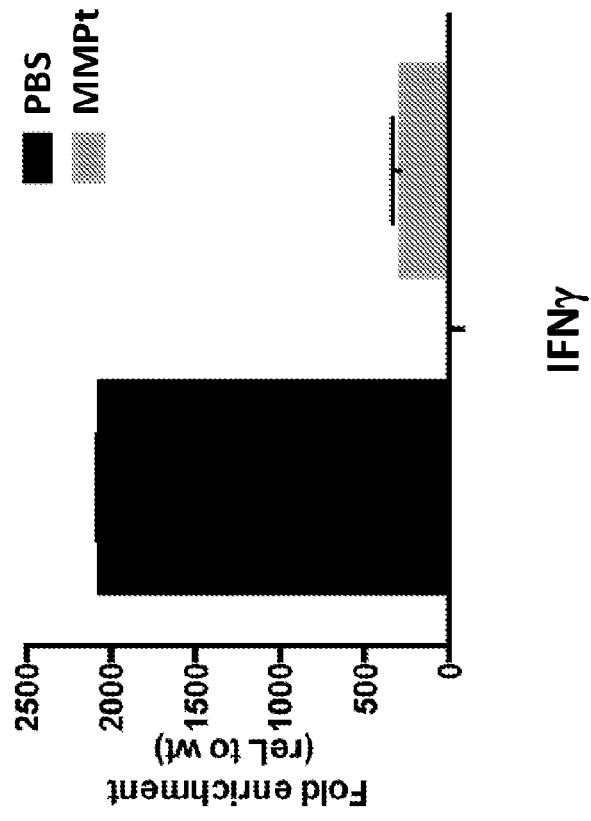

FIGS. 7A and 7B are graphs showing the fold enrichment of IFN-γ (A) and IL-10 (B) (relative to wild-type mice) in the spinal cord of PBS-treated EAE mice (black bars) and MMPt-treated EAE mice (grey bars) 20 hours after MMPt injection.

Figure 8:
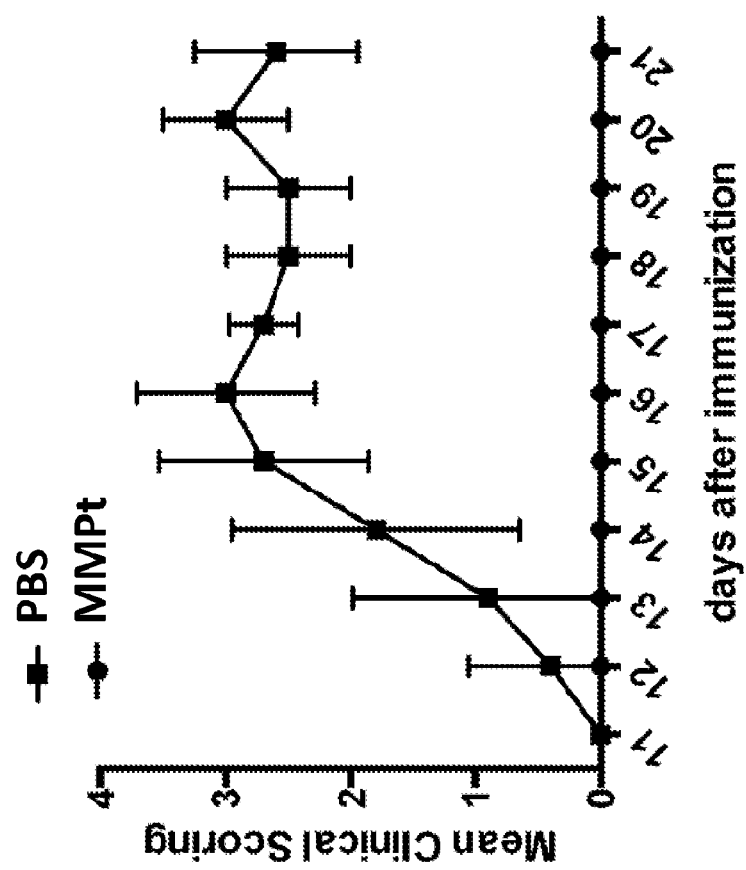

FIG. 8 is a graph showing the mean clinical scoring of mice with MOG-induced EAE that were treated with MMPt (SEQ ID NO: 19) (circles) or PBS (squares) at various days after immunization. One representative of 2 independent experiments is shown. PBS (n=5), MMPt group (n=4), ***p<0.001.

Figure 9:
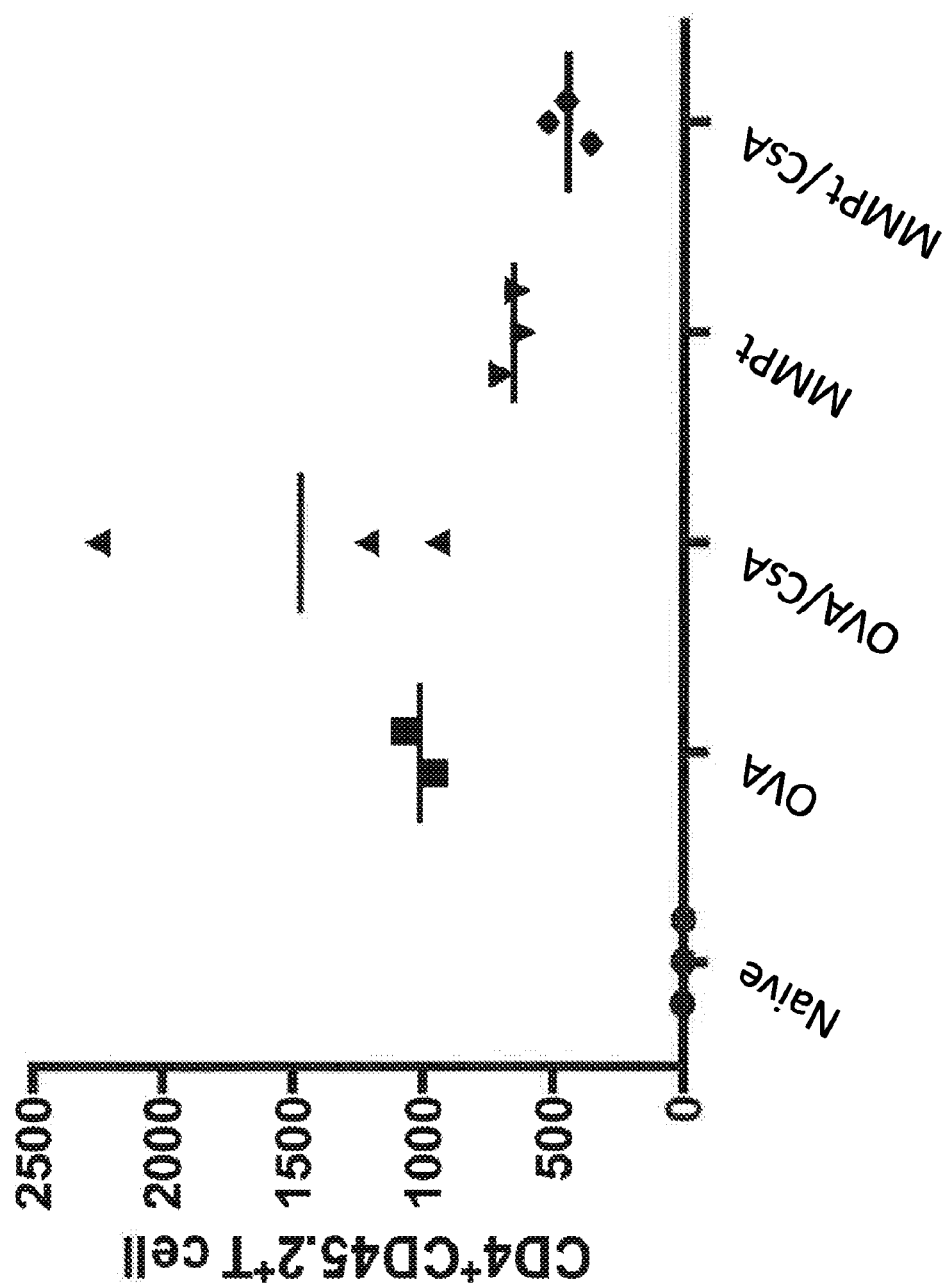

FIG. 9 is a graph showing the numbers of adoptively transferred, CFSE-labeled, MOG-peptide specific, CD4+ CD45.2+ T cells detected in B6 mice after the mice were treated with ovalbumin (OVA) alone (squares), a combination of OVA and cyclosporin A (CsA) (▲), MMPt alone (▼), or a combination of MMPt and CsA (diamonds). CD4+ CD45.2+ T cells from naïve (unimmunized) mice (circles) served as a control.

Figure 10A:
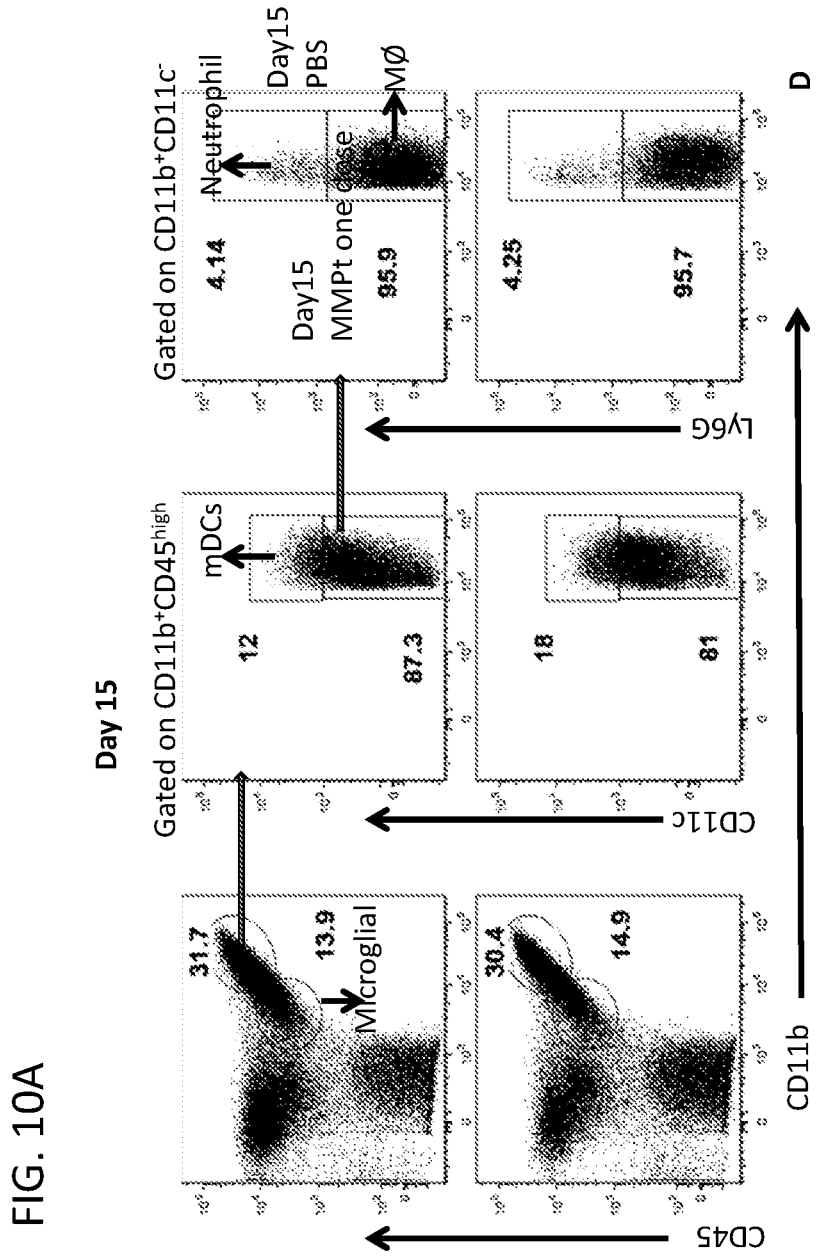

FIG. 10A includes flow cytometry plots showing the percentage of spinal cord infiltrating cells expressing the indicated markers 15 days after immunization and 20 hours after single dose of 800 μg MMPt or PBS (control) i.v.

Figure 10B:
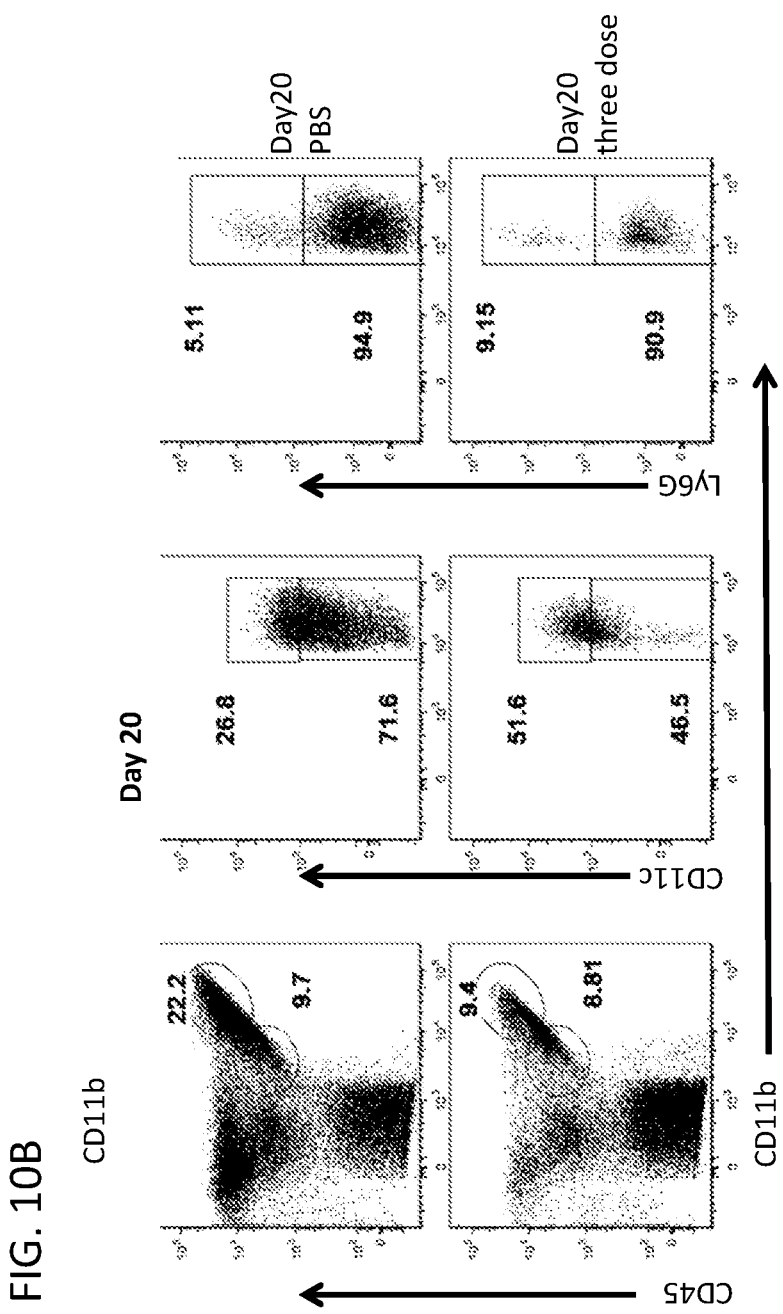

FIG. 10B includes flow cytometry plots showing the percentage of spinal cord infiltrating cells expressing the indicated markers 20 days after immunization and after three doses of 800 μg MMPt or PBS (control) i.v.

Figure 11:
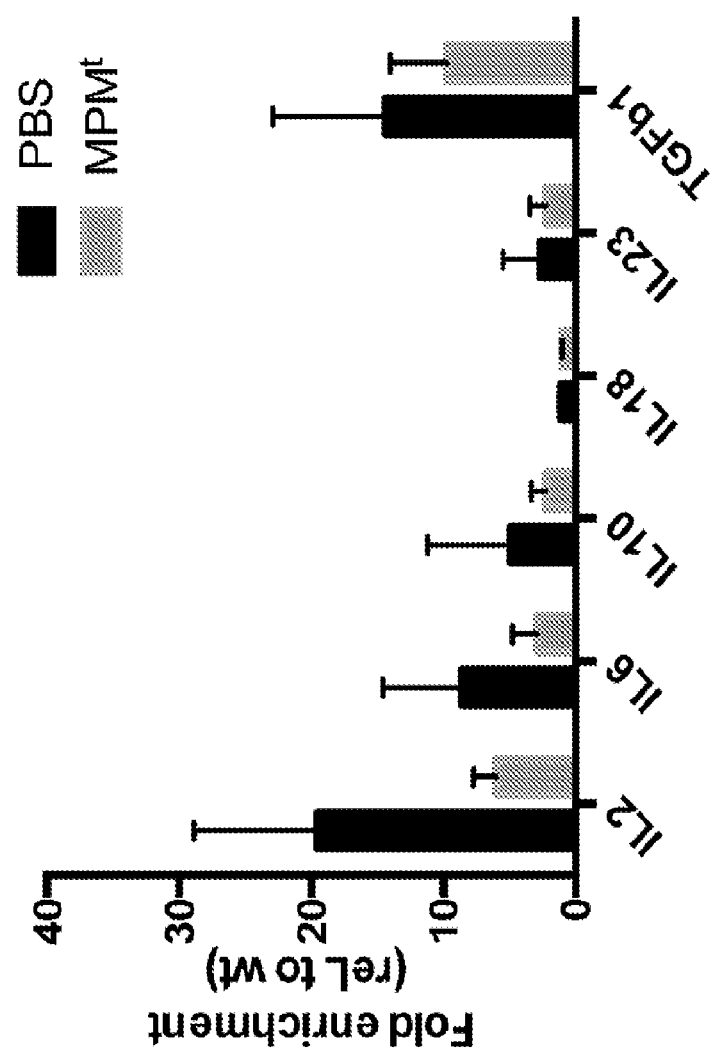
Figure 19A:
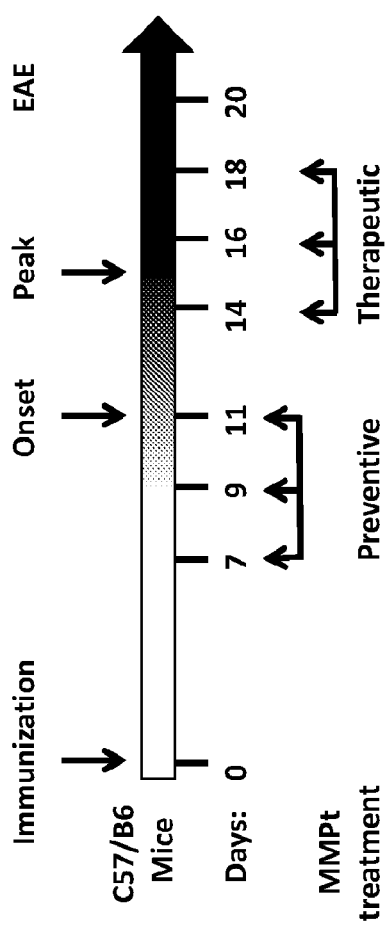

FIG. 11 is a graph showing the fold-enrichment in expression of each the indicated cytokines in EAE spinal cord (relative to wild-type) following treatment with three doses of PBS (control) or 800 μg MMPt i.v. administered as shown in the therapeutic schedule shown in FIG. 19A.

Figure 12:
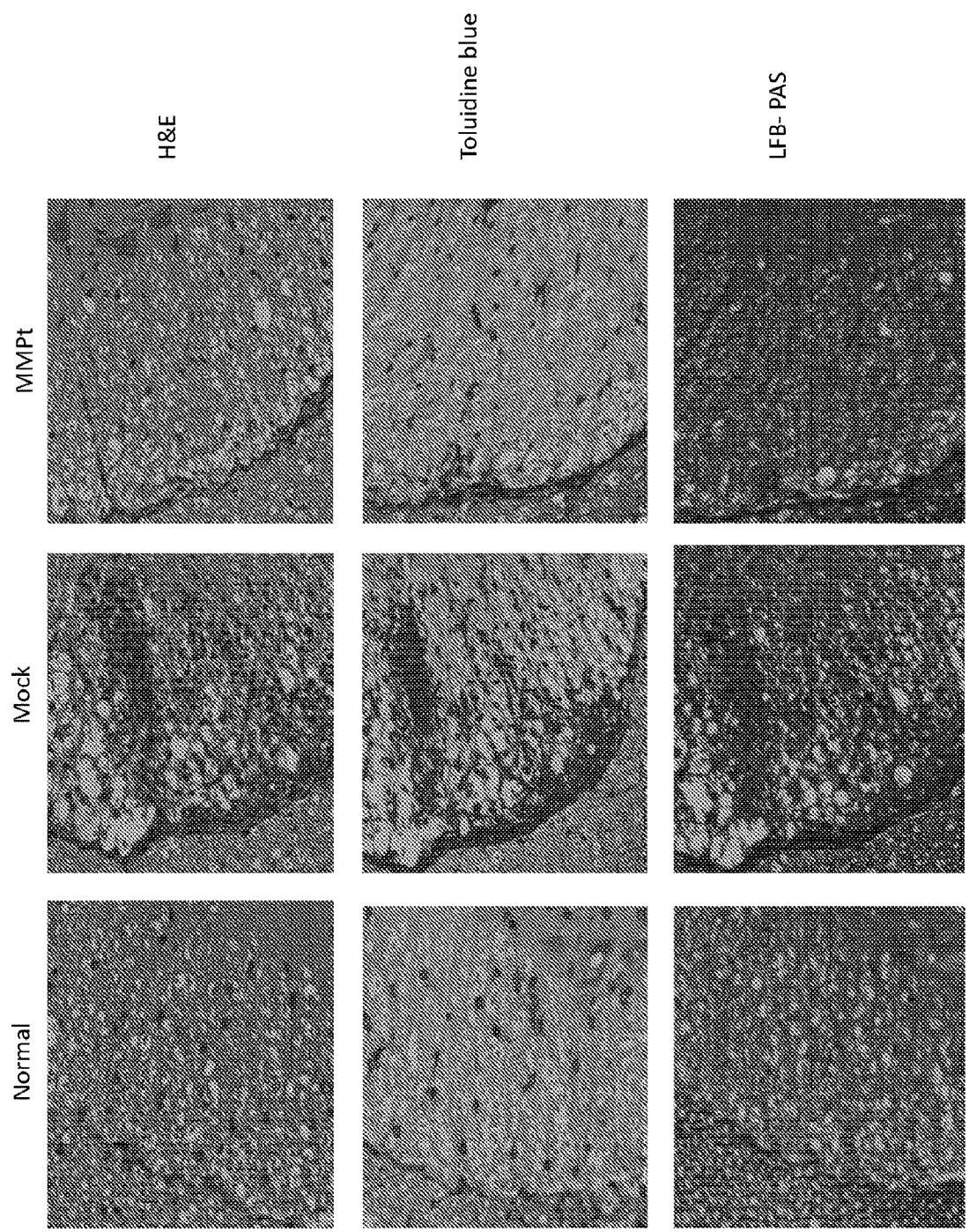

FIG. 12 includes images of fixed spinal cord tissues from age-matched normal (naïve) (left), phosphate buffered saline (PBS) (Mock), and 800 μg MMPt treated EAE mice. The sections were stained with H&E (top panels), Toluidine blue (middle panels), and Luxol fast blue (LFB)-Periodic acid Schiff (PAS) stain (bottom panels), respectively.

Figure 13:
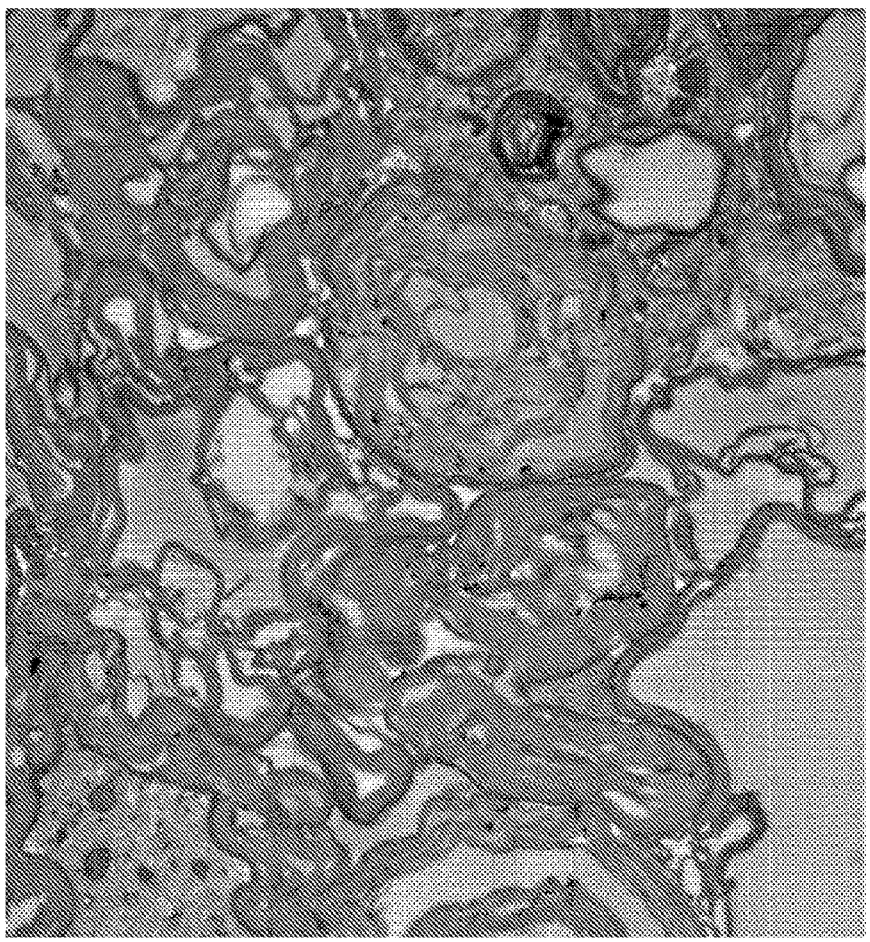

FIG. 13 shows an electron micrograph (EM) of spinal cord tissue from a normal mouse showing normal myelin sheath.

Figure 14:
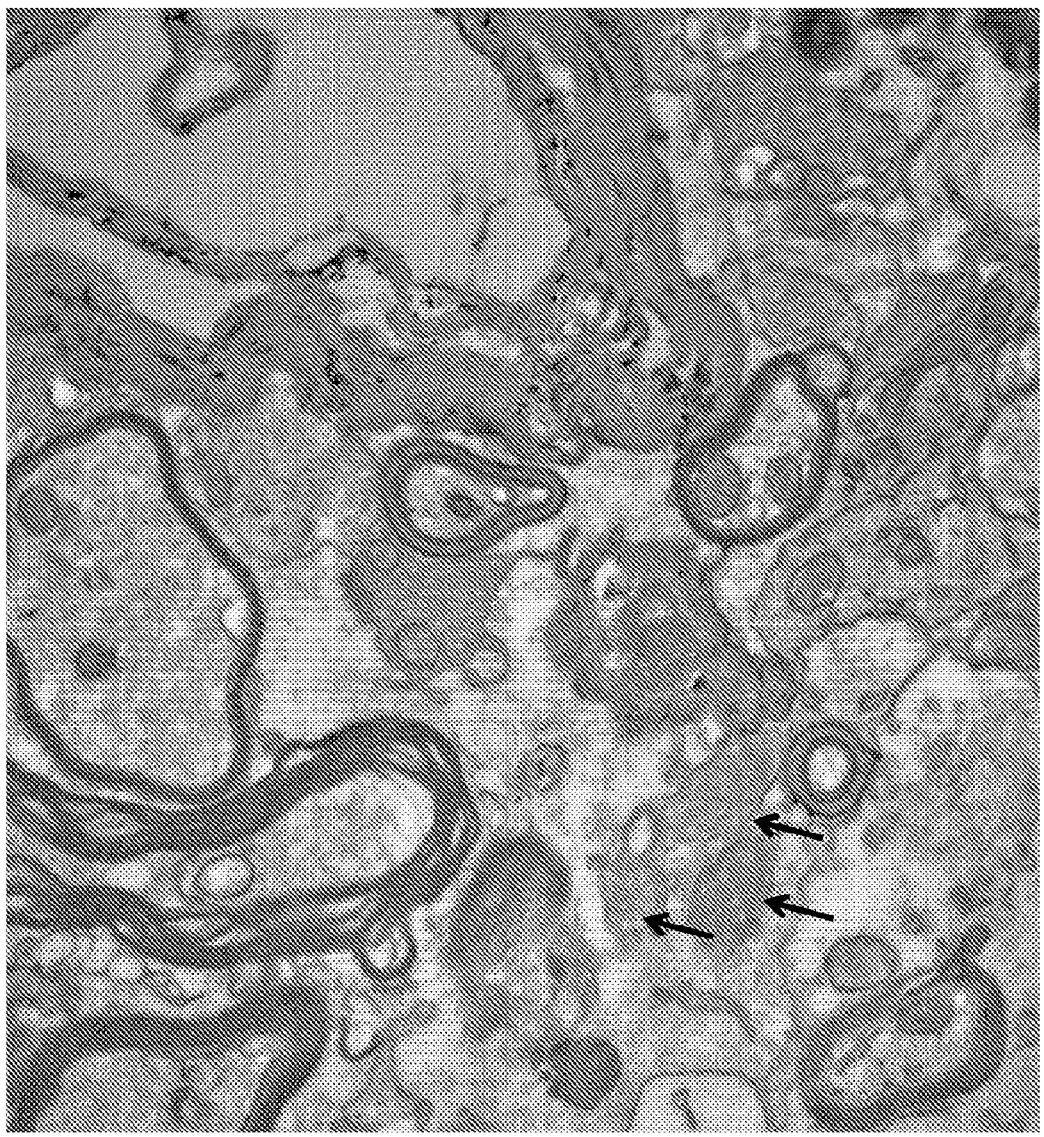

FIG. 14 shows an EM of spinal cord tissue from a mock (control)-treated EAE mouse showing demyelination and naked axons. The arrows point to demyelination.

Figure 15:
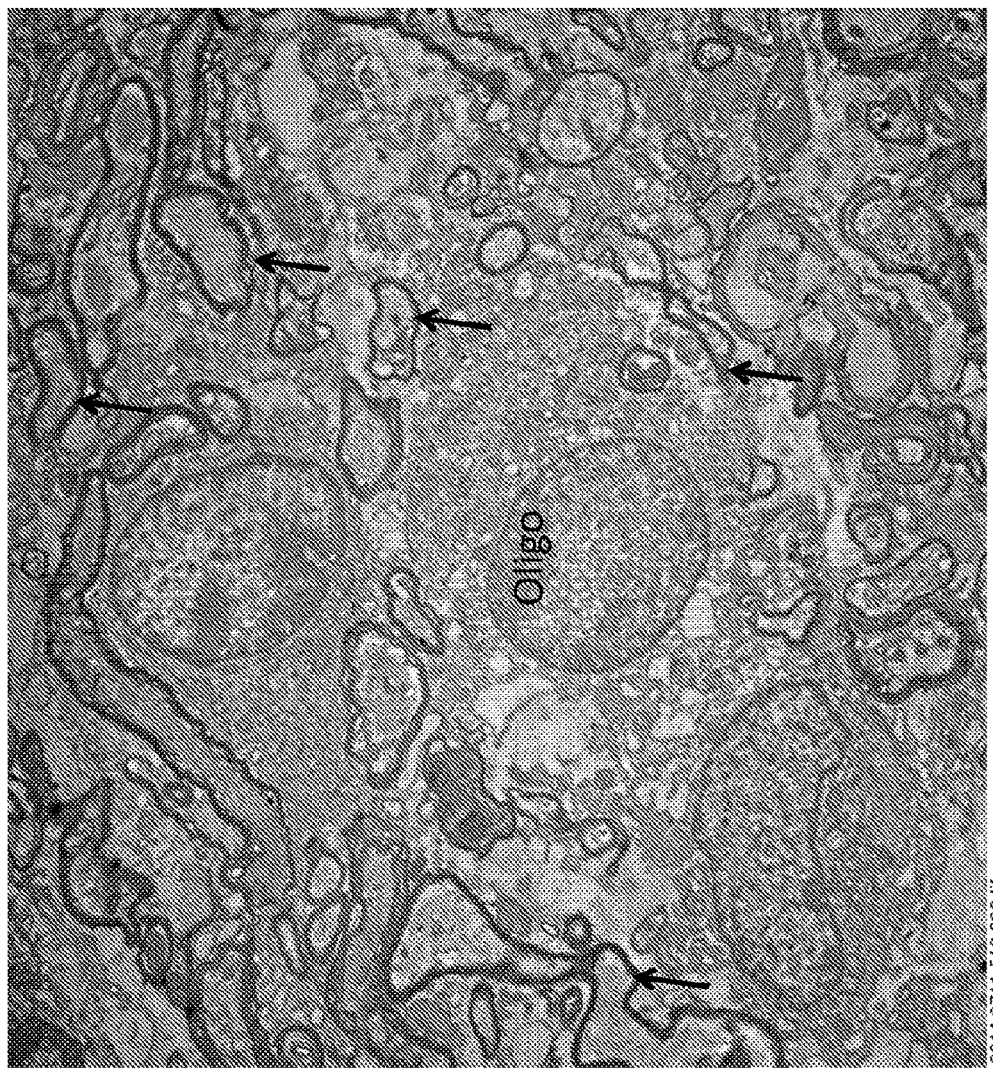

FIG. 15 shows an EM of a typical structure of remyelination occurring on an axon in an MMPt-treated EAE mouse. The arrows point to protection of the myelin sheath from damage and possible re-myelination. "Oligo" shows the location of a cell body of an oligodendrocyte.

Figure 16:
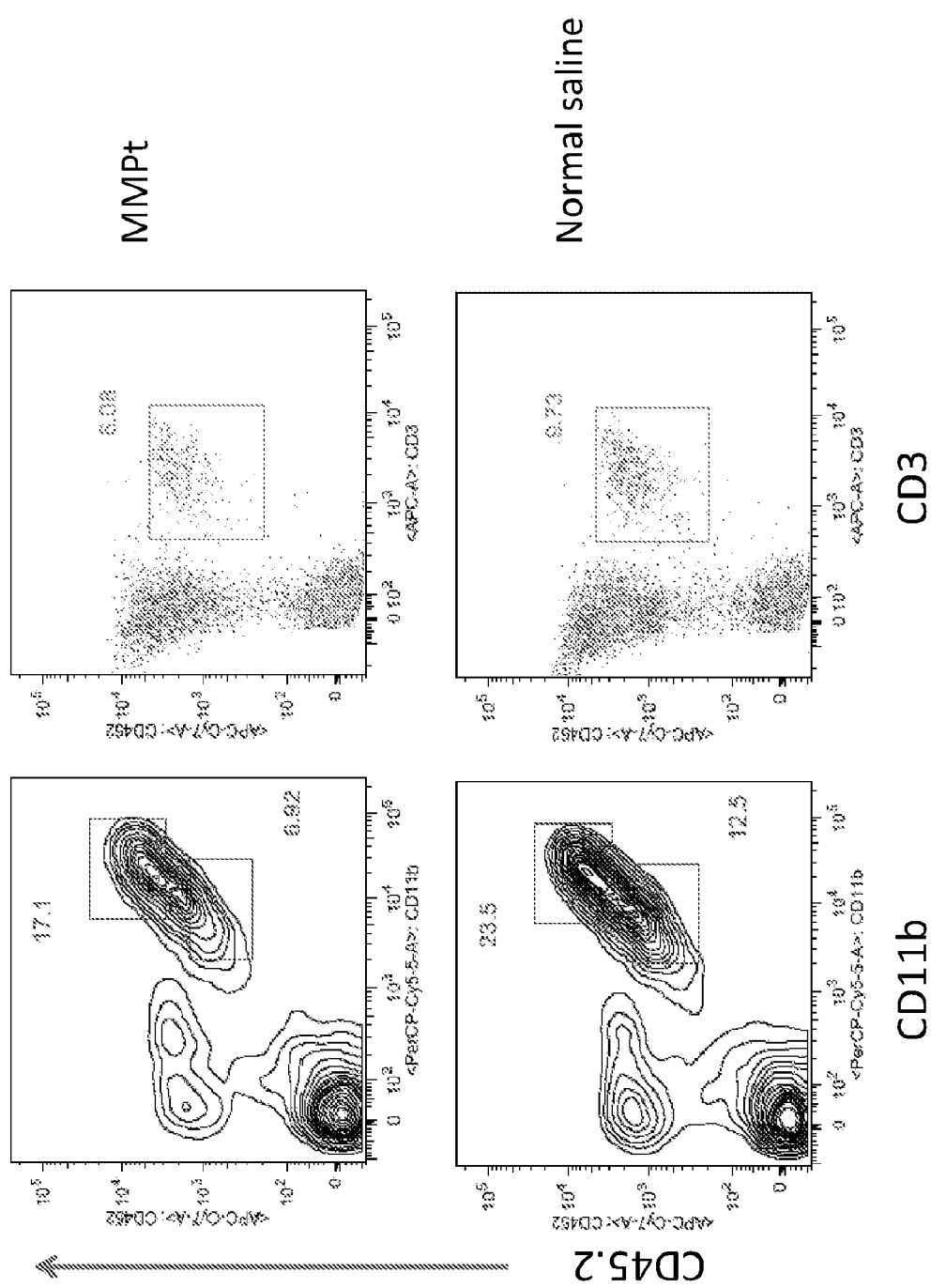

FIG. 16 includes flow cytometry plots showing the percentage of spinal cord cells expressing the indicated markers after MMPt treatment as compared to control treatment.

Figure 17:
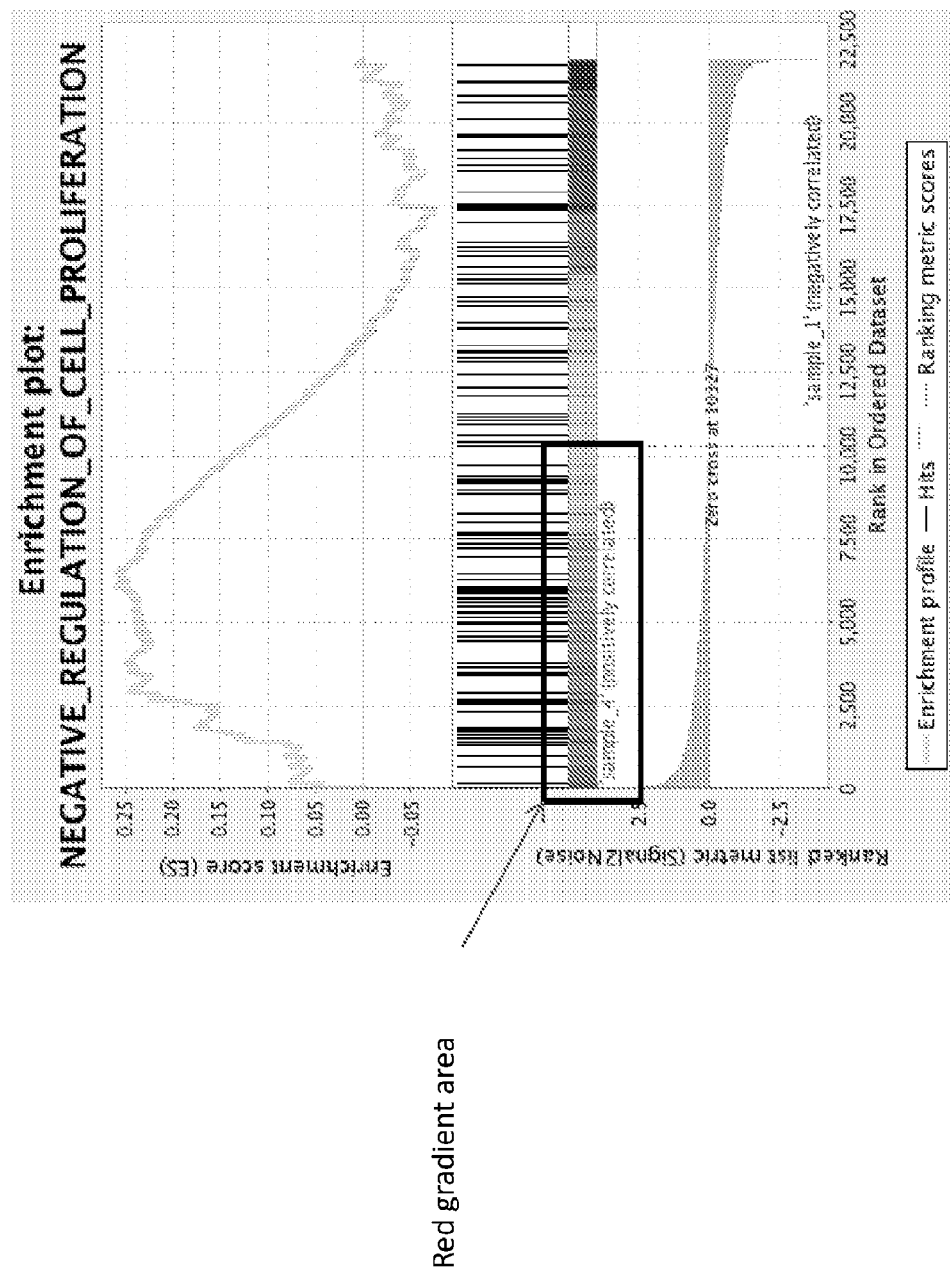

FIG. 17 is an image of the output from a microarray analysis (Gene Set Enrichment Analysis (GSEA)) showing that a negatively regulated pattern of monocytes/macrophages was observed in the MMPt treated samples (red gradient area) as compared to the normal saline controls (mock).

Figure 18A:
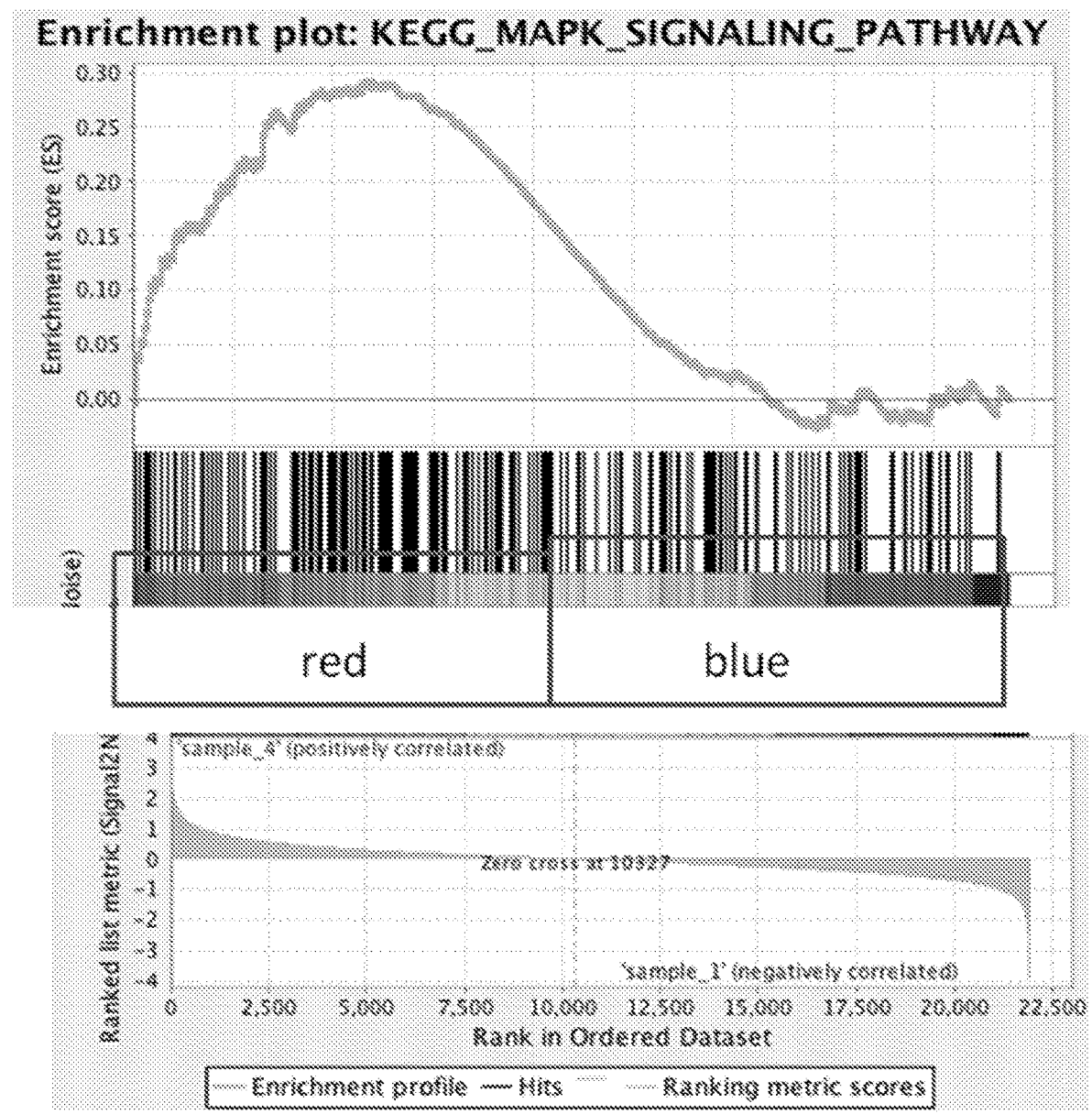

FIG. 18A shows the results of gene expression by GSEA pathway analysis and KEGG analysis showing the upregulation of genes involved in the MAPK signaling pathway for MMPt treated samples or normal saline-treated samples. Red=MMPt-treated for 20 hours. Blue=Normal saline-treated for 20 hours.

Figure 18B:
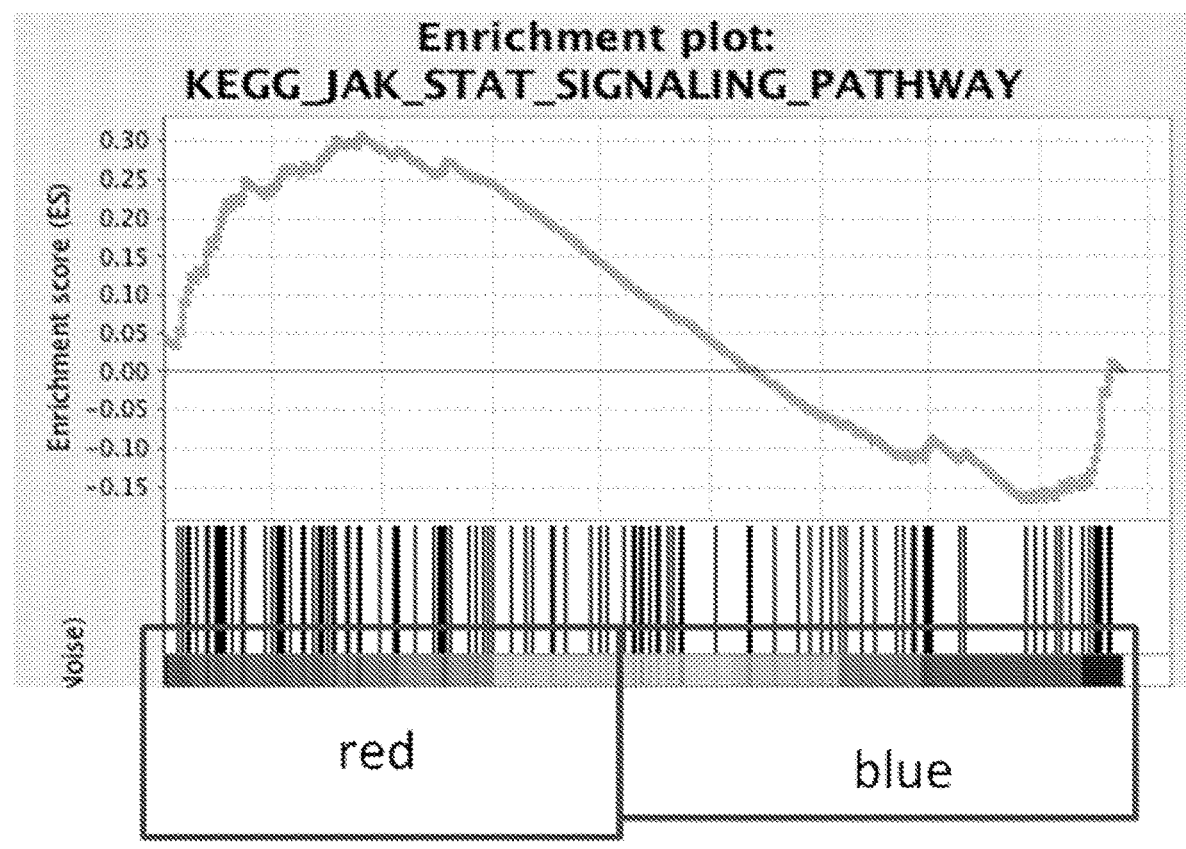

FIG. 18B shows the results of gene expression by GSEA pathway analysis and KEGG analysis showing the upregulation of genes involved in the JAK STAT signaling pathway for MMPt treated samples. Red=MMPt-treated for 20 hours. Blue=Normal saline-treated for 20 hours.

FIG. 19A is a schematic showing the experimental design testing for therapeutic and preventative treatment of $MOG_{34-55}$-induced EAE.

Figure 19B:
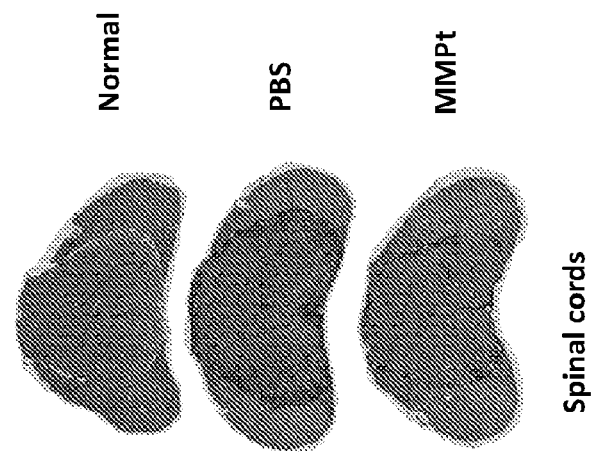

FIG. 19B shows images of histopathological H&E staining of spinal cord sections from a normal mouse, an EAE mouse treated on Day 20 with 3 doses of phosphate buffered saline (PBS), or an EAE mouse treated on Day 20 with 800 μg of MMPt.

FIG. 20A provides flow cytometery plots showing the percentage of cells expressing the indicated markers in naïve cells or cells isolated from the spinal cord of mice 15 or 20 days after treatement with 1 or 3 doses vehicle or 1 or 3 doses of MMPt. Shown are data from one representative of three independent experiments.

FIG. 20B is a graph showing the total number of spinal cord infiltrating CD3+CD45+ T cells as measured by FACS in wild type mice or EAE mice 15 or 20 days after treatement with 1 or 3 doses vehicle or 1 or 3 doses of MMPt.

FIG. 20C provides flow cytometry plots showing the apoptosis of CD3+ T cells in the spinal cord stained by Annexin V after one dose of MMPt or vehicle treatment.

FIG. 20D is a graph showing the total number of CD3+ T cells in the spinal cord stained by Annexin V after one dose of MMPt or vehicle treatment.

Figure 21A:
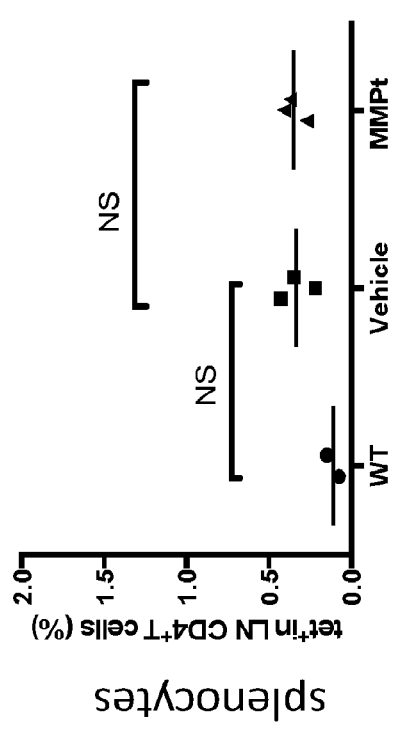

FIG. 21A is a graph showing the percentage of tetramer positive lymph node (LN) CD4+ T cells in splenocytes of wild-type mice or EAE mice treated with vehicle or MMPt. NS=not significant.

Figure 21B:
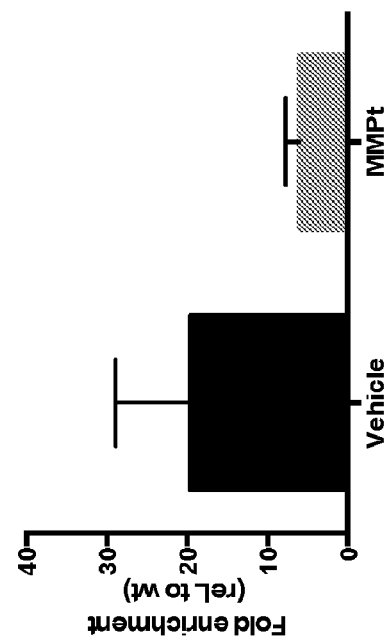

FIG. 21B is a graph showing the fold enrichment (relative to wild-type) of spinal cord IL2 RNA levels 20 hours after MMPt treatment as measured by real-time PCR.

Figure 22B:
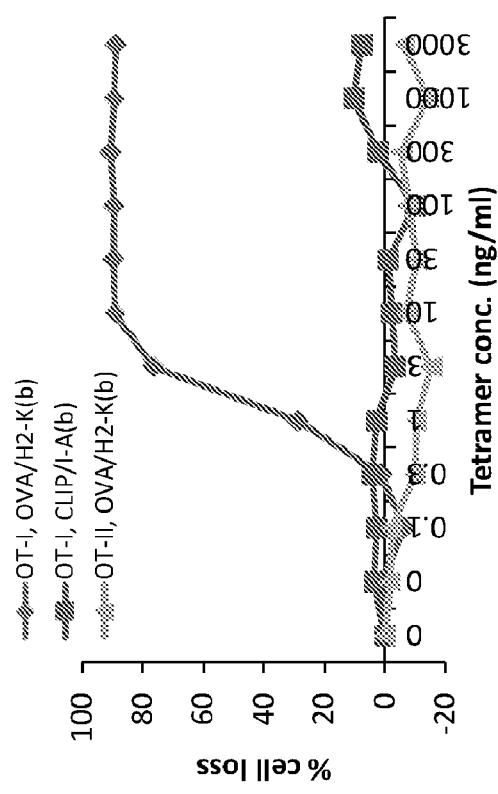
Figure 22A:
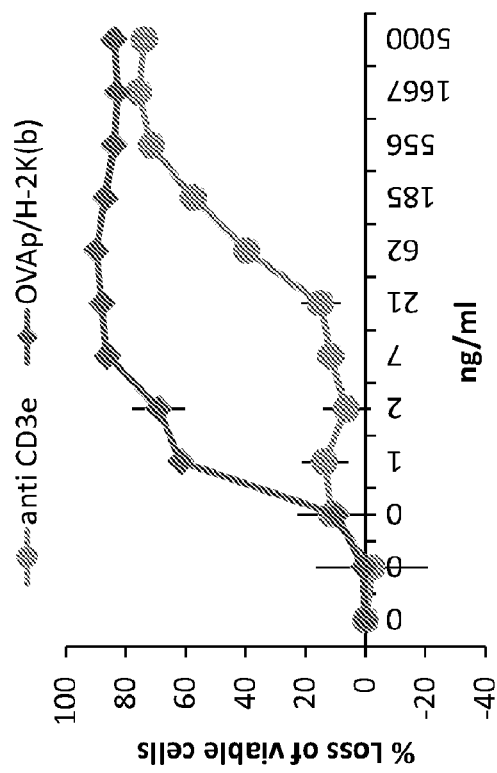

FIG. 22A is a graph showing the percent loss of activated OVA-specific OT-I TCR-Tg T cells in response to stimulations by anti-CD3e (2C11, circles) or OVAp (SIINFEKL) (SEQ ID NO: 32)/H-2K(b) tetramers (diamonds) at the indicated concentrations for 48 hours in vitro.

FIG. 22B is a graph showing the percent loss of activated OT-I Tg T cells in response to stimulations with tetramers at the indicated doses, diamonds: OVAp/H2-K(b), squares: control CLIP/I-A(b), triangles: OT-II specific OVAp/H2-K (b).

Figure 23A:
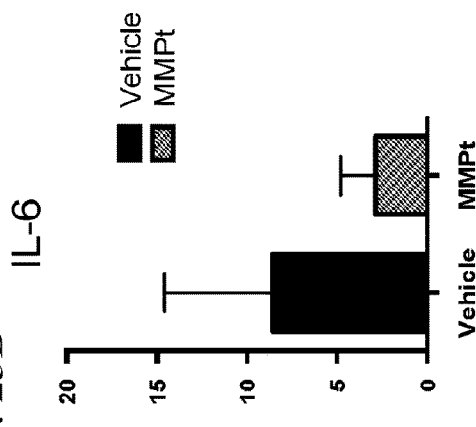

FIG. 23A is a graph showing the mean clinical scoring of WT mice and IL1r–/– mice at various time points (days) after immunization. WT group (n=4), solid circle: IL1r–/– group (n=8), square.

Figure 23C:
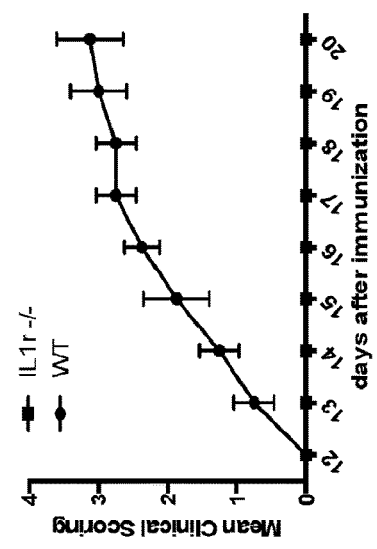
Figure 23B:
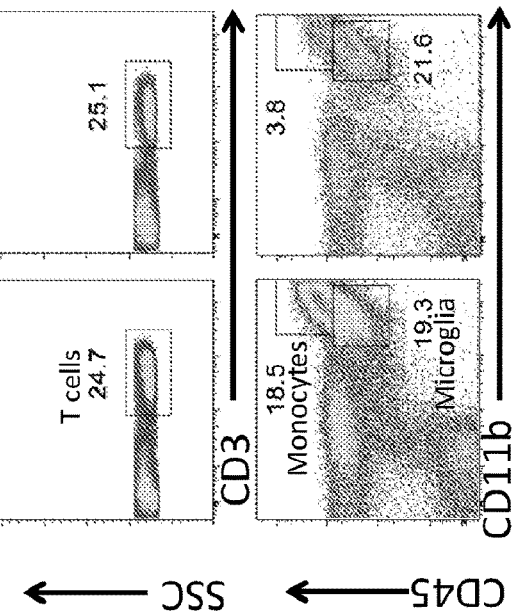

FIG. 23B is a graph showing IL-6 expression levels in the spinal cord of EAE mice 20 hours post vehicle or an 800 μg MMPt single day treatment.

FIG. 23C is a graph showing the decrease of inflammatory chemokines 20 hours after vehicle or MMPt single dose treatment.

Figure 23D:
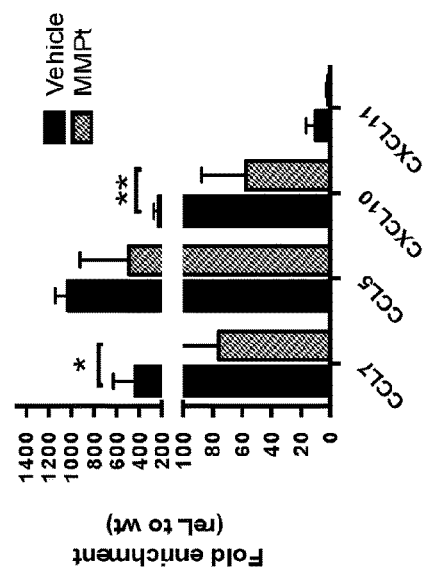

FIG. 23D provides flow cytometry plots showing the percentage of cells expressing the indicated markers after treatment with IFN-γ specific neutralizing antibody or control antibody.

Figure 23G:
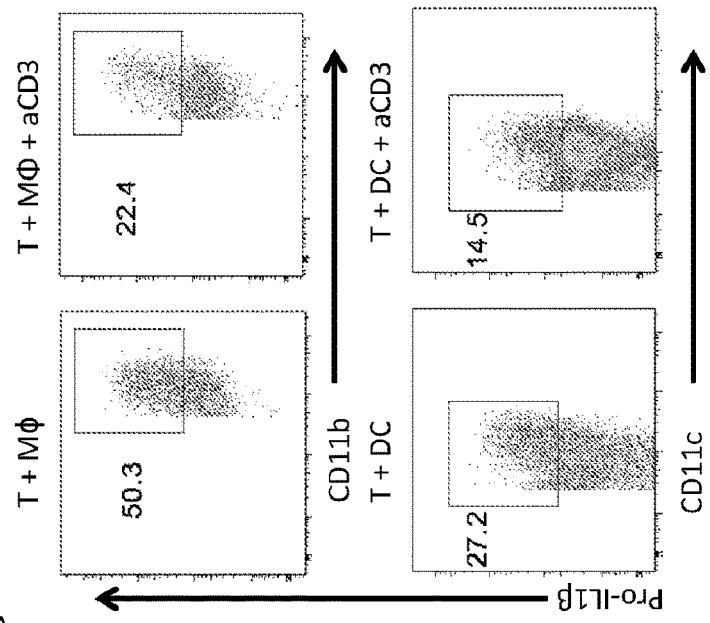
Figure 23E:
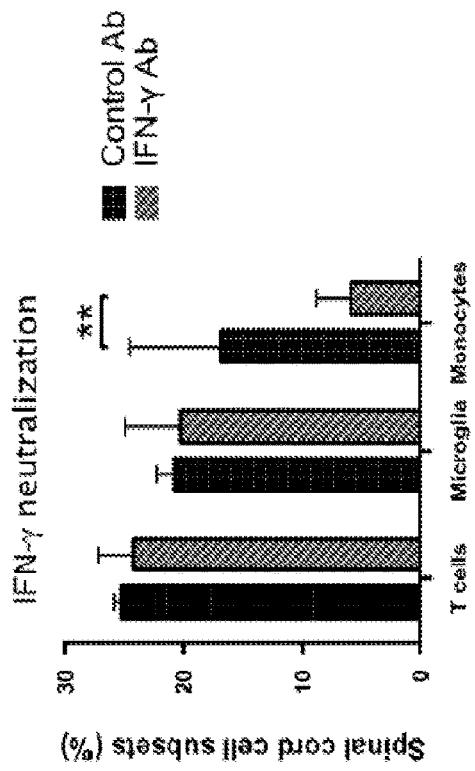

FIG. 23E is a graph showing the spinal cord infiltrating cell subsets as measured by FACS after treatment with IFN-γ specific neutralizing antibody or control antibody. n=3 for each group.

Figure 23F:
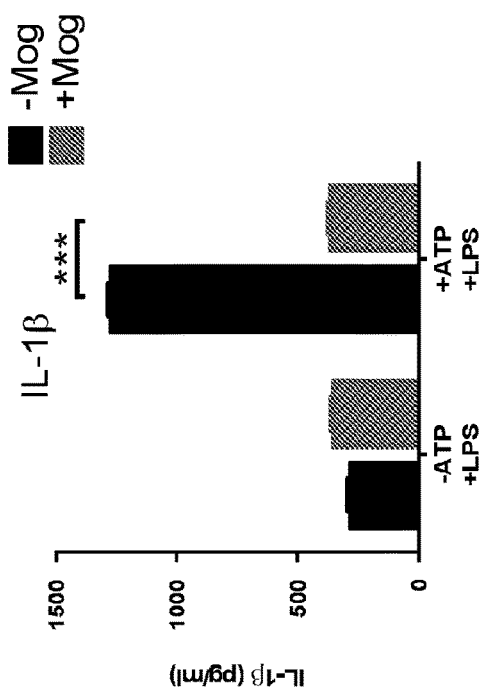

FIG. 23F is a graph showing the ELISA measurement of IL-1beta production by peritoneal macrophages after LPS stimulation in the absence (black bars) or presence (grey striped bars) of in vitro activated MOG-specific T cells restimulated by anti-CD3 for 24 hours. Left 2 bars are without ATP and the right 2 bars are with ATP.

FIG. 23G provides flow cytometry plots showing the percentage of cells expressing the indicated markers in the absence (left panel) or presence (right panels) of anti-CD3 restimulation.

Figure 24:
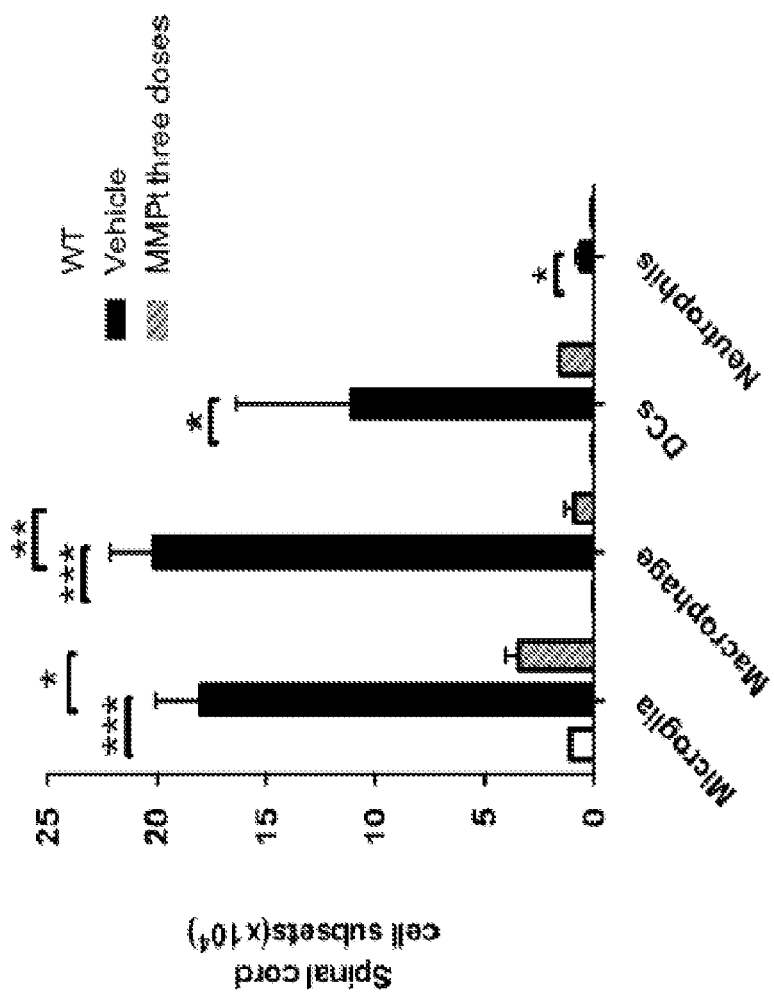

FIG. 24 is a graph showing the total numbers of leukocyte subsets from the spinal cord of EAE mice treated with three doses of 800 µg MMPt i.v. (on day 14 of EAE induction) (solid black bar, n=3), normal mice without EAE induction (open bar, n=2), or EAE mice treated with three doses of vehicle i.v. (grey bar, n=3).

FIG. 25A provides flow cytometry plots showing the percentage of spinal cord infiltrating T cells (CD3+CD45.2+) expressing the indicated markers in EAE mice that were treated with a single dose of normal saline (bottom graphs) or 800 µg MMPt i.v. injections (top graphs) at day 14 of EAE induction.

FIG. 25B is a graph showing the percentages of GM-CSF and IL-10 positive infiltrating T cells in EAE mice treated with vehicle (solid black) or MMPt (striped bars) at day 14 of EAE induction.

FIG. 25C provides a flow cytometry plot showing the percentage of Annexin V positive spinal-cord infiltrating monocytes (gated on CD11b+CD45.2$^{high}$) measured by flow cytometry.

FIG. 25D shows images of TUNEL-stained spinal cord sections from a normal mouse (left), an EAE mouse treated with MMPt (middle), and an EAE mouse treated with normal saline (right). Lower panels provide image enlargements for corresponding framed areas in the upper panels.

Figure 26:
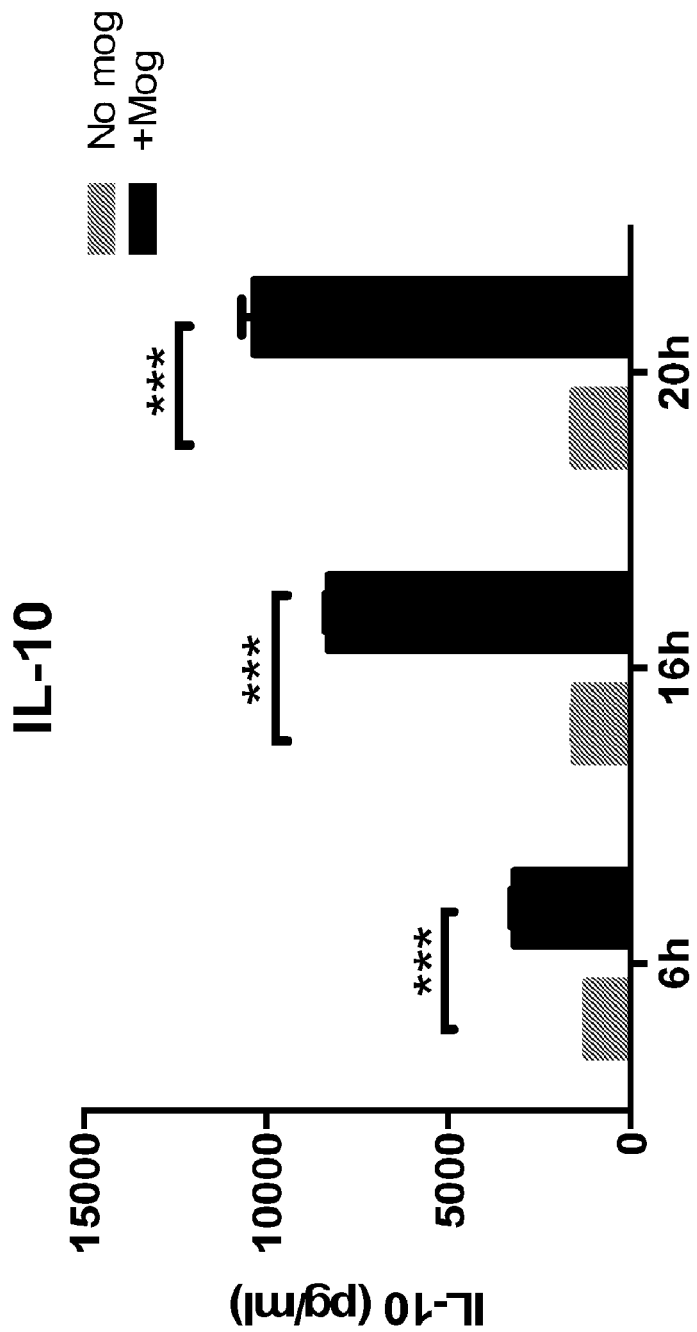

FIG. 26 is a graph showing the levels of IL-10 released in the supernatant of peritoneal macrophages cultured for the times indicated with in vitro activated 2D2 mice T cells restimulated by Mog$_{35-55}$ peptide.

Figure 27A:
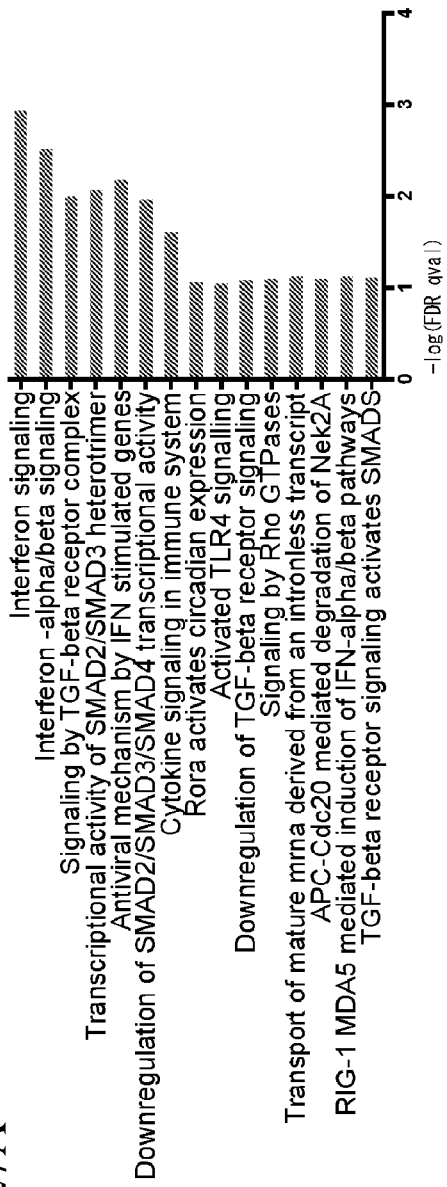

FIG. 27A is a graph showing the top pathways affected by MMPt in mouse spinal cord sorted CD11b+CD45high infiltrating monocytes.

Figure 27C:
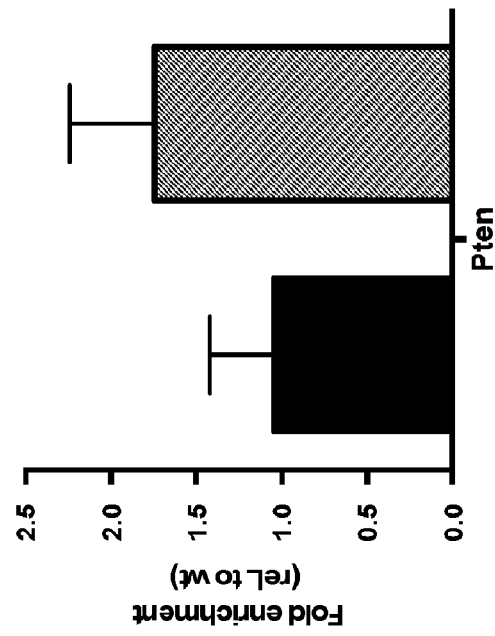
Figure 27B:
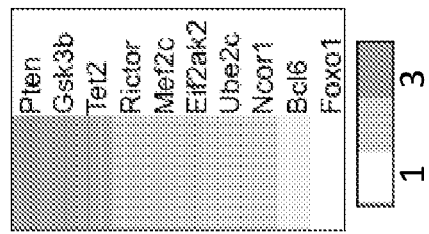

FIG. 27B is a heat map of gene expression, relative to vehicle-treated mice in mouse spinal cord sorted CD11b+CD45high infiltrating monocytes.

FIG. 27C is a graph showing the fold-enrichment of Pten in spinal cord tissues after MMPt single dose treatment (striped bars) or vehicle treatment (black bars) measured by Real-time PCR.

Figure 28A:
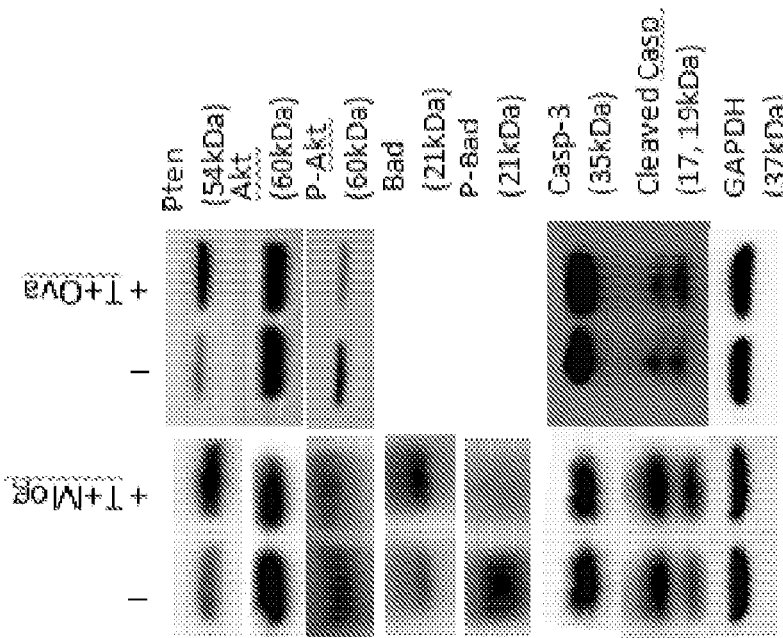

FIG. 28A is a graph showing the fold-enrichment of pro-apoptotic molecules in spinal cord tissue after MMPt treatment (striped bars) or vehicle treatment (black bars) measured by Real-time PCR.

Figure 28B:
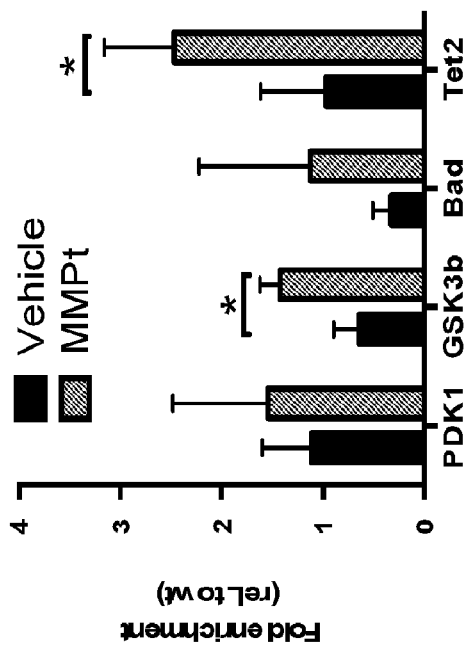

FIG. 28B includes images of Western blots showing Pten, Akt, Bad, and Caspase-3 activation in peritoneal macrophages cultured together with in vitro generated effector 2D2 or DO11.10 T cells restimulated by Mog$_{35-55}$ peptide or OVA$_{323-339}$.

FIG. 29A is a schematic showing the structure of an MMPt protein including truncated MOG, MBP, truncated PLP, a linker, a TEV cleavage sequence, and a histidine tag.

FIG. 29B is an image of an SDS-PAGE electrophoresis gel. Lane 1: Protein standard markers. Lane 2: 5 µg MMPt, under reducing conditions. Lane 3: 5 µg MMPt, under non-reducing conditions.

DETAILED DESCRIPTION OF THE INVENTION

It has been discovered that administration of a combination of MOG, MBP, and PLP autoantigenic protein amino acid sequences may ameliorate one or more of the autoimmune and/or inflammatory aspects of demyelinating disease. Contrary to an expectation that administration of MOG, MBP, and PLP autoantigenic protein amino acid sequences may make one or more of the autoimmune and inflammatory aspects of demyelinating disease more severe, that this combination of autoantigenic protein amino acid sequences, instead, ameliorates one or more of the autoimmune and inflammatory aspects of demyelinating disease is surprising. Without being bound to a particular theory or mechanism, it is believed that the inventive combination of MOG, MBP, and PLP amino acid sequences may induce immunologic tolerance of one or more of MOG, MBP, and PLP. In this regard, the inventive combination of MOG, MBP, and PLP amino acid sequences may provide a tolerogen. Accordingly, it is contemplated that the compositions and methods of the invention may be useful for treating or preventing demyelinating diseases such as, for example, MS.

The compositions and methods of the invention may provide many advantages. For example, the compositions and methods of the invention may provide any one or more of: depletion of one or more of autoimmune T cells, macrophages, dendritic cells, and microglial cells in the spinal cord; decrease of one or more inflammatory cytokines (such as, for example, interferon (IFN)-gamma (γ) and interleukin (IL)-1 beta (β)); induction of restimulation induced cell death (RICD) of autoimmune T cells; increase of apoptotic T cells in the spinal cord; decreased inflammation (e.g., in a rapid manner); remyelination; targeted depletion of autoimmune T cells with little or no depletion of cells other than autoimmune T cells; and little or no side effects. In addition, the inventive MOG, MBP, and PLP autoantigenic protein amino acid sequences are, advantageously, believed to be capable of treating demyelinating disease patients regardless of Major Histocompatibility Complex (MHC) allele expression.

Another embodiment of the invention provides a protein comprising three human autoantigenic proteins, wherein a first human autoantigenic protein comprises a truncated myelin oligodendrocyte glycoprotein (MOG) amino acid sequence, a second human autoantigenic protein comprises a myelin basic protein (MBP) amino acid sequence, and a third human autoantigenic protein comprises a truncated proteolipid protein (PLP) amino acid sequence.

An embodiment of the invention provides a protein comprising no more than three human autoantigenic proteins, wherein a first human autoantigenic protein comprises a truncated myelin oligodendrocyte glycoprotein (MOG) amino acid sequence, a second human autoantigenic protein comprises a myelin basic protein (MBP) amino acid sequence, and a third human autoantigenic protein comprises a truncated proteolipid protein (PLP) amino acid sequence.

Myelin oligodendrocyte glycoprotein (MOG) is a membrane protein expressed on the oligodendrocyte cell surface and the outermost surface of myelin sheaths. MOG is a human autoantigenic protein that is believed to be involved in immune-mediated demyelination. An example of a human MOG cDNA sequence is Genbank Accession No. NM_002433.4 (SEQ ID NO: 23). An example of a full-length human MOG protein ("parent MOG") is Genbank Accession No. NP_002424.3 (SEQ ID NO: 24). An example of a human MOG polymorphism, with respect to SEQ ID NOs: 23 and 24, is c.215C>A; p.P72H. The MOG polymorphism, c.215C>A, is defined herein by reference to SEQ ID NO: 23. Thus, the MOG polymorphism is defined by reference to cDNA ("c."), followed by the particular position in the sequence at which the mutation is taking place, followed by the native nucleotide at that position, followed by the nucleotide with which the native nucleotide is being replaced. With respect to the protein encoded by the polymorphism, p.P72H is defined by reference to SEQ ID NO: 24. Thus, the MOG polymorphism is described herein by reference to protein ("p."), followed by the native amino acid residue being replaced, followed by the particular position in the sequence at which the mutation is taking place.

The truncated MOG amino acid sequence may comprise one or more T cell epitopes and may be a tolerogenic truncated MOG amino acid sequence. The "tolerogenic truncated MOG amino acid sequence" of MOG may include any portion of MOG that includes one or more T cell epitopes and retains tolerogenic activity. In reference to the parent MOG, the tolerogenic truncated MOG amino acid sequence can comprise, for instance, about 10%, about 25%, about 30%, about 50%, about 68%, about 80%, about 90%, about 95%, or more, of the parent MOG. In an embodiment of the invention, the truncated MOG amino acid sequence lacks the hydrophobic domain of the wild-type, full-length MOG amino acid sequence. In an embodiment of the invention, the truncated MOG amino acid sequence includes the p.P72H polymorphism and comprises, consists, or consists essentially of SEQ ID NO: 25. Preferably, the truncated MOG amino acid sequence comprises, consists, or consists essentially of the amino acid sequence of SEQ ID NO: 1. In an embodiment of the invention, the truncated MOG amino acid sequence comprises an amino acid sequence that is at least about 90%, about 91%, about 92%, about 93%, about 94%, about 95%, about 96%, about 97%, about 98%, or about 99% identical to SEQ ID NO: 1 or 25. The truncated MOG amino acid sequence is also referred to herein as "MOG."

Myelin basic protein (MBP) is a major constituent of the myelin sheath of oligodendrocytes and Schwann cells in the nervous system. MBP is a human autoantigenic protein that is also believed to be involved in immune-mediated demyelination. An example of a human MBP cDNA sequence is Genbank Accession No. NM_001025101.1 (SEQ ID NO: 26). An example of a full-length human MBP protein ("parent MBP") is Genbank Accession No. NP_001020272.1 (SEQ ID NO: 27). An example of a human MBP polymorphism, with respect to SEQ ID NOs: 26 and 27, is c.541G>A; p.G181S. The MBP polymorphism, c.541G>A; p.G181S, is defined herein by reference to SEQ ID NO: 26 and SEQ ID NO: 27, respectively, and as described herein with respect to other aspects of the invention.

The MBP amino acid sequence may comprise one or more T cell epitopes and may be a tolerogenic MBP amino acid sequence. While the MBP amino acid sequence may be truncated, preferably, the MBP amino acid sequence is a full-length MBP amino acid sequence. The "tolerogenic truncated MBP amino acid sequence" of MBP may include any portion of MBP that includes one or more T cell epitopes and retains tolerogenic activity. In reference to the parent MBP, the tolerogenic truncated MBP amino acid sequence can comprise, for instance, about 10%, about 25%, about 30%, about 50%, about 68%, about 80%, about 90%, about 95%, or more, of the parent MBP. In an embodiment of the invention, the MBP amino acid sequence includes the p.G181S polymorphism and comprises, consists, or consists essentially of SEQ ID NO: 28. Preferably, the MBP amino acid sequence comprises, consists, or consists essentially of the amino acid sequence of SEQ ID NO: 2. In an embodiment of the invention, the MBP amino acid sequence comprises an amino acid sequence that is at least about 90%, about 91%, about 92%, about 93%, about 94%, about 95%, about 96%, about 97%, about 98%, or about 99% identical to SEQ ID NO: 2 or 28. The MBP amino acid sequence is also referred to herein as "MBP."

Proteolipid protein (PLP) is a transmembrane proteolipid myelin protein that is present in the CNS. PLP is a human autoantigenic protein that is also believed to be involved in immune-mediated demyelination. An example of a human PLP cDNA sequence is Genbank Accession No. NM_000533.3 (SEQ ID NO: 29), and an example of a full-length human PLP protein ("parent PLP") is Genbank Accession No. NP_000524.3 (SEQ ID NO: 30).

The truncated PLP amino acid sequence may comprise one or more T cell epitopes and may be a tolerogenic truncated PLP amino acid sequence. The "tolerogenic truncated PLP amino acid sequence" of PLP may include any portion of PLP that includes one or more T cell epitopes and retains tolerogenic activity. In reference to the parent PLP, the tolerogenic truncated PLP amino acid sequence can comprise, for instance, about 10%, about 25%, about 30%, about 50%, about 68%, about 80%, about 90%, about 95%, or more, of the parent PLP. Preferably, the truncated PLP amino acid sequence comprises, consists, or consists essentially of the amino acid sequence of SEQ ID NO: 3. In an embodiment of the invention, the truncated PLP amino acid sequence comprises an amino acid sequence that is at least about 90%, about 91%, about 92%, about 93%, about 94%, about 95%, about 96%, about 97%, about 98%, or about 99% identical to SEQ ID NO: 3. The truncated PLP amino acid sequence is also referred to herein as "PLP."

An embodiment of the invention provides a single protein comprising any MOG, MBP, and PLP amino acid sequence together in combination. In this regard, an embodiment of the invention provides a protein comprising all of (a) a MOG amino acid sequence at least about 90% identical to SEQ ID NO: 1 or 25; (b) a MBP amino acid sequence at least about 90% identical to SEQ ID NO: 2 or 28; and (c) a PLP amino acid sequence at least about 90% identical to SEQ ID NO: 3. The MOG, MBP, and PLP amino acid sequences may be as described herein with respect to other aspects of the invention. In an embodiment of the invention, the protein comprising MOG, MBP, and PLP comprises, consists, or consists essentially of the amino acid sequence of SEQ ID NO: 9. In an embodiment of the invention, the protein comprising MOG, MBP, and PLP comprises an amino acid sequence that is at least about 90%, about 91%, about 92%, about 93%, about 94%, about 95%, about 96%, about 97%, about 98%, or about 99% identical to SEQ ID NO: 9.

The inventive protein may comprise MOG, MBP, and PLP in any suitable orientation. Examples of orientations of MOG, MBP, and PLP include embodiments wherein (i) the carboxy terminus of PLP is conjugated or fused to the amino terminus of MBP and the carboxy terminus of MBP is conjugated or fused to the amino terminus of MOG; (ii) the carboxy terminus of MBP is conjugated or fused to the amino terminus of MOG and the carboxy terminus of MOG is conjugated or fused to the amino terminus of PLP; (iii) the carboxy terminus of MBP is conjugated or fused to the amino terminus of PLP and the carboxy terminus of PLP is conjugated or fused to the amino terminus of MOG; (iv) the carboxy terminus of MOG is conjugated or fused to the amino terminus of PLP and the carboxy terminus of PLP is conjugated or fused to the amino terminus of MBP; (v) the carboxy terminus of PLP is conjugated or fused to the amino terminus of MOG and the carboxy terminus of MOG is conjugated or fused to the amino terminus of MBP; and (vi) the carboxy terminus of MOG is conjugated or fused to the amino terminus of MBP and the carboxy terminus of MBP is conjugated or fused to the amino terminus of PLP. The conjugation or fusion referred to in all of orientations (i)-(vi) may be directly or through a linker. Of these orientations, (vi) is preferred. In an embodiment of the invention, MBP is conjugated or fused to PLP directly or through a linker.

While any two of MOG, MBP, and PLP may be conjugated or fused directly to one another without any intervening moiety, in a preferred embodiment, any two of MOG, MBP, and PLP are conjugated or fused to one another indirectly through a linker. The linker may be any agent or molecule that connects any two of MOG, PLP and MBP and which is not a human autoantigenic protein (e.g., MOG, MBP, PLP, oligodendrocyte-specific protein (OSP), or myelin-oligodendrocytic basic protein (MOBP)). One of ordinary skill in the art recognizes that sites on MOG, MBP, and PLP, which are not necessary for the function of the inventive protein, may be ideal sites for attaching a linker, provided that the linker, once attached to the inventive protein, do(es) not interfere with the function of the inventive protein, e.g., to induce immunological tolerance or to treat or prevent demyelinating disease. The linker may be capable of forming covalent bonds to two of MOG, MBP, and PLP. Suitable linkers are known in the art and include, but are not limited to, straight or branched-chain carbon linkers, heterocyclic carbon linkers, and peptide linkers. The linker may be joined to amino acids through side groups (e.g., through a disulfide linkage to cysteine). Preferably, the linker is joined to the alpha carbon of the amino and carboxyl groups of the terminal amino acids. In an embodiment of the invention, the linker is a peptide linker comprising the amino acid sequence of SEQ ID NO: 21.

In an embodiment of the invention, the linker is from about three to about eight amino acids in length and consists of glycine and/or serine residues in sequence. Accordingly, the linker may consist of glycine and/or serine residues. In some embodiments, the linker is a peptide of the formula: $(Xaa1)_n$ wherein each Xaa1 is selected independently from glycine and serine and n is an integer from 3 to 8. In a preferred embodiment, the linker is a peptide linker comprising the amino acid sequence of SEQ ID NO: 5.

Any suitable linker may join any two of MOG, MBP, and PLP. Preferably, MOG is conjugated or fused to MBP indirectly through the linker that is from about three to about eight amino acids in length and consists of glycine and/or serine residues in sequence. Preferably, MBP is conjugated or fused to PLP indirectly through the peptide linker comprising the amino acid sequence of SEQ ID NO: 21. In this regard, MBP that is conjugated or fused to PLP indirectly through the linker comprises consists, or consists essentially of the amino acid sequence of SEQ ID NO: 4 or comprises an amino acid sequence that is at least about 90%, about 91%, about 92%, about 93%, about 94%, about 95%, about 96%, about 97%, about 98%, or about 99% identical to SEQ ID NO: 4.

In an embodiment of the invention, the protein comprises a histidine tag. The histidine tag may be useful for purifying the inventive protein in a method of producing the inventive protein. In an embodiment of the invention, the histidine tag is from about 6 to about 12 amino acids in length and consists of histidine residues in sequence. In some embodiments, the histidine tag is a peptide of the formula: $(Xaa2)_m$ wherein each Xaa2 is histidine and m is from 6 to 12. In a preferred embodiment, the histidine tag comprises SEQ ID NO: 8.

In an embodiment of the invention, the protein further comprises a Tobacco Etch Virus (TEV) cleavage sequence. The TEV cleavage sequence may be useful for cleaving the histidine tag from the protein after purification. The TEV cleavage sequence is the recognition site for TEV protease, which specifically recognizes the TEV cleavage sequence and cleaves the protein at the cleavage sequence. In an embodiment of the invention, the TEV cleavage sequence comprises the TEV consensus amino acid sequence of $EX_1LYX_2QX_3$ (SEQ ID NO: 6), wherein $X_1$, $X_2$, and $X_3$ are, independently, any naturally occurring amino acid residue. The cleavage may occur in the TEV consensus sequence between the Gln at position 6 and the $X_3$ at position 7 of SEQ ID NO: 6. Preferably, the TEV cleavage sequence comprises the amino acid sequence of SEQ ID NO: 7.

In an embodiment of the invention, the protein comprises all of MOG, MBP, PLP, a histidine tag, and a TEV cleavage sequence. In this regard, the protein may comprise, consist of, or consist essentially of the amino acid sequence of SEQ ID NO: 10 or comprise an amino acid sequence that is at least about 90%, about 91%, about 92%, about 93%, about 94%, about 95%, about 96%, about 97%, about 98%, or about 99% identical to SEQ ID NO: 10. In another embodiment of the invention, the protein following cleavage comprises all of MOG, MBP, PLP, and the portion of the TEV cleavage sequence that remains following cleavage (e.g., ENLYFQ (SEQ ID NO: 20)), but lacks a histidine tag. In this regard, the protein may comprise, consist of, or consist essentially of the amino acid sequence of SEQ ID NO: 19 or comprise an amino acid sequence that is at least about 90%, about 91%, about 92%, about 93%, about 94%, about 95%, about 96%, about 97%, about 98%, or about 99% identical to SEQ ID NO: 19. In another embodiment of the invention, the protein comprises all of MOG, MBP, and PLP, but lacks both a histidine tag and a TEV cleavage sequence. In this regard, the protein may comprise, consist, or consist essentially of the amino acid sequence of SEQ ID NO: 9 or comprise an amino acid sequence that is at least about 90%, about 91%, about 92%, about 93%, about 94%, about 95%, about 96%, about 97%, about 98%, or about 99% identical to SEQ ID NO: 9.

In an embodiment of the invention, the inventive protein is conjugated or fused to an immunoglobulin Fc region. Without being bound to a particular theory or mechanism, it is believed that conjugation or fusion of the protein to an immunoglobulin Fc region may maintain or increase one or both of the stability and solubility of the protein.

While MOG, MBP, and PLP may be provided in a single protein, an embodiment of the invention provides a composition comprising a mixture of separate MOB, MBP, and PLP proteins. In this regard, an embodiment of the invention provides a composition comprising a mixture of (a) a MOG protein; (b) a MBP protein; and (c) a PLP protein.

Another embodiment of the invention provides a composition comprising a mixture of (a) a MOG protein comprising an amino acid sequence at least about 90% identical to SEQ ID NO: 1 or 25; (b) a MBP protein comprising an amino acid sequence at least about 90% identical to SEQ ID NO: 2 or 28; and (c) a PLP protein comprising an amino acid sequence at least about 90% identical to SEQ ID NO: 3.

Included in the scope of the invention are functional variants of the inventive proteins described herein. The term "functional variant" as used herein refers to a protein having substantial or significant sequence identity or similarity to a parent protein, which functional variant retains the biological activity of the protein of which it is a variant. Functional variants encompass, for example, those variants of the protein described herein (the parent protein) that retain the ability to induce immunological tolerance and/or treat or prevent demyelinating disease to a similar extent, the same extent, or to a higher extent, as the parent protein. In reference to the parent protein, the functional variant can, for instance, be at least about 30%, about 50%, about 75%, about 80%, about 90%, about 91%, about 92%, about 93%, about 94%, about 95%, about 96%, about 97%, about 98%, or about 99% or more identical in amino acid sequence to the parent protein.

The functional variant can, for example, comprise the amino acid sequence of the parent protein with at least one conservative amino acid substitution. Conservative amino acid substitutions are known in the art, and include amino acid substitutions in which one amino acid having certain physical properties, chemical properties, or combinations thereof is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. The protein can consist essentially of the specified amino acid sequence or sequences described herein, such that other components of the functional variant, e.g., other amino acids, do not materially change the biological activity of the functional variant.

Alternatively or additionally, the functional variants can comprise the amino acid sequence of the parent protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent protein.

The protein can consist essentially of the specified amino acid sequence or sequences described herein, such that other components of the functional variant, e.g., other amino acids, do not materially change the biological activity of the functional variant. In this regard, the inventive protein can, for example, consist essentially of the amino acid sequence of any one of SEQ ID NOs: 1 (or 25), 2 (or 28), 3-4, 9-10, and 19. Also, for instance, the inventive proteins can consist essentially of the amino acid sequence(s) of all of SEQ ID NOs: 1-3, all of SEQ ID NOs: 25 and 2-3, all of SEQ ID NOs: 1, 28, and 3, all of SEQ ID NOs: 25, 28, and 3, both of SEQ ID NOs: 1 and 4, or both of SEQ ID NOs: 25 and 4.

The proteins of the invention can be of any length, i.e., can comprise any number of amino acids, provided that the proteins retain their biological activity, e.g., the ability to induce immunological tolerance and/or treat or prevent demyelinating disease. For example, the protein can be 50 to 5000 amino acids long, such as 50, 70, 75, 100, 125, 150, 175, 200, 300, 400, 500, 600, 700, 800, 900, 1000 or more amino acids in length. In this regard, the proteins of the invention also include oligopeptides.

The proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The proteins of the invention can be obtained by methods known in the art. Suitable methods of de novo synthesizing proteins are known in the art. Alternatively, the proteins described herein can be commercially synthesized by companies, such as Synpep (Dublin, Calif.), Peptide Technologies Corp. (Gaithersburg, Md.), and Multiple Peptide Systems (San Diego, Calif.). In this respect, the inventive proteins can be synthetic, recombinant, isolated, purified, or combinations thereof.

An embodiment of the invention provides a method of producing the protein, the method comprising (a) recombinantly expressing the protein in a host cell; (b) lysing the host cell to produce a mixture comprising the protein and cellular components; and (c) purifying the protein from the cellular components.

The method comprises recombinantly expressing the protein in a host cell. Recombinantly expressing the protein in a host cell may be carried out using the nucleic acids described herein using standard recombinant methods. See, for instance, Green et al. (eds.), *Molecular Cloning, A Laboratory Manual*, 4th Edition, Cold Spring Harbor Laboratory Press, New York (2012).

The method comprises lysing the host cell to produce a mixture comprising the protein and cellular components. Lysing the host cell to produce a mixture comprising the protein and cellular components may also be carried out using standard methods. For example, the cells may be lysed by any one or more of mechanical disruption, liquid homogenization, high frequency sound waves, freeze/thaw cycles and manual grinding.

The method comprises purifying the protein from the cellular components. Purifying may be carried out in any suitable manner. For example, in an embodiment wherein the polypeptide comprises a histidine tag, as described herein with respect to other aspects of the invention, (also referred to herein as "histidine-tagged protein(s)"), purifying the protein may comprise contacting a metal-chelate support with the protein and cellular components, binding the histidine tag of the protein to the metal-chelate support, eluting the protein from the metal-chelate support, and separating the protein from the cellular components.

Contacting a metal-chelate support with the protein and cellular components may be carried out in any suitable manner. The metal-chelate support may be any metal-chelate support known in the art that is suitable for separation by immobilized metal affinity chromatography (IMAC). For example, the metal-chelate support may be beaded agarose or magnetic particles that are derivatized with chelating groups to immobilize a metal ion. Suitable exemplary supports that are commercially available include SEPHAROSE beads (Sigma-Aldrich, St. Louis, Mo.). The chelator may be, for example, nitrilotriacetic acid (NTA) or iminodiacetic acid (IDA). Once the derivatized support is prepared, it can be "loaded" with any suitable divalent metal (e.g., Ni or Co).

Contacting a metal-chelate support with the protein and cellular components and binding the histidine tag of the protein to the metal-chelate support may be carried out in any suitable manner known in the art. The method may comprise physically contacting the metal-chelate support with the protein and cellular components, such that the histidine-tagged protein binds to the metal-chelate support.

The method may comprise separating the cellular components from the histidine-tagged proteins. Separating the cellular components from the histidine-tagged proteins may be carried out in any suitable manner and may include physically separating the cellular components from the histidine-tagged proteins. Separating cellular components from the histidine-tagged proteins may be carried out by binding the histidine-tagged proteins to the metal-chelate support while not binding the cellular components to the metal-chelate support. In an embodiment, components that lack a histidine tag (e.g., cellular components) will not bind to the metal-chelate support. The cellular components may be removed from the metal-chelate support (and the histidine-tagged proteins bound to the metal-chelate support) in any suitable manner, e.g., by washing the metal-chelate support with a suitable buffer, for example, a near-neutral buffer (physiologic pH and ionic strength). An example of a suitable buffer for washing and binding is Tris-buffer saline (TBS) pH 7.2, containing 10-25 mM imidazole. The method may comprise removing the components that lack a histidine tag (e.g., cellular components) and which are not bound to the metal-chelate support from the histidine-tagged proteins.

The method comprises eluting the histidine-tagged proteins from the metal-chelate support to produce purified histidine-tagged proteins. Eluting the histidine-tagged protein particles from the metal-chelate support may be carried out in any suitable manner. In an embodiment, eluting the histidine-tagged proteins from the metal-chelate support may be carried out by contacting the metal-chelate support with elution buffer. An example of a suitable elution buffer is a high concentration of imidazole (at least 200 mM), low pH (e.g., 0.1M glycine-HCl, pH 2.5). The method may comprise displacing the histidine-tagged proteins with the elution buffer to produce an eluent comprising purified histidine-tagged proteins. The eluent comprising purified histidine-tagged proteins contains no cellular components or fewer cellular components as compared to that contained in the mixture of cellular components and histidine-tagged proteins.

In an embodiment of the invention, the method further comprises separating the protein from further cellular components by gel filtration chromatography. Suitable substrates for carrying out gel filtration chromatography are commercially available and may include, for example, a HILOAD 2%0 SUPERDEX gel filtration chromatography column (GE Healthcare). Separation of the protein from further cellular components by gel filtration chromatography may be carried out using techniques known in the art. For example, the method may comprise contacting the eluent comprising purified histidine-tagged proteins obtained by IMAC (as described herein with respect to other aspects of the invention) with a gel filtration chromatography substrate, separating the histidine-tagged protein from further cellular components, and recovering the purified histidine-tagged protein.

In an embodiment of the invention, the method further comprises separating the protein from further cellular components by ion-exchange chromatography. Suitable substrates for carrying out ion-exchange chromatography are commercially available and may include, for example, a POROS HS 50 μM column (Life Technologies). Separation of the protein from further cellular components by ion-exchange chromatography may be carried out using techniques known in the art. For example, the method may comprise contacting the purified histidine-tagged proteins obtained by gel filtration chromatography (as described herein with respect to other aspects of the invention) with an ion-exchange chromatography substrate, separating the histidine-tagged protein from further cellular components, and recovering the purified histidine-tagged protein.

In an embodiment of the invention, the method further comprises cleaving the protein after purifying the protein. Cleaving the protein may be carried out in any suitable manner. For example, the method may comprise cleaving the histidine tag from the protein. In an embodiment wherein the protein comprises a TEV cleavage sequence, the method may comprise contacting the histidine-tagged protein with an enzyme that cleaves at the TEV cleavage sequence (e.g., TEV protease). Contacting the histidine-tagged protein may comprise physically contacting the histidine-tagged protein with the enzyme under conditions that allow the enzyme to cleave the histidine tag from the protein at the TEV cleavage sequence.

Another embodiment of the invention provides a nucleic acid comprising a nucleotide sequence encoding any of the proteins described herein. In an embodiment, the nucleic acid comprises a nucleotide sequence encoding MOG comprising SEQ ID NO: 11. In an embodiment, the nucleic acid comprises a nucleotide sequence encoding MBP comprising SEQ ID NO: 12. In an embodiment, the nucleic acid comprises a nucleotide sequence encoding PLP comprising SEQ ID NO: 13. In an embodiment, the nucleic acid comprises a nucleotide sequence encoding MBP that is conjugated or fused to PLP indirectly through a linker, the nucleotide sequence comprising SEQ ID NO: 14. In an embodiment, the nucleic acid comprises a nucleotide sequence encoding a linker comprising SEQ ID NO: 15 or 22. In an embodiment, the nucleic acid comprises a nucleotide sequence encoding a TEV cleavage sequence comprising SEQ ID NO: 16. In an embodiment, the nucleic acid comprises a nucleotide sequence encoding a histidine tag comprising SEQ ID NO: 17. Preferably, the nucleic acid comprises a nucleotide sequence comprising all of SEQ ID NOs: 11-13 or both of SEQ ID NO: 11 and 14. In an especially preferred embodiment, the nucleic acid comprises a nucleotide sequence comprising all of SEQ ID NOs: 11, 14, and 15-17. In this regard, a nucleic acid comprising a nucleotide sequence encoding all MOG, MBP, PLP, a linker, a TEV cleavage sequence, and a histidine tag comprises the nucleotide sequence of SEQ ID NO: 18.

The term "nucleic acid," as used herein, includes "polynucleotide," "oligonucleotide," and "nucleic acid molecule," and generally means a polymer of DNA or RNA, which can be single-stranded or double-stranded, which can be synthesized or obtained (e.g., isolated, purified, or both isolated and purified) from natural sources, which can contain natural, non-natural or altered nucleotides, and which can contain a natural, non-natural, or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, substitutions, or combinations thereof. However, it may be suitable in some instances, as discussed herein, for the nucleic acid to comprise one or more insertions, deletions, inversions, substitutions, or combinations thereof.

Preferably, the nucleic acids of the invention are recombinant. As used herein, the term "recombinant" refers to (i) molecules that are constructed outside living cells by joining natural or synthetic nucleic acid segments, or (ii) molecules that result from the replication of those described in (i) above. For purposes herein, the replication can be in vitro replication or in vivo replication.

The nucleic acids can be constructed based on chemical synthesis, enzymatic ligation reactions, or combinations thereof using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches, from a random sequence that happened to have only a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt conditions, high temperature conditions, or combinations thereof, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive proteins. It is generally appreciated that conditions can be rendered more stringent by the addition of increasing amounts of formamide.

The invention also provides a nucleic acid comprising a nucleotide sequence that is about 70% or more, e.g., about 80% or more, about 90% or more, about 91% or more, about 92% or more, about 93% or more, about 94% or more, about 95% or more, about 96% or more, about 97% or more, about 98% or more, or about 99% or more identical to any of the nucleic acids described herein.

In some embodiments, the nucleotide sequence may be codon-optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. Nucleotide SEQ ID NOs: 11-18 and 22 described herein advantageously comprise codon-optimized sequences. In an embodiment of the invention, the nucleotide sequence is codon-optimized for eukaryotic or prokaryotic expression. In this regard, the inventive protein may be expressed by any suitable cell, e.g., bacterial cells, plant cells (e.g., tobacco plant cells), or mammalian cells (e.g., human cells or Chinese hamster ovary (CHO) cells).

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, which can be synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do(es) not hinder the transcription or replication of the vector.

The recombinant expression vector of the invention can be any suitable recombinant expression vector, and can be used to transform or transfect any suitable host cell. Suitable vectors include those designed for propagation and expansion or for expression or for both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). Preferably, the recombinant expression vector is a bacterial vector, e.g., a plasmid.

The recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColEl, 2µ, plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive protein, or to the nucleotide sequence which is complementary to or which hybridizes to the nucleotide sequence encoding the protein. The selection of promoters, e.g., strong, weak, inducible, tissue-specific, and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell, an adherent cell or a suspended cell, i.e., a cell that grows in suspension. For purposes of producing a recombinant inventive protein, the host cell is preferably a prokaryotic cell, e.g., an E. coli cell.

Also provided by the invention is a population of cells comprising at least one host cell described herein. The population of cells can be a heterogeneous population comprising the host cell comprising any of the recombinant expression vectors described, in addition to at least one other cell, e.g., a host cell which does not comprise any of the recombinant expression vectors. Alternatively, the population of cells can be a substantially homogeneous population, in which the population comprises mainly (e.g., consisting essentially of) host cells comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population of host cells comprising a recombinant expression vector as described herein.

The inventive proteins, nucleic acids, recombinant expression vectors, host cells, and populations of cells can be isolated, purified, or both isolated or purified. The term "isolated" as used herein means having been removed from its natural environment. The term "purified" as used herein means having been increased in purity, wherein "purity" is a relative term, and not to be necessarily construed as absolute purity. For example, the purity can be about 50% or more, about 60% or more, about 70% or more, about 80% or more, about 90% or more, or about 100%. The purity preferably is about 90% or more (e.g., about 90% to about 95%) and more preferably about 98% or more (e.g., about 98% to about 99%).

The inventive proteins, nucleic acids, recombinant expression vectors, host cells, and populations of cells, all of which are collectively referred to as "inventive MMPt materials" hereinafter, can be formulated into a composition, such as a pharmaceutical composition. In this regard, the invention provides a pharmaceutical composition comprising any of the proteins, nucleic acids, recombinant expression vectors, host cells, and populations of cells described herein, and a pharmaceutically acceptable carrier. The inventive pharmaceutical composition containing any of the inventive MMPt materials can comprise more than one inventive MMPt material, e.g., a protein and a nucleic acid. Alternatively, the pharmaceutical composition can comprise an inventive MMPt material in combination with one or more other pharmaceutically active agents or drugs, such as immunosuppressive compounds, e.g., cyclosporine A (CsA), FK506, pentostatin, cyclophosphamide, and tofacitinib, etc. Preferably, the immunosuppressive compound is CsA.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive MMPt material, as well as by the particular method used to administer the inventive MMPt material. Accordingly, there are a variety of suitable formulations of the pharmaceutical composition of the invention. The following formulations for parenteral (e.g., subcutaneous, intravenous (i.v.), intraarterial, intramuscular, intradermal, interperitoneal, and intrathecal) and oral administration are exemplary and are in no way limiting. More than one route can be used to administer the inventive MMPt materials, and in certain instances, a particular route can provide a more immediate and more effective response than another route.

Formulations suitable for oral administration can include (a) liquid solutions, such as an effective amount of the inventive MMPt material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive MMPt material in a flavor, usually sucrose and acacia or tragacanth, as well as pastilles comprising the inventive MMPt material in an inert base, such as gelatin and glycerin, or sucrose and acacia, emulsions, gels, and the like additionally containing such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive MMPt material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.1% to about 5% by weight of the inventive MMPt material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. The requirements for effective pharmaceutical carriers for parenteral compositions are well-known to those of ordinary skill in the art.

It will be appreciated by one of skill in the art that, in addition to the above-described pharmaceutical compositions, the inventive MMPt materials of the invention can be formulated as inclusion complexes, such as cyclodextrin inclusion complexes, or liposomes.

For purposes of the invention, the amount or dose of the inventive MMPt material administered should be sufficient to effect a desired response, e.g., a therapeutic or prophylactic response, in the mammal over a reasonable time frame. For example, the dose of the inventive MMPt material should be sufficient to induce immunological tolerance of one or more of MOG, MBP, and PLP or treat or prevent a demyelinating disease (e.g., demyelinating disease progression) in a period of from about 2 hours or longer, e.g., 12 to 24 or more hours, from the time of administration. In certain embodiments, the time period could be even longer. The dose will be determined by the efficacy of the particular inventive MMPt material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of signs of disease), $LD_{50}$ (the dose lethal to 50% of the population), the $ED_{50}$ (the dose therapeutically effective in 50% of the population), and the therapeutic index in cell culture, animal studies, or combinations thereof. The therapeutic index is the ratio of $LD_{50}$ to $ED_{50}$ (i.e., $LD_{50}/ED_{50}$).

The dose of the inventive MMPt material also may be determined by the existence, nature, and extent of any adverse side effects that might accompany the administration of a particular inventive MMPt material. Typically, the attending physician will decide the dosage of the inventive MMPt material with which to treat each individual patient, taking into consideration a variety of factors, such as age, body weight, general health, diet, sex, inventive MMPt material to be administered, route of administration, and the severity of the condition being treated. By way of example and not intending to limit the invention, the dose of the inventive MMPt material can be about 0.001 to about 1000 mg/kg body weight of the subject being treated/day, from about 0.01 to about 10 mg/kg body weight/day, about 0.01 mg to about 1 mg/kg body weight/day, from about 1 to about to about 1000 mg/kg body weight/day, from about 5 to about 500 mg/kg body weight/day, from about 10 to about 250 mg/kg body weight/day, about 25 to about 150 mg/kg body weight/day, about 8 to about 32 mg/kg body weight/day, about 10 mg/kg body weight/day, about 2 mg/kg body weight/day to about 5 mg/kg body weight/day, or about 4 mg/kg body weight/day. Alternatively, the inventive MMPt materials can be modified into a depot form, such that the manner in which the inventive MMPt material is released into the body to which it is administered is controlled with respect to time and location within the body. Depot forms of inventive MMPt materials can be, for example, an implantable composition comprising the inventive MMPt materials and a porous or non-porous material, such as a polymer, wherein the inventive MMPt materials is encapsulated by or diffused throughout the material, degradation of the non-porous material, or combinations thereof. The depot is then implanted into the desired location within the body and the inventive MMPt materials are released from the implant at a predetermined rate.

It is contemplated that the inventive pharmaceutical compositions, proteins, nucleic acids, recombinant expression vectors, host cells, or populations of cells can be used in methods of treating or preventing a demyelinating disease. In this regard, the invention provides a method of treating or preventing a demyelinating disease in a mammal comprising administering to the mammal any of the proteins, nucleic acids, recombinant expression vectors, host cells, populations of cells, or pharmaceutical compositions described herein, in an amount effective to treat or prevent the demyelinating disease in the mammal. In an embodiment of the invention, the demyelinating disease is an autoimmune-mediated demyelinating disease, for example, a demyelinating disease that arises due to primary and/or secondary autoimmune processes. The demyelinating disease can be, for example, multiple sclerosis (MS), autoimmune inflammatory deymyelinating optic neuritis, Devic's disease (neuromyelitis optica), transverse myelitis, acute MS (Marburg variant), Balo's concentric sclerosis, autoimmune mediated Guillain-Barré syndrome, acute disseminated encephalomyelitis (ADEM), or adrenomyeloneuropathy. In a preferred embodiment, the demyelinating disease is MS.

An embodiment of the invention provides a method of treating or preventing autoimmune inflammatory myelitis in a mammal comprising administering to the mammal any of the proteins, nucleic acids, recombinant expression vectors, host cells, populations of cells, or pharmaceutical compositions described herein, in an amount effective to treat or prevent the autoimmune inflammatory myelitis in the mammal. An embodiment of the invention provides a method of treating or preventing demyelination in a mammal comprising administering to the mammal any of the proteins, nucleic acids, recombinant expression vectors, host cells, populations of cells, or pharmaceutical compositions described herein, in an amount effective to treat or prevent the demyelination in the mammal.

In an embodiment of the invention, administering the inventive protein or composition to the mammal increases expression of one or more monocyte genes selected from the group consisting of IL10, IL18, IL23a, IL1b, Tnf, Ifnb1, CCl2, CCl3, CCl4, Ccr2, Pten, Gsk3b, Tet2, Rictor, Mef2c, Elf2ak2, Ube2c, Bcl6, and Ncor1 in spinal cord tissue of the mammal.

In an embodiment of the invention, administering the protein or composition to the mammal decreases expression of one or more genes selected from the group consisting of Ccl8, Ccl6, Ccl9, Ccl17, and Ccl9 in spinal cord tissue of the mammal.

In an embodiment of the invention, administering the protein or composition to the mammal decreases proliferation of one or both of macrophages and monocytes in spinal cord tissue of the mammal.

In an embodiment of the invention, administering the protein or composition to the mammal remyelinates axons in spinal cord tissue of the mammal.

Experimental Autoimmune Encephalomyelitis (EAE) is an acute or chronic-relapsing, acquired, inflammatory, and demyelinating autoimmune disease model (see, e.g., Wekerle et al., *Ann. Neurol.*, 36: S47-S53 (1994); Goverman et al., *Lab Anion. Sci.*, 46: 482-92 (1996); Bischof et al., *Proc. Natl. Acad. Sci. USA*, 98: 12168 (2001)). In the model, the animal is injected with whole (or parts of) various proteins that make up myelin, the insulating sheath that surrounds nerve cells (neurons). Several proteins or parts of proteins (antigens) can be used to induce EAE, including MBP, PLP, and MOG. These proteins induce an autoimmune response in the animal, such that the animal's immune system mounts an attack on its own myelin as a result of exposure to the injection. As a result, the animal develops a disease process that closely resembles MS, particularly in humans. It has been surprisingly found that administering a combination of MOG, MBP, and PLP stops or slows the progression of EAE and/or prevents EAE from occurring.

Any suitable mammal can be used in the EAE model, such as mice, rats, guinea pigs, rabbits, macaques, rhesus monkeys, and marmosets. Rodents, such as mice and rats, are particularly preferred given the resemblance of the induced disease to MS in humans.

In an embodiment of the invention, the method further comprises co-administering an immunosuppressive compound to the mammal. The immunosuppressive compound may be as described herein with respect to other aspects of the invention. The method may comprise administering the inventive MMPt material and the immunosuppressive compound simultaneously or sequentially to the mammal. In an embodiment of the invention, the method comprises administering the immunosuppressive compound to the mammal prior to administering the inventive MMPt material or administering the inventive MMPt material after administering the immunosuppressive compound to the mammal. In another embodiment, the method comprises administering the inventive MMPt material to the mammal prior to administering the immunosuppressive compound or administering the immunosuppressive compound after administering the inventive MMPt material to the mammal. Preferably, the method comprises administering the inventive MMPt material and the immunosuppressive compound simultaneously to the mammal, e.g., in a single pharmaceutical composition.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of a demyelinating disease in a mammal. Furthermore, the treatment or prevention provided by the inventive method can include treatment or prevention of one or more conditions, symptoms, or signs of the demyelinating disease, e.g., MS, being treated or prevented. Also, for purposes herein, "prevention" can encompass delaying the onset of the disease, or a symptom, sign, or condition thereof.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates a method of producing a protein comprising no more than three human autoantigenic proteins, wherein a first human autoantigenic protein comprises a truncated MOG amino acid sequence, a second human autoantigenic protein comprises a full-length MBP amino acid sequence, and a third human autoantigenic protein comprises a truncated PLP amino acid sequence.

*Escherichia coli* cells were transduced with a recombinant expression vector comprising the nucleotide sequence of SEQ ID NO: 18, which encoded a protein comprising a truncated MOG amino acid sequence, a full-length MBP amino acid sequence, and a truncated PLP amino acid sequence. The carboxyl terminus of MOG was conjugated to the amino terminus of MBP with a linker comprising the amino acid sequence of SEQ ID NO: 5 positioned between MOG and MBP. The carboxyl terminus of MPB was conjugated directly to the amino terminus of PLP with a linker comprising the amino acid sequence of SEQ ID NO: 21 positioned between MBP and PLP. The protein further comprised a histidine tag SEQ ID NO: 8 that was conjugated to the carboxyl terminus of PLP with a TEV cleavage sequence (SEQ ID NO: 7) positioned between PLP and the histidine tag. The full length protein encoded by the vector, including the truncated MOG amino acid sequence, the MBP amino acid sequence, the truncated PLP amino acid sequence, the linkers SEQ ID NO: 5 and 21, the histidine tag, and the TEV cleavage sequence, comprised the amino acid sequence of SEQ ID NO: 10 (also referred to herein as "MOG MBP PLP tolerogen (MMPt)" or "MMPt protein"). A schematic showing the structure of MMPt is shown in FIG. 29A.

The protein was expressed in the cells. The cells were lysed to produce a mixture comprising the protein and cellular components. The protein was purified from the cellular components using the histidine tag. Cell pellets were resuspended in 1 L of extraction buffer (20 mM Tris-HCl, 7M guanidine hydrochloride, 20 mM b-mercaptoethanol, pH 8.0) via sonication and vigorous trituration. The mixture was then centrifuged at 24,000 revolutions per minute (rpm) for 20 minutes (min), and the supernatant was immediately put on ice. The extraction step was repeated five times to ensure the full recovery of MMPt from insoluble pellets, and the combined supernatants were filtered through a 0.22 mm Millipore Express PLUS membrane (Millipore, Billerica, Mass.). After filtration, the sample was applied to a $Ni_{2+}$—chelating Sepharose FAST FLOW (GE Healthcare, Little Chalfont, UK) column (50/80) and washed with at least five column volumes of the washing buffer (20 mM Tris-HCl, 300 mM NaCl, 20 mM imidazole, 8 M urea, pH 8.0). The MMPt protein was subsequently eluted with 500 mL of elution buffer (20 mM Tris-HCl, 300 mM NaCl, 300 mM imidazole, 8M urea, pH 8.0) while monitoring optical density (OD) at 280 nm. Additional β-mercaptoethanol was then added to the elution fraction to increase the concentration of the reductant to 20 mM.

MMPt was subsequently applied to a HILOAD 26/60 SUPERDEX 75 pg column (GE Healthcare) equilibrated in equilibration buffer (20 mM Tris-HCl, 20 mM imidazole, 7 M guanidine hydrochloride, 20 mM β-mercaptoethanol, pH 8.0) with a flow rate of 3.0 mL/min while monitoring OD at 280 nm. The MMPt fraction eluted from the SUPERDEX 75 column (confirmed by SDS-PAGE) was subsequently applied to a POROS 50HS column (Life Technologies, Carlsbad, Calif.) (26/10) equilibrated in buffer A (5% acetonitrile, 0.1% TFA) with a flow rate of 4.0 mL/min. The bound MMPt was then eluted with a linear gradient (20 column volumes from 30% to 60%) of buffer B (60% acetonitrile, 0.1% TFA) and lyophilized.

The purity of the protein was greater than 80%, as measured by sodium dodecyl sulfate polyacrylamide gel electrophoresis (SDS-PAGE). SDS-PAGE showed that the protein had the expected molecular weight of 58 kDa (FIG. 29B). The endotoxin level was measured to be less than one endotoxin unit (EU), as measured by the limulus amebocyte lysate (LAL) method.

Example 2

This example demonstrates that MMPt induces restimulation-induced cell death (RICD) in vitro.

Figure 1B:
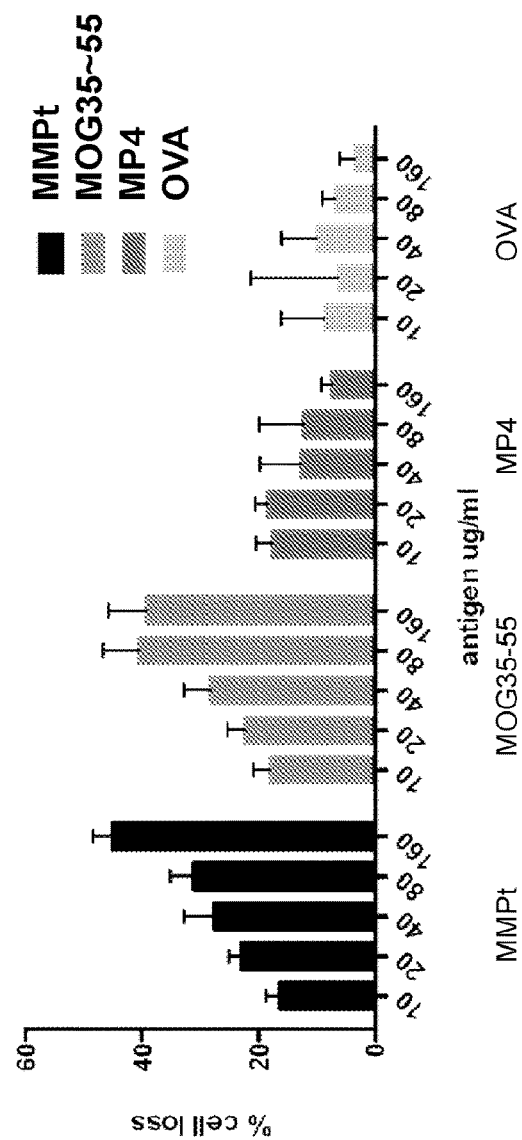
FIG. 1B is a graph showing the percent of T cells lost (% cell loss) upon culture of T cells in the presence of various concentrations of MMPt (SEQ ID NO: 19), $MOG_{35-55}$ (SEQ ID NO: 31), MP4 (SEQ ID NO: 4), or ovalbumin (OVA) (µg/ml).
Figure 1A:
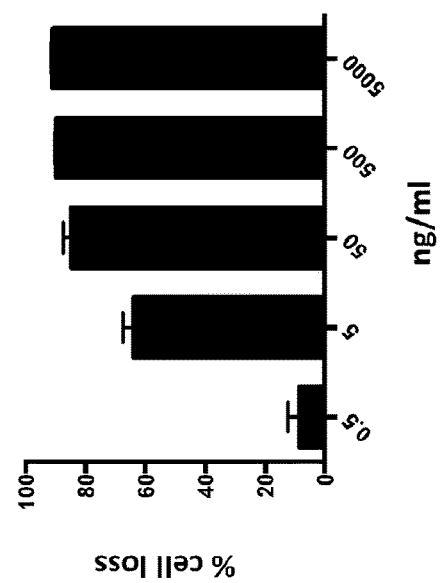
FIG. 1A is a graph showing the percent of T cells lost (% cell loss) upon culture of T cells in the presence of various concentrations of an anti-CD3 antibody.

2D2 T cell receptor (TCR) transgenic mice develop spontaneous diseases similar in incidence and manifestation to those developed by MS patients. Activated T cells from 2D2 TCR transgenic mice were cultured in the presence of an anti-CD3 antibody and various concentrations of MMPt (SEQ ID NO: 10). The percentage of T cell loss was measured. The results are shown in FIG. 1A. A shown in FIG. 1A, a T cell loss of at least about 60% was measured upon stimulation with MMPt and anti-CD3 at the MMPt concentrations of 5 ng/ml and higher.

Activated and cycling (e.g., proliferating) T cells from 2D2 TCR transgenic mice were cultured for 48 hours in the presence of various concentrations of MMPt protein (SEQ ID NO: 10), $MOG_{35-55}$ peptide (MEVGWYRSPFSRVVH-LYRNGK) (SEQ ID NO: 31), MBP and PLP with the linker of SEQ ID NO: 21 positioned between them ("MP4 protein") (SEQ ID NO: 4), or ovalbumin protein (OVA). The percentage of T cell loss was measured. The results are shown in FIG. 1B. As shown in FIG. 1B, a T cell loss of over 40% was observed upon co-culture with MMPt (SEQ ID NO: 10) at a concentration of 160 µg/ml.

Example 3

This example demonstrates that MMPt impedes the progression of disease in MOG-induced EAE.

Female C57BL/6 mice (10 weeks old) were subcutaneously (SC) immunized with $MOG_{35-55}$ peptide (SEQ ID NO: 31) (200 ng/dose) on Days 0 and 1. On Day 10, the mice began to show signs of the early stages of EAE. Mice were retro-orbitally injected twice daily on Days 8, 10, and 12 with normal saline (NS) (Group A), MMPt at a dose of 800 µg/day (Group B), or MP4 at a dose of 800 µg/day (Group C). Mean clinical scoring was determined for up to 23 days after immunization. Clinical scoring was carried out as follows:

Score 0, healthy;
Score 1, flaccid tail;
Score 1.5, flaccid tail and impaired righting reflex;
Score 2, impaired righting reflex and hind limb weakness;
Score 2.5, one hind leg paralyzed;
Score 3, both hind legs paralyzed with residual mobility in both legs;
Score 3.5, both hind legs completely paralyzed;
Score 4, both hind legs completely paralyzed and beginning front limb paralysis;
Score 5, moribund or death of the animal after preceding clinical disease.

Figure 2:
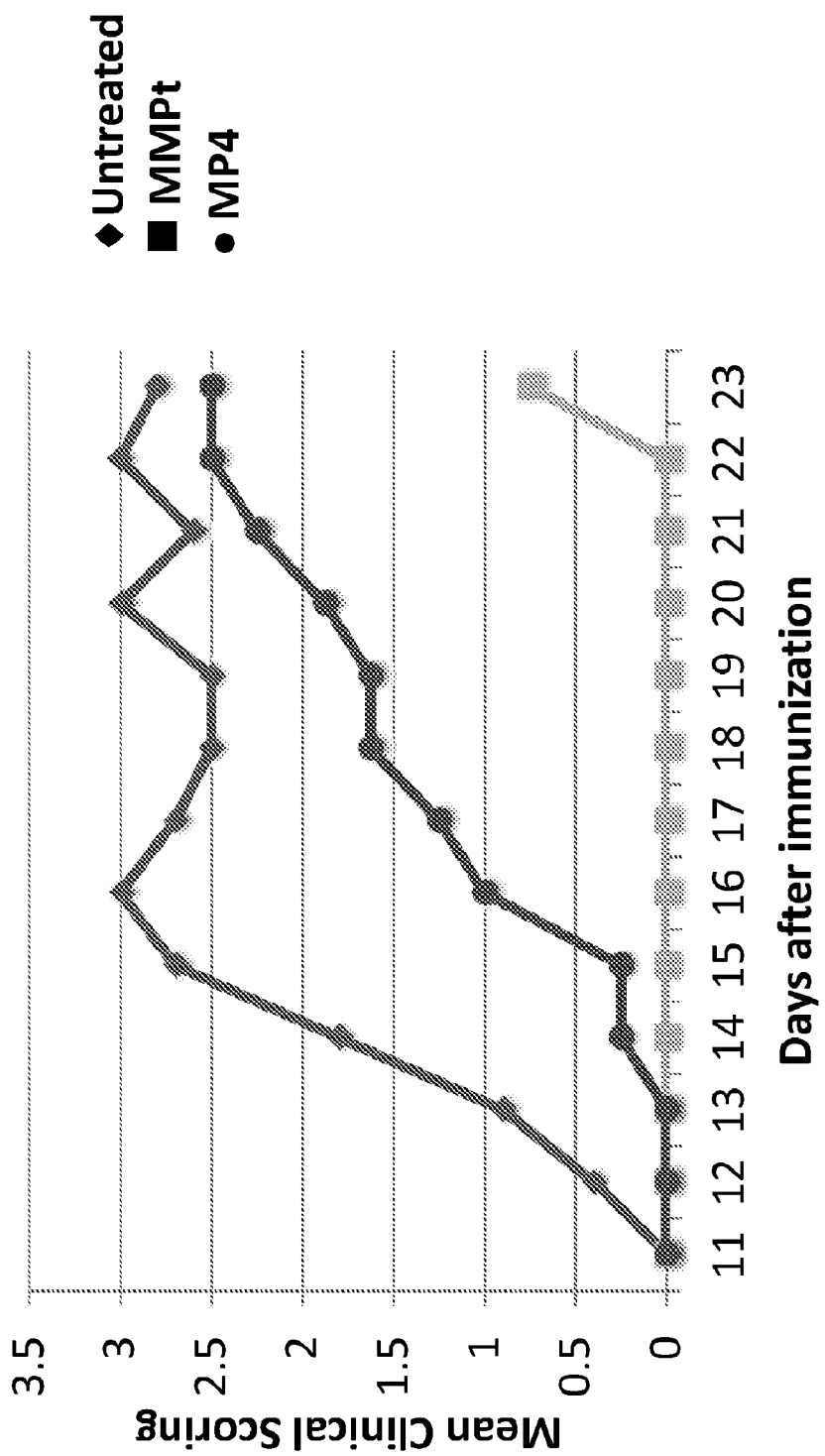
FIG. 2 is a graph showing the mean clinical scoring of mice with MOG-induced EAE that were untreated (diamonds) or treated with 800 µg of MMPt (SEQ ID NO: 19) (squares) or 800 µg of MP4 (circles) at various days after immunization.

The results are shown in FIG. 2. As shown in FIG. 2, mice treated with MMPt demonstrated far less disease progression as compared to the mice treated with NS or MP4. The mean clinical score of the MMPt-treated mice remained nearly 0 for up to about 22 days after immunization.

Example 4

This example demonstrates that CNS-infiltrating MOG-specific T cells are depleted following MMPt-treatment of mice with MOG-induced EAE.

Mice with MOG-induced EAE were untreated or treated with MMPt at a dose of 400 µg per mouse twice every other day as described in Example 3. The numbers of cells from naïve (unimmunized) mice, untreated EAE mice, or treated EAE mice that (a) expressed CD45 and CD4, (b) expressed CD4 and CD3, and (c) bound MOG tetramer and expressed CD4 was measured by fluorescence-activated cell sorting (FACS). The numbers of (a) CD45$^+$CD4$^+$, (b) CD4$^+$CD3$^+$, and (c) MOG tetramer$^+$CD4$^+$ cells were reduced in the MMPt-treated mice as compared to the untreated mice.

Example 5

This example demonstrates that MMPt reverses clinical EAE at the peak of disease.

Female C57BL/6 mice (10 weeks old) were immunized to develop EAE as described in Example 3. The peak of EAE was observed at Day 14 after immunization. Mice were injected retro-orbitally twice daily on Days 14, 16, and 18 after immunization with PBS (Group A) or MMPt at a dose of 400 µg (Group B) (FIG. 19A). Mean clinical scoring was determined for up to 20 days after immunization. The results are shown in FIG. 3. As shown in FIG. 3, MMPt treatment reversed clinical EAE at the peak of disease.

Example 6

This example demonstrates that MMPt treatment rapidly decreases spinal cord infiltrates in EAE mice.

Female C57BL/6 mice (10 weeks old) were immunized to develop EAE as described in Example 3. Mice were injected with a single dose (800 µg per mouse of MMPt (on day 14 post-immunization). The total number of CD45$^+$ leukocytes in the spinal cord was measured by FACS in wild-type (unimmunized) mice, untreated mice with EAE, and EAE mice treated with one dose of MMPt. The results are shown in FIG. 4A. As shown in FIG. 4A, one day after a single injection of MMPt, the total number of CD45$^+$ leukocytes in the spinal cord was decreased.

The total numbers of the various cell types in Table 1 that infiltrated the spinal cord were also measured by FACS in wild-type (unimmunized) mice, untreated mice with EAE, and EAE mice treated with one dose of MMPt. The results are shown in FIG. 4B. As shown in FIG. 4B, one day after a single injection of MMPt, the total numbers of CD3+ T cells, microglial cells, and macrophages in the spinal cord were decreased.

The percentage of CD45+/CD3+ T cells in the spinal cord of EAE mice was also depleted in MMPt-treated mice (15.2%) as compared to PBS-treated mice (22.8%) 15 days after a single injection of MMPt as measured by FACS.

TABLE 1

| Cell type | Phenotype |
| --- | --- |
| CD3+ T cells | CD45$^{high}$CD11b$^-$CD11c$^-$CD3$^+$ |
| Microglial cells | CD45$^{intermediate}$CD11b$^+$ |
| Macrophages | CD45$^{high}$CD11b$^+$CD11c$^-$Ly6G$^-$ |
| Dendritic cells (DCs) | CD45$^{high}$CD11b$^+$CD11c$^+$Ly6G$^-$ |
| Neutrophils | CD45$^{high}$Ly6G$^+$CD11b$^+$ |

In a separate experiment, female C57BL/6 mice (10 weeks old) were immunized to develop EAE as described in Example 3. Mice were injected with three doses (a total of 800 µg per mice per day, that is, 400 µg twice per mouse per day) every other day of MMPt (on day 14, 16, and 18 post immunization). The total number of CD45$^+$ leukocytes in the spinal cord was measured by FACS in wild-type (unimmunized) mice, untreated mice with EAE, and EAE mice treated with three doses of MMPt. The results are shown in FIG. 5A. As shown in FIG. 5A, five days after injection of three doses of MMPt, the total number of CD45$^+$ leukocytes in the spinal cord was dramatically decreased.

The total numbers of the various cell types shown in Table 1 that infiltrated the spinal cord were also measured by FACS in wild-type (unimmunized) mice, untreated mice with EAE, and EAE mice treated with three doses of MMPt. The results are shown in FIG. 5B. As shown in FIG. 5B, five days after injection of three doses of MMPt, the total numbers of CD3+ T cells, microglial cells, macrophages, and dendritic cells in the spinal cord were dramatically decreased.

The percentage of CD45+/CD3+ T cells in the spinal cord of EAE mice was also depleted in MMPt-treated mice (6.93%) as compared to PBS-treated mice (25.1%) 20 days after treatment with three doses of MMPt as measured by FACS.

The percentages of microglial cells, DCs, macrophages, and neutrophils were also depleted in the spinal cord of MMPt-treated EAE mice as compared to PBS-treated EAE mice 20 days after treatment with three doses of MMPt as measured by FACS. The depletion of spinal cord infiltrating cells was also confirmed by histopathological staining of spinal cord sections of naïve mice, EAE mice treated with PBS, and EAE mice treated with three doses of MMPt 20 days after treatment.

Example 7

This example demonstrates that the percentage of apoptotic CD4+ T cells in the spinal cord increases 20 hours after MMPt injection.

Mice with MOG-induced EAE were treated with one dose of MMPt (800 µg) or PBS on day 14 post immunization. The percentage of apoptotic CD4+ T cells in the spinal cord was measured 20 hours after MMPt injection by annexin V staining. The results are shown in FIG. 6. As shown in FIG. 6, 20 hours after MMPt injection, the percentage of apoptotic CD4+ T cells in the spinal cord was increased.

Example 8

This example demonstrates that MMPt treatment rapidly decreases pro-inflammatory cytokines in the spinal cord of EAE mice.

Mice with MOG-induced EAE were treated with PBS or one dose of MMPt (800 µg) on day 14 post-immunization. The fold enrichment of IL-1β and IFN-γ in the spinal cord relative to wild-type (unimmunized) mice was measured. The results are shown in FIGS. 7A and 7B. As shown in FIGS. 7A and 7B, the fold enrichment of IFN-γ and IL-1β in the spinal cord (relative to wild-type mice) was decreased in MMPt-treated mice as compared to PBS-treated mice 20 hours after MMPt injection.

Example 9

This example demonstrates that MMPt treatment blocks MOG-specific resting T cell proliferation while augmenting antigen (Ag)-responding T regulatory cell ($T_{reg}$) expansion in vitro.

To assess the tolerogen-specific T-cell response in MMPt-treated EAE-induced animals, C57BL/6 (B6) mice were immunized with MOG peptide to induce EAE (Day 0). On day 20, splenic lymphocytes were isolated from the wild-type (unimmunized), PBS (mock)-treated, and MMPt-treated mice and labeled with carboxyfluorescein succinimidyl ester (CFSE), an intracellular entrapped fluorescent dye for measuring cell proliferation. The responses of the isolated T lymphocytes was measured by flow cytometry six days after ex vivo MOG-peptide re-stimulations. Flow cytometery was carried out on the basis of the expression of (a) IFN-γ and IL-17 or (b) Foxp3 or (c) in the presence of CFSE.

The results showed that the MOG-specific T cells from the MMPt-treated mice had reduced proliferation responses and contained less IL-17 producers in response to MOG peptide stimulation as compared to the PBS (mock)-treated controls. Without being bound to a particular theory or mechanism, it is believed that the low frequency of MOG-specific T cells in the MMPt-treated animals is due to restimulation-induced cell death (RICD) in vivo. A significant increase in MOG-peptide reactive, Foxp3 positive populations in the MMPt-treated mice was also observed. Without being bound to a particular theory or mechanism, it is believed that MPPt treatment in vivo may be able to initiate a suppressive immune response that is beneficiary to the RICD-based EAE treatment in this model.

Example 10

This example demonstrates that MMPt prevents MOG-induced EAE.

Female C57BL/6 mice (10 weeks old) were intraperitoneally (i.p.) immunized with $MOG_{35-55}$ peptide (200 ng/dose) on Days 0 and 1. Mice were retro-orbitally injected twice daily with PBS or MMPt (400 µg, for a total of 800 µg per mouse per day) on Days 7, 9, and 11 before the appearance of the signs of EAE. On Day 12, the mice began to show signs of the early stages of EAE. Mean clinical scoring was determined for up to 21 days after immunization. The results are shown in FIG. 8. As shown in FIG. 8, mice treated with MMPt after immunization but before presenting with the signs of the early stages of EAE demonstrated a mean clinical score of nearly 0 for up to about 21 days after immunization.

Example 11

This example demonstrates that cyclosporin A (CsA) does not interfere with MMPt-mediated autoimmune T-cell deletion in vivo.

The immune system is composed of a panel of T cells that have a variety of avidities in recognizing a particular antigen, including self-antigens. A high-dose antigen stimulation may cause deletion of high-avidity T cells while it may also lead to proliferation of low-avidity T cell populations. These hard-to-kill, low-avidity T cells, when activated and expanded, may become autoimmune-reactive, which may counterbalance the therapeutic efficiency of RICD. Immunosuppresants, such as cyclosporin A (CsA), may inhibit antigen induced T-cell activation. Activated T cells pretreated with CsA remain sensitive to RICD, which may provide a basis for designing a therapeutic regimen combining RICD, which deletes unwanted T cells encountering strong TCR stimulations, and CsA, which inhibits further T-cell activation by the same toleragen.

MOG-peptide specific, TCR-transgenic (2D2 strain) T cells were isolated and stimulated by anti-CD3 antibody in vitro for three days before being labeled with CFSE and being adoptively transferred into C57BL/6 mice. The mice were then subjected to MMPt treatment in the presence or absence of CsA. The results are shown in FIG. 9. As shown in FIG. 9, the depletion of MOG-peptide specific T cells is not substantially affected by using CsA.

Example 12

This example demonstrates the dynamics of spinal cord-infiltrating macrophage, DCs and activated microglial cells after MMPt treatment.

Spinal cord infiltrating cells were isolated from EAE mice 15 days after immunization with MMPt and 20 hours after single dose of MMPt or PBS (control). The cells were analyzed by flow cytometry. The results are shown in FIG. 10A.

Spinal cord infiltrating cells were isolated from EAE mice 20 days after immunization with MMpt and after three doses of MMPt or PBS (control). The cells were analyzed by flow cytometry. The results are shown in FIG. 10B.

Example 13

This example demonstrates the expression of inflammatory cytokines in the spinal-cord tissues of MMPt and PBS (control)-treated EAE mice.

The expression of inflammatory cytokines (interleukin (IL)-2, IL6, IL10, IL18, IL23, and transforming growth factor beta 1 (TGFb1)) were measured by real-time quantitative reverse transcription PCR (Q-RT-PCR) in mRNA samples isolated from the spinal-cord tissues of MMPt and PBS (control)-treated EAE mice. The results are shown in FIG. 11. As shown in FIG. 11, IL-2 expression was significantly decreased compared to the measurable decreases in IL-6, IL-10 and TGFb1 mRNA in MMPt-treated EAE mice.

Example 14

This example demonstrates the histopathological staining of spinal cord sections of EAE mice 20 days after immunization.

EAE mice were treated with 800 μg MMPt on days 14, 16, 18 (three doses), and the spinal cord tissues were collected on day 20 after the disease-inducing immunization. With reference to FIG. 12, sections of fixed spinal cord tissues from age-matched normal (naïve) (left), phosphate buffered saline (PBS) (Mock), and 800 μg MMPt treated mice were stained with H&E (top panels), Toluidine blue (middle panels), and Luxol fast blue (LFB)-Periodic acid Schiff (PAS) stain (bottom panels), respectively. As shown in FIG. 12, MMPt treatment significantly ameliorated pathological myelin damage.

Example 15

This example demonstrates that MMPt treatment results in remyelination in axons in EAE mice.

Images (electron microscrope (EM)) were taken of myelin surrounding axons in healthy mice, mock (control)-treated EAE mice, and in EAE mice treated with MMPt. Mice were treated with three doses of control or 800 μg MMPt i.v. in accordance with the "therapeutic" schedule shown in FIG. 19A. The results are shown in FIGS. 13-15. As shown in FIGS. 13 and 14, the healthy mice have healthy myelin surrounding axons (FIG. 13), while the mock (control)-treated EAE mice have demyelinated, naked axons (FIG. 14). As shown in FIG. 15, the axons of MMPt-treated EAE mice undergo remyelination. FIG. 15 shows a typical structure of remyelination having occurred on an axon with its thin myelin sheath created by oligodendrocytes in MMPt-treated EAE mice. As shown in FIG. 15, the myelin is thinner than naturally myelinated axons. The thinner myelin sheath in the treated mice is evidence of remyelination.

Example 16

This example demonstrates the reduction of CD11b$^+$ CD45$^{high}$ monocytes and macrophages in the spinal cord 20 hours after MMPt treatment.

The MOG-induced EAE mice were intravenously treated with 800 μg MMPt or normal saline (control) on day 16 of disease-inducing immunization. The spinal cord-infiltrating monocytes (CD11b$^+$CD45$^{high}$) were analyzed by flow cytometry 20 hours post-MMPt treatment, and the corresponding CD11b$^+$CD45$^{high}$ monocytes/macrophages were isolated by flow cytometry sorting. The results are shown in FIG. 16. As shown in FIG. 16, CD11b$^+$CD45$^{high}$ monocytes and macrophages were reduced in the spinal cord 20 hours after MMPt treatment as compared to control treatment.

The absolute counts of T cells, CD45$^{high}$ monocytes, and microglia cells were obtained from the spinal cord tissues of the normal saline (mock) and MMPt treated EAE mice. Each group had 4 pooled mice. The results are shown in Table 2. The values in Table 2 are ×10$^5$.

TABLE 2

|  | T cell | CD45$^{high}$ | microglia |
| --- | --- | --- | --- |
| Mock | 4.6 | 14.1 | 4.6 |
| MMPt | 2.2 | 10.5 | 2.8 |

Example 17

This example demonstrates that monocyte cell proliferation is down-regulated in MMPt-treated mice.

The mRNA was prepared from the isolated monocytes of Example 16 and the gene expression profile was examined by microarray analysis (Gene Set Enrichment Analysis (GSEA)). GSEA is a sensitive and robust method for analyzing sets of genes that alter in expression in microarrays. The results are shown in FIG. 17. As shown in FIG. 17, a negatively regulated pattern of monocytes/macrophages was observed in the MMPt treated samples (red gradient area) as compared to the normal saline controls (mock).

Microarray analysis also revealed an up-regulation of a set of classical anti-inflammatory genes in the monocytes isolated from the spinal cord tissue of MMPt treated EAE mice as compared to the mock treated controls. The results are shown in Table 3. In Table 3, the fold of induction index is reflected in the column "ratio number," which is derived from comparing the gene expression levels of MMPt-treated samples to the mock-treated EAE samples.

TABLE 3

| Gene symbol | MMPt | MMPt. call | Untreated | Untreated. call | Ratio | Ratio.call | ProbeSetID |
| --- | --- | --- | --- | --- | --- | --- | --- |
| Pten | 218.8 | P | 85.85 | P | 2.55 | P | 1438454_at |
| Gsk3b | 92.4 | P | 39.08 | P | 2.36 | P | 1439949_at |
| Tet2 | 191.4 | P | 82.02 | P | 2.33 | P | 1438781_at |
| Rictor | 81.9 | P | 41.14 | P | 1.99 | P | 1453775_at |
| Mef2c | 238.1 | P | 121.27 | P | 1.96 | P | 1451506_at |
| Eif2ak2 | 64.5 | P | 33.37 | P | 1.93 | P | 1440866_at |
| Ube2c | 214.2 | P | 115.7 | P | 1.85 | P | 1452954_at |
| Bcl6 | 418.8 | P | 283.27 | P | 1.48 | P | 1421818_at |
| Ncorl | 16.9 | P | 9.27 | A | 1.82 | P | 1444760_at |

As shown in Table 3, Pten expression has a ratio of 2.5 (MMPt:Saline), indicating a suppression of Akt-mediated cell proliferation and survival signals.

Table 4 shows the results of microarray data analysis profiling cytokine gene differential expression in monocytes isolated from the spinal cord tissues of MMPt-treated and saline (mock) treated EAE mice.

TABLE 4

| Gene symbol | MMPt | MMPt. call | Untreated | Mock. call | Ratio | Ratio.call |
| --- | --- | --- | --- | --- | --- | --- |
| Il10 | 220.3 | P | 68.2 | P | 3.23 | P |
| Il18 | 499.9 | P | 436.4 | P | 1.15 | P |
| Il23a | 94.5 | P | 80.3 | A | 1.18 | P |
| Il1b | 3596.5 | P | 3297.8 | P | 1.09 | P |
| Tnf | 780.0 | P | 470.2 | P | 1.66 | P |
| Ifnb1 | 169.6 | P | 121.1 | P | 1.40 | P |
| Ccl8 | 210.6 | P | 456.2 | P | 0.46 | P |
| Ccl6 | 3910.3 | P | 5296.4 | P | 0.74 | P |
| Ccl9 | 2727.0 | P | 3397.9 | P | 0.80 | P |
| Ccl17 | 132.3 | P | 205.4 | P | 0.64 | P |

TABLE 4-continued

| Gene symbol | MMPt | MMPt. call | Untreated | Mock. call | Ratio | Ratio.call |
|---|---|---|---|---|---|---|
| Ccl2 | 518.2 | P | 397.0 | P | 1.31 | P |
| Ccl3 | 2923.4 | P | 2056.0 | P | 1.42 | P |
| Ccl4 | 1909.8 | P | 1245.5 | P | 1.53 | P |
| Ccl9 | 2083.6 | P | 2742.2 | P | 0.76 | P |
| Ccr2 | 112.3 | P | 54.4 | P | 2.07 | P |

The cytokine expression profile analysis showed a significant up-regulation of IL10 (ratio 3.2) and Stat3 (ratio 2.4) in the MMPt-treated samples, indicating the existence of an active anti-inflammatory response by the monocytes/macrophages in the spinal cord. Without being bound by a particular theory or mechanism, it is believed that IL10 signaling through the IL10 receptor (IL10r), activating Stat3, may trigger an anti-inflammatory phenotype of monocytes/macrophages after MMPt treatment.

Gene expression analysis by GSEA pathways analysis and KEGG analysis showed upregulation of genes involved in the immune signaling pathway, including MAPK and JAK-STAT for MMPt treated samples (FIG. 18A and FIG. 18B).

Example 18

This example demonstrates that MMPt treatment appears to significantly reduce spinal cord infiltrating CD11b positive monocytes. However, the percentage of cells expressing pro-IL1 beta does not appear to be affected, and the percentage of cells expressing tumor necrosis factor (TNF) alpha is slightly increased.

Monocytes were isolated from EAE-affected spinal cord tissue of PBS (control) and MMPt-treated mice. The isolated cells were subjected to flow cytometry analysis probing intracellular pro-IL1 beta and TNF alpha expression in $CD45.2^{high}/CD11b^+$ monocytes. MMPt treatment appeared to significantly reduce spinal cord infiltrating CD11b positive monocytes. However, the percentage of cells expressing pro-IL1 beta did not appear to be affected, and the percentage of cells expressing TNF alpha slightly increased.

Example 19

This example demonstrates that MMPt ameliorates MOGp35-55 induced EAE disease.

C57BL/6 mice immunized at day 0 were subjected to 400 μg MMPt per mouse i.v. twice daily at the indicated dates as shown in FIG. 19A. FIG. 19B shows a significant reduction of CNS inflammatory infiltration following MMPt treatment as shown by histopathological H&E staining of spinal cord sections from the corresponding representative of a normal mouse, a mouse treated on Day 20 with 3 doses of vehicle, or a mouse treated on Day 20 with 800 μg of MMPt.

Example 20

This example demonstrates the therapeutic effect of MMPt treatment in a representative EAE mouse.

An EAE mouse was treated with 400 μg MMPt i.v. injections b.i.d. every other day starting from day 11 after the MOGp35-55 immunization. The mouse was scored for clinical disease. Before MMPt treatment on Day 13, the mouse had a disease score of 3. After 4 doses of MMPt injections on day 17, the mouse presented an EAE score of 2. The mouse presented an EAE score of less than 1 on day 19 after all 6 doses of MMPt injections.

Example 21

This example demonstrates that MMPt induces RICD of MOGp35-55 specific T cells.

The depletion of infiltrated T cells in the spinal cord was measured after different doses of MMPt treatment. Starting from day 14, the peak of disease sign presentation post MOG immunization, the EAE mice were subjected to 800 μg MMPt i.v. injections every other day for one day or three days in total. The number of cells infiltrating the spinal cord expressing CD3 and CD45 was measured by flow cytometry. The results are shown in FIGS. 20A and 20B. As shown in FIGS. 20A and 20B, MMPt induces RICD of MOGp35-55 specific T cells.

The apoptosis of CD3+ T cells in the spinal cord was measured by staining with Annexin V after one dose of MMPt or Vehicle treatment. The results are shown in FIGS. 20C and 20D. As shown in FIGS. 20C and 20D, MMPt induces RICD of MOGp35-55 specific T cells.

Example 22

This example demonstrates the splenic MOGp35-55 specific T cell counts in experimental mice.

MOGp35-55/H2b tetramer positive T cells were measured in age-matched non-immunized C57BL/6 mice, (n=2), PBS control-treated EAE-induced mice (n=3), and EAE-induced mice treated with 6 doses of 400 μg injections of MMPt per mouse (n=3). The results are shown in FIGS. 21A and 21B.

Example 23

This example demonstrates the dose dependence and TCR specificity of RICD in vitro.

OT-I TCR-Tg T cells were stimulated by anti-CD3e and OVAp (SIINFEKL) (SEQ ID NO: 32)/H-2K(b) tetramers at various concentrations for 48 hours in vitro. The percent loss of activated OVA-specific OT-I TCR-Tg T cells was measured. The results are shown in FIG. 22A. As shown in FIG. 22A, the RICD was dose dependent.

Activated OT-I Tg T cells were stimulated with various doses of tetramers. The percent loss of activated OT-I Tg T cells was measured. The results are shown in FIG. 22B. As shown in FIG. 22B, OVA/H2-K(b) tetramer specifically targeted and caused programmed death of the OT-I TCR positive cells, while the equally activated bystander T cells were spared.

Example 24

This example demonstrates that RICD associates with dramatic suppression of inflammatory response in vivo and in vitro.

WT and IL1r−/− mice were scored for disease. The results are shown in FIG. 23A. As shown in FIG. 23A, IL1r−/− mice were resistant to EAE.

Using Q-PCR, the expression of the inflammatory cytokine IL-6 was measured in the spinal cord of EAE mice 20 hour after an 800 μg MMPt (or vehicle) single day treatment. The results are shown in FIG. 23B.

Using real-time PCR, the expression of inflammatory chemokines was measured 20 hours after vehicle or MMPt single dose treatment. The results are shown in FIG. 23C.

The effect of neutralization of IFN-γ on the recruitment of monocytes into the spinal cord was also measured. Starting from day 14, the peak of disease sign presentation post MOG immunization, the EAE mice received two intraperitoneal injections of 100 μg of IFN-γ specific neutralizing antibody or control antibody for two days. The subsets of spinal cord infiltrating cells was measured by FACS. The results are shown in FIG. 23D.

The IL-1beta production by peritoneal macrophages was also measured by ELISA in response to LPS stimulation in the absence or presence of in vitro activated T cells restimulated by anti-CD3 for 24 hours. The results are shown in FIG. 23E.

Intracellular pro-IL1b expression in isolated mouse peritoneal macrophages was also measured by flow cytometry in response to LPS and ATP stimulation co-cultured overnight with in vitro activated T cells in the absence or presence of anti-CD3 restimulation. The results are shown in FIG. 23F.

Example 25

This example demonstrates that MMPt-induced RICD results in a decrease of infiltrating monocytes and activated microglia in the spinal cord of EAE mice.

Induction and MMPt treatment of EAE is carried out in C56BL/6 mice as described in FIG. 19A.

The total numbers of leukocyte subsets was measured in the spinal cord of EAE mice treated with three doses of MMPt (on day 14 of EAE induction), in normal mice without EAE induction, or in EAE mice treated with three doses of vehicle. The results are shown in FIG. 24.

Example 26

This example demonstrates that depletion of encephalitogenic T cells by MMPt results in apoptosis of infiltrating monocytes in the CNS of EAE mice.

Flow cytometry was used to detect intracellular IL-10 and GM-CSF expression in spinal cord infiltrating T cells ($CD3^+$ $CD45.2^+$) of EAE mice that were treated with a single dose of normal saline (Vehicle) or 800 μg MMPt iv injections at day 14 of EAE induction. The results are shown in FIGS. 25A and 25B.

The percentage of Annexin V positive spinal-cord infiltrating monocytes (gated on CD11b+CD45.2$^{high}$) was also measured by flow cytometry. The results are shown in FIG. 25C.

Spinal cord sections from a normal mouse, an EAE-induced mouse receiving MMPt treatment, and an EAE mouse treated with normal saline. The results are shown in FIG. 25D.

Example 27

This example demonstrates the release of IL-10 into the supernatant of peritoneal macrophages cultured overnight with in vitro activated 2D2 mice T cells restimulated by $Mog_{35-55}$ peptide.

Peritoneal macrophages were cultured overnight with in vitro activated 2D2 mice T cells restimulated by $Mog_{35-55}$ peptide. The IL-10 released in the supernatant was measured. The results are shown in FIG. 26.

Example 28

This example demonstrates the upregulation of Pten level after MMPt treatment and subsequent inhibition of Akt activation.

GSEA analysis revealed the negative regulation of the cell proliferation pathway as one of the most extensively upregulated pathways in MMPt-treated spinal cord-sorted CD11b+ CD45high infiltrating monocytes. Mice were treated with three doses of 800 μg MMPt i.v. in accordance with the "treatment" schedule shown in FIG. 19A. The top pathways affected by MMPt in spinal cord sorted CD11b+CD45high infiltrating monocytes is shown in FIG. 27A. FIG. 27B shows a heat map of gene expression, relative to vehicle-treated mice in spinal cord sorted CD11b+CD45high infiltrating monocytes.

The Pten expression level in spinal cord tissues after MMPt single dose treatment was measured by Real-time PCR. The results are shown in FIG. 27C.

The expression of pro-apoptotic molecules in spinal cord tissue after MMPt treatment was measured by Real-time PCR. Mice were treated with three doses of 800 μg MMPt i.v. in accordance with the "treatment" schedule shown in FIG. 19A. The results are shown in FIG. 28A.

Pten, Akt, Bad, and Caspase-3 activation in peritoneal macrophages cultured together with in vitro generated effector 2D2 or DO11.10 T cells restimulated by $Mog_{35-55}$ peptide or $OVA_{323-339}$ was assessed by western blot. The results are shown in FIG. 28B.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A fusion protein comprising three human autoantigenic proteins, wherein a first human autoantigenic protein comprises a truncated myelin oligodendrocyte glycoprotein (MOG) amino acid sequence, a second human autoantigenic protein comprises a myelin basic protein (MBP) amino acid sequence, and a third human autoantigenic protein comprises a truncated proteolipid protein (PLP) amino acid sequence;
   wherein:
   the truncated MOG amino acid sequence is SEQ ID NO: 1 or 25;
   the MBP amino acid sequence is SEQ ID NO: 2 or 28; and
   the truncated PLP amino acid sequence is SEQ ID NO: 3.

2. The protein of claim 1, wherein the MOG amino acid sequence is conjugated or fused to the MBP amino acid sequence via a linker.

3. The protein of claim 1, wherein the amino acid sequence is SEQ ID NO: 9.

4. The protein of claim 1, further comprising a Tobacco Etch Virus (TEV) cleavage sequence.

5. The protein of claim 1, further comprising a histidine tag.

6. The protein of claim 1, wherein the protein is admixed with a pharmaceutically acceptable carrier.

* * * * *